(12) United States Patent
Schrøder Glad et al.

(10) Patent No.: US 11,447,479 B2
(45) Date of Patent: Sep. 20, 2022

(54) COMPOUNDS ACTIVE TOWARDS NUCLEAR RECEPTORS

(71) Applicant: NUEVOLUTION A/S, Copenhagen (DK)

(72) Inventors: Sanne Schrøder Glad, Copenhagen (DK); Ian Sarvary, Copenhagen (DK); Alex Haahr Gouliaev, Copenhagen (DK); Thomas Franch, Copenhagen (DK); Søren Jensby Nielsen, Copenhagen (DK); Luigi Piero Stasi, Copenhagen (DK)

(73) Assignee: NUEVOLUTION A/S, Copenhagen (DK)

( * ) Notice: Subject to any disclaimer, the term of this patent is extended or adjusted under 35 U.S.C. 154(b) by 74 days.

(21) Appl. No.: 17/126,170

(22) Filed: Dec. 18, 2020

(65) Prior Publication Data

US 2021/0188828 A1    Jun. 24, 2021

Related U.S. Application Data

(60) Provisional application No. 62/951,239, filed on Dec. 20, 2019.

(51) Int. Cl.
| | | |
|---|---|---|
| *C07D 401/14* | (2006.01) |
| *C07D 413/14* | (2006.01) |
| *A61K 31/506* | (2006.01) |
| *A61K 31/5377* | (2006.01) |
| *A61P 19/02* | (2006.01) |
| *A61P 29/00* | (2006.01) |

(52) U.S. Cl.
CPC ........... *C07D 413/14* (2013.01); *A61P 19/02* (2018.01); *A61P 29/00* (2018.01); *C07D 401/14* (2013.01)

(58) Field of Classification Search
CPC .............. C07D 413/14; C07D 401/14; A61K 31/5377; A61K 31/506; A61P 19/02
USPC ........................ 544/122, 322; 514/235.8, 256
See application file for complete search history.

(56) References Cited

U.S. PATENT DOCUMENTS

| | | |
|---|---|---|
| 4,298,602 A | 11/1981 | Pawloski |
| 5,463,071 A | 10/1995 | Himmelsbach et al. |
| 5,530,129 A | 6/1996 | Gallenkamp et al. |
| 7,931,909 B2 | 4/2011 | Hughes et al. |
| 8,338,439 B2 | 12/2012 | Singh et al. |
| 10,683,393 B2 | 6/2020 | Boydston et al. |
| 10,689,383 B2 | 6/2020 | Glad et al. |
| 2003/0191121 A1 | 10/2003 | Miller et al. |
| 2004/0054173 A1 | 3/2004 | Kimura et al. |
| 2004/0087577 A1 | 5/2004 | Pratt et al. |
| 2004/0097492 A1 | 5/2004 | Pratt et al. |
| 2004/0180906 A1 | 9/2004 | Flynn et al. |
| 2005/0124623 A1 | 6/2005 | Bender et al. |
| 2005/0153989 A1 | 7/2005 | Grotzfeld et al. |
| 2005/0182045 A1 | 8/2005 | Nagase et al. |
| 2005/0245536 A1 | 11/2005 | Hao et al. |
| 2005/0288286 A1 | 12/2005 | Flynn et al. |
| 2006/0004018 A1 | 1/2006 | Xue et al. |
| 2006/0052374 A1 | 3/2006 | Carroll et al. |
| 2006/0069093 A1 | 3/2006 | Scarborough et al. |
| 2006/0199821 A1 | 9/2006 | Tester et al. |
| 2006/0235017 A1 | 10/2006 | Cirillo et al. |
| 2006/0241104 A1 | 10/2006 | Borzilleri et al. |
| 2006/0281712 A1 | 12/2006 | Yen et al. |
| 2008/0021063 A1 | 1/2008 | Kazantsev |
| 2008/0070319 A1 | 3/2008 | Makino |
| 2009/0018112 A1 | 1/2009 | Chapdelaine et al. |
| 2009/0018116 A1 | 1/2009 | Jin et al. |
| 2009/0018134 A1 | 1/2009 | Pike et al. |
| 2009/0018166 A1 | 1/2009 | Amin et al. |
| 2009/0029994 A1 | 1/2009 | Nakamura et al. |
| 2009/0036434 A1 | 2/2009 | Jones et al. |
| 2009/0069559 A1 | 3/2009 | Kazantsev |
| 2009/0143302 A1 | 6/2009 | Yen et al. |
| 2009/0163545 A1 | 6/2009 | Goldfarb |
| 2010/0152445 A1 | 6/2010 | Bolin et al. |
| 2010/0249153 A1 | 9/2010 | Tandon et al. |
| 2011/0135604 A1 | 6/2011 | Casarez et al. |
| 2011/0281842 A1 | 11/2011 | Michaelides et al. |
| 2012/0142714 A1 | 6/2012 | Yasuma et al. |
| 2012/0214762 A1 | 8/2012 | Staben et al. |
| 2012/0264798 A1 | 10/2012 | Sinha et al. |
| 2013/0040855 A1 | 2/2013 | Takayama et al. |
| 2013/0158031 A1 | 6/2013 | Cai et al. |
| 2013/0190249 A1 | 7/2013 | Lemieux et al. |
| 2013/0231519 A1 | 9/2013 | Heinrich et al. |
| 2014/0018361 A1 | 1/2014 | Harriman et al. |
| 2020/0392140 A1 | 12/2020 | Glad et al. |

FOREIGN PATENT DOCUMENTS

| | | |
|---|---|---|
| CL | 201700271 | 10/2017 |
| CL | 201700287 | 11/2017 |
| CL | 201701288 | 12/2017 |
| CL | 201701289 | 3/2018 |
| CN | 102786512 A | 11/2012 |
| CN | 103588795 A | 2/2014 |
| DE | 3737748 A1 | 5/1989 |

(Continued)

OTHER PUBLICATIONS

33 Substances CAS Registry Nos. 1515972-57-2; 357614-47-2; 1537342-62-3; 357614-41-6, 1509319-43-0; 357614-39-2; 1508163-79-8; 1543241-09-3; 1507549-73-6; 1539058-95-1; 1504736-18-8; 1538881-49-0; 1502546-73-7; 537342-62-3; 1502393-44-3; 1536916-94-5; 1501684-14-5; 1536417-79-4; 1500313-42-7; 1529040-93-4; 1499708-15-4; 1526739-06-9; 1020711-29-8; 1526652-58-3; 1020711-25-4; 1522387-54-7; 403668-62-2; 1522083-19-7; 357614-51-8; 1521680-88-5; 357614-49-4; 1519623-48-3; 357614-48-3 (2014).

(Continued)

*Primary Examiner* — Charanjit Aykakh
(74) *Attorney, Agent, or Firm* — Marshall, Gerstein & Borun LLP

(57) ABSTRACT

Disclosed are compounds active towards nuclear receptors, pharmaceutical compositions containing the compounds and use of the compounds in therapy.

21 Claims, No Drawings

(56) References Cited

FOREIGN PATENT DOCUMENTS

| | | |
|---|---|---|
| DE | 4124942 A1 | 1/1993 |
| DE | 10108480 A1 | 9/2002 |
| EP | 0384244 A1 | 8/1990 |
| EP | 0419831 A2 | 4/1991 |
| EP | 0434341 A1 | 6/1991 |
| EP | 1396489 A1 | 3/2004 |
| FR | 2870541 A1 | 11/2005 |
| FR | 2926556 A1 | 7/2009 |
| JP | 04-348326 A | 12/1992 |
| JP | 06-220059 A | 8/1994 |
| JP | 10-251255 A | 9/1998 |
| JP | 2000-086663 A | 3/2000 |
| JP | 2002-284779 A | 10/2002 |
| JP | 2007-507529 A | 3/2007 |
| JP | 2007-119450 A | 5/2007 |
| JP | 2007-126551 A | 5/2007 |
| JP | 2007-186580 A | 7/2007 |
| JP | 2008-501698 A | 1/2008 |
| JP | 2008-051696 A | 3/2008 |
| JP | 2012-519005 A | 8/2012 |
| JP | 2013-517809 A | 5/2013 |
| WO | 1993/14082 A1 | 7/1993 |
| WO | 1993/22311 A1 | 11/1993 |
| WO | 1996/40142 A1 | 12/1996 |
| WO | 1997/12878 A1 | 4/1997 |
| WO | 1997/44038 A1 | 11/1997 |
| WO | 1998/23613 A1 | 6/1998 |
| WO | 2001/12601 A1 | 2/2001 |
| WO | 2001/030778 A1 | 5/2001 |
| WO | 2001/047921 A1 | 7/2001 |
| WO | 2001/57038 A1 | 8/2001 |
| WO | 2002/22584 A1 | 3/2002 |
| WO | 2003/11836 A1 | 2/2003 |
| WO | 2003/45941 A1 | 6/2003 |
| WO | 2003/66604 A2 | 8/2003 |
| WO | 2003/75828 A2 | 9/2003 |
| WO | 2003/94918 A1 | 11/2003 |
| WO | 2003/101959 A1 | 12/2003 |
| WO | 2004/000843 A1 | 12/2003 |
| WO | 2004/014384 A2 | 2/2004 |
| WO | 2004/039785 A1 | 5/2004 |
| WO | 2004/039786 A1 | 5/2004 |
| WO | 2004/039788 A1 | 5/2004 |
| WO | 2004/054987 A1 | 7/2004 |
| WO | 2004/060305 A2 | 7/2004 |
| WO | 2004/060306 A2 | 7/2004 |
| WO | 2004/083174 A2 | 9/2004 |
| WO | 2004/083185 A2 | 9/2004 |
| WO | 2004/101557 A1 | 11/2004 |
| WO | 2004/110350 A2 | 12/2004 |
| WO | 2005/033072 A2 | 4/2005 |
| WO | 2005/040119 A1 | 5/2005 |
| WO | 2005/067546 A2 | 7/2005 |
| WO | 2005/068457 A1 | 7/2005 |
| WO | 2005/084667 A1 | 9/2005 |
| WO | 2005/111003 A1 | 11/2005 |
| WO | 2005/117909 A2 | 12/2005 |
| WO | 2005/121121 A2 | 12/2005 |
| WO | 2005/123731 A2 | 12/2005 |
| WO | 2006/004741 A2 | 1/2006 |
| WO | 2006/022773 A1 | 3/2006 |
| WO | 2006/045828 A1 | 5/2006 |
| WO | 2006/074057 A2 | 7/2006 |
| WO | 2006/076706 A1 | 7/2006 |
| WO | 2006/091963 A1 | 8/2006 |
| WO | 2006/122773 A1 | 11/2006 |
| WO | 2007/012661 A1 | 2/2007 |
| WO | 2007/021941 A2 | 2/2007 |
| WO | 2007/030574 A2 | 3/2007 |
| WO | 2007/068418 A1 | 6/2007 |
| WO | 2007/072163 A2 | 6/2007 |
| WO | 2007/072201 A2 | 6/2007 |
| WO | 2007/080382 A1 | 7/2007 |
| WO | 2007/088277 A1 | 8/2007 |
| WO | 2007/107545 A1 | 9/2007 |
| WO | 2007/121280 A1 | 10/2007 |
| WO | 2008/005368 A2 | 1/2008 |
| WO | 2008/005538 A2 | 1/2008 |
| WO | 2008/011476 A2 | 1/2008 |
| WO | 2008/023159 A1 | 2/2008 |
| WO | 2008/023180 A1 | 2/2008 |
| WO | 2008/074982 A1 | 6/2008 |
| WO | 2008/104077 A1 | 9/2008 |
| WO | 2008/115973 A2 | 9/2008 |
| WO | 2008/152093 A2 | 12/2008 |
| WO | 2009/007749 A2 | 1/2009 |
| WO | 2009/007750 A1 | 1/2009 |
| WO | 2009/007751 A2 | 1/2009 |
| WO | 2009/017664 A1 | 2/2009 |
| WO | 2009/055331 A2 | 4/2009 |
| WO | 2009/079683 A1 | 7/2009 |
| WO | 2009/099193 A1 | 8/2009 |
| WO | 2009/102736 A1 | 8/2009 |
| WO | 2009/103432 A2 | 8/2009 |
| WO | 2009/123221 A1 | 10/2009 |
| WO | 2009/128661 A2 | 10/2009 |
| WO | 2009/134384 A1 | 11/2009 |
| WO | 2009/149188 A1 | 12/2009 |
| WO | 2009/156484 A2 | 12/2009 |
| WO | 2010/012442 A2 | 2/2010 |
| WO | 2010/020432 A2 | 2/2010 |
| WO | 2010/022121 A1 | 2/2010 |
| WO | 2010/022125 A1 | 2/2010 |
| WO | 2010/022128 A1 | 2/2010 |
| WO | 2010/036316 A1 | 4/2010 |
| WO | 2010/048207 A2 | 4/2010 |
| WO | 2010/052569 A2 | 5/2010 |
| WO | 2010/080996 A1 | 7/2010 |
| WO | 2010/100127 A1 | 9/2010 |
| WO | 2010/114957 A1 | 10/2010 |
| WO | 2010/120994 A2 | 10/2010 |
| WO | 2010/129053 A2 | 11/2010 |
| WO | 2010/129242 A1 | 11/2010 |
| WO | 2010/135470 A1 | 11/2010 |
| WO | 2011/017513 A1 | 2/2011 |
| WO | 2011/022440 A2 | 2/2011 |
| WO | 2011/029043 A1 | 3/2011 |
| WO | 2011/029046 A1 | 3/2011 |
| WO | 2011/049946 A1 | 4/2011 |
| WO | 2011/055911 A1 | 5/2011 |
| WO | 2011/075684 A1 | 6/2011 |
| WO | 2011/078143 A1 | 6/2011 |
| WO | 2011/105572 A1 | 9/2011 |
| WO | 2011/115940 A1 | 9/2011 |
| WO | 2011/143129 A1 | 11/2011 |
| WO | 2011/153553 A2 | 12/2011 |
| WO | 2012/037226 A1 | 3/2012 |
| WO | 2012/041872 A1 | 4/2012 |
| WO | 2012/041873 A1 | 4/2012 |
| WO | 2012/046869 A1 | 4/2012 |
| WO | 2012/074022 A1 | 6/2012 |
| WO | 2012/103295 A2 | 8/2012 |
| WO | 2012/147516 A1 | 11/2012 |
| WO | 2012/147890 A1 | 11/2012 |
| WO | 2012/163773 A1 | 12/2012 |
| WO | 2012/166716 A2 | 12/2012 |
| WO | 2013/017461 A1 | 2/2013 |
| WO | 2013/019824 A2 | 2/2013 |
| WO | 2013/022766 A1 | 2/2013 |
| WO | 2013/036912 A2 | 3/2013 |
| WO | 2013/052526 A1 | 4/2013 |
| WO | 2013/068306 A1 | 5/2013 |
| WO | 2013/090912 A1 | 6/2013 |
| WO | 2013/117649 A1 | 8/2013 |
| WO | 2013/134467 A1 | 9/2013 |
| WO | 2013/157022 A1 | 10/2013 |
| WO | 2013/178075 A1 | 12/2013 |
| WO | 2013/183673 A1 | 12/2013 |
| WO | 2014/005129 A1 | 1/2014 |
| WO | 2014/015523 A1 | 1/2014 |
| WO | 2014/015675 A1 | 1/2014 |
| WO | 2014/015830 A1 | 1/2014 |
| WO | 2014/015936 A1 | 1/2014 |

(56) References Cited

FOREIGN PATENT DOCUMENTS

| WO | 2014/017513 A1 | 1/2014 |
|---|---|---|
| WO | 2014/019908 A2 | 2/2014 |
| WO | 2014/185358 A1 | 11/2014 |
| WO | 2015/033558 A1 | 3/2015 |
| WO | 2015/129263 A1 | 9/2015 |
| WO | 2016/020288 A1 | 2/2016 |
| WO | 2016/020295 A1 | 2/2016 |
| WO | 2016/020320 A1 | 2/2016 |
| WO | 2016/081670 A2 | 5/2016 |
| WO | 2016/081918 A1 | 5/2016 |

OTHER PUBLICATIONS

Alm et al., Effects of topically applied PGF2 alpha and its isopropylester on normal and glaucomatous human eyes, Prog. Clin. Biol. Res., 312:447-458 (1989).

Aloisi et al., Lymphoid neogenesis in chronic inflammatory diseases, Nat. Rev. Immunol., 6:205-217 (2006).

Barnes et al., Immunology of asthma and chronic obstructive pulmonary disease, Nat. Rev. Immunol., 8:183-192 (2008).

Bronner et al., ROR.gamma. antagonists and inverse agonists: a patent review, Expert Opinion on Therapeutics Patents, 27(1):101-112 (2017).

Caira, Crystalline Polymorphism of Organic Compounds, Topics in Current Chemistry, 198:163-208 (1998).

Cas Reg No. 929970-65-0, STN Entry Date: Apr. 13, 2007; 7H-Pyrrolo[2,3-d]pyrimidin-4-amine,5,6-dimethyl-7-(phenylmethyl)-N-(4-pyridinylmethyl)-[2].

Cas Reg. No. 1539496-16-6, STN Entry Date: Feb. 9, 2014; 4,6-Pyrimidinediamine, N6-ethyl-N4-methyl-5-(1-methylethyl)-N4-[(1-methyl-1 H-pyrazol-4-yl)methyl- ].

Cas Reg. No. 1540192-80-0, STN Entry Date: Feb. 10, 2014; 4,6-Pyrimidinediamine, N4,N6-diethyl-2,5-dimethyl-N4-(2-thienylmethyl).

CAS Reg. No. 1542543-24-7, STN Entry Date: Feb. 14, 2014; 4,6-Pyrimidinediamine, N4-[(4 chlorophenyl)methyl]-N4,5-dimethyl-N6-propyl.

Cas Reg. No. 1543250-40-3, STN Entry Date: Feb. 14, 2014; 4,6-Pyrimidinediamine, 5-methoxy-N4-methyl-N6-propyl-N4-[(tetrahydro-2H-pyran-3-yl)methyl].

Cas Reg. No. 1544786-92-6, STN Entry Date: Feb. 16, 2014; 4,6-Pyrimidinediamine, N6-ethyl-N4,2-dimethyl-N4-[(5-methyl-2-furanyl)methyl].

CAS Reg.No. 1101785-73-2, STN Entry Date: Feb. 6, 2009; L-Alanine, N-[7-(2-furanylmethyl)-5,6-dimethyl-7H-pyrrolo[2,3-d]pyrimidin-4-yl]- [2].

Chang et al., Pharmacologic Repression of Retinoic Acid Receptor—Related Orphan Nuclear Receptor γ is Therapeutic in the Collagen-Induced Arthritis Experimental Model, Arthritis & Rheumatism, 66(3):579-588 (2014).

Chang et al., RORs in autoimmune disease, sphingosine-1-phosphate signaling in immunology and infectious diseases, Curr. Topics in Microb. Immun., 378:171-182 (2014).

Cook et al., Retinoic Acid-Related Orphan Receptors (RORs): Regulatory Functions in Immunity, Development, Circadian Rhythm, and Metabolism, Nuclear Receptor Research, 2, Article ID 101185:1-24 (2015).

Cyr et al., Recent progress on nuclear receptor ROR gamma modulators, Bioorganic & Medicinal Chemistry Letters 26(18):4387-4393 (2016).

Database Registry, 2013, RN 1445611-7, 1424439 [03, 2006.01, 01, 1, 1423758- [35, 2006.01, 74] 3, 13118835, 1281111-22-5, 1281111-13-4; Retrieved from STN international [online]; retrieved on Apr. 12, 2019.

Fa et al., Synthesis, structure, and fullerene-complexing property of azacalix[6]aromatics, J. Org. Chem., 79:3559-3571 (2014).

Fan et al., Retinoic Acid Receptor-Related Orphan Receptors: Critical Roles in Tumorigenesis, Frontiers in Immunology. vol. 9 Article 1187:1-10 (2018).

Fauber et al., Modulators of the Nuclear Receptor Retinoic Acid Receptor-Related Orphan Receptor-gamma (ROR gamma or RORc), J. Med. Chem., 57:5871-5892 (2014).

Fingl et al., The pharmacological basis of therapeutics, Ch. 1 (1975).

Han et al., Efficient and library-friendly synthesis of furo- and thienol[2,3-d] pyrimidin-4-amine derivatives by microwave irradiation, Tetrahedron Letters, 51: 629-632 (2010).

Huh et al., Small molecule inhibitors of RORγt: Targeting Th17 cells and other applications, NIH public access author manuscript, Eur. J. Immunol., 42(9):2232-2237 (2012).

International Application No. PCT/EP2015/067692, International Search Report and Written Opinion, dated Sep. 21, 2015.

International Application No. PCT/EP2015/067713, International Preliminary Report on Patentability, dated Feb. 16, 2017.

International Application No. PCT/EP2015/067713, International Search Report and Written Opinion, dated Sep. 22, 2015.

International Preliminary Report on Patentability for corresponding International Application No. PCT/EP2015/067692, dated Feb. 16, 2017.

IUPAC-IUB commission on biochemical nomenclature, Biochem. 11:942-944 (1972).

Jager et al., Th1, Th17, and Th9 effector cells induce experimental autoimmune encephalomyelitis with different pathological phenotypes, J. Immunol., 183(11):7169-7177 (2009).

Joshi, Microparticulates for ophthalmic drug delivery, J. Ocul. Pharmacol., 10(1):29-45 (1994).

Kamenecka et al., Synthetic modulators of the retinoic acid receptor-related orphan receptors, Med. Chem. Commun., 4:764-776 (2013).

Kim et al., Substituted pyrimidines as cannabinoid CB1 receptor ligands, Bioorganic & Medicinal Chemistry Letters, 19:4692-4697 (2009).

Klecka et al., Direct C-H borylation and C-H arylation of pyrrolo[2,3d]pyrimidines: synthesis of 6,8-disubstituted7-deazapurines, Org. Biomol. Chem., 7:866-868 (2009).

Kojetin et al., REV-ERB and ROR nuclear receptors as drug targets, Nature Rev. Drug Disc., 13:197-216 (2014).

Kosary et al., Preparation of pyrimidine derivatives with potential cardiotonic activity, Acta Pharmacetical Hungarica., 56(6):7147-7156 (2003).

Kosary et al., Preparation of pyrimidine derivatives with potential cardiotonic activity, Acta. Pharmacetical Hungarica., 56(6):241-247 (abstract CA 112:216531), Retrieved from Chemical Abstracts (1989).

Ma et al., Combinatorial synthesis of substituted biaryls and heterocyclic arylamines, J. Comb. Chem., 6(3):426-430 (2004).

Magliozzi et al., Meningeal B-cell follicles in secondary progressive multiple sclerosis associate with early onset of disease and severe cortical pathology, Brain, 130(4):1089-1104 (2007).

Marquet et al., New series of purine analogs with antimitotic action. Structure activity relations, Chimica. Therapeutica., 6(6):427-38 (1971).

Marquet et al., Sur une nouvelle serie d'analogues puriques a action antimitotique: relations structure—activite, European Journal of medicinal chemistry—Chimie Therapeutique, 6:427-438 (1971).

Mashkovskiy, Lekarstvennie sredstva, Moscow. Medicina. part 1:8 with partial English translation (1993).

Mayer et al., Efficacy of a novel hydrogel formulation in human volunteers, Ophthalmologica, 210(2):101-103 (1996).

Meier et al., Ectopic lymphoid-organ development occurs through interleukin 7-mediated enhanced survival of lymphoid-tissue-inducer cells, Immunity, 26(5):643-654 (2007).

Miossec et al., Targeting IL-17 and TH17 cells in chronic inflammation, Nature Rev. Drug Disc, 11:763-776 (2012).

Montebugnoli et al., Traceless solid-phase synthesis of 2,4,6-chlorodiamino and triaminopyrimidines, Tetrahedron, 59:7147-7156 (2003).

Mordenti, Intraocular pharmacokinetics and safety of a humanized monoclonal antibody in rabbits after intravitreal administration of a solution or a PLGA microsphere formulation, Toxicol. Sci, 52(1):101-106 (1999).

(56) References Cited

OTHER PUBLICATIONS

Muller et al., Chiral Pyrrolo[2,3d]pyrimidine and pyrimido[4,5-b]indole derivatives: structure-activity relationships of potent, highly stereoselective A.sub.1-adenosine receptor antagonists, J. Med. Chem., 39:2482-2491 (1996).

Nogrady, Medicinal chemistry a biochemical approach, Oxford university press, New York, 388-392 (1985).

Pandya et al., Combating Autoimmune Diseases With Retinoic Acid Receptor-Related Orphan Receptor-γ (RORγ or RORc) Inhibitors: Hits and Misses, J. Med. Chem., 61(24):10976-10995 (2018).

Pryde et al., The discovery of a novel prototype small molecule TLR7 agonist for the treatment of hepatitis C virus infection, Med. Chem. Commun., 2:185-189(2011).

Pubchem (National Center for Biotechnology Information. Pubchem Compound Database; CID=3236972, https://pubchem.ncbi.nlm.nih.gov/compound/3236972 (accessed Sep. 15, 2018), created Aug. 16, 2005, pp. 1-13).

Search Report for Swedish Patent Application No. 1450920-2, dated Feb. 17, 2015.

Search Report for Swedish Patent Application No. 1451406-1, dated May 29, 2015.

Serafini et al., Detection of ectopic b-cell follicles with germinal centers in the meninges of patients with secondary progressive multiple sclerosis, Brain Pathol., 14(2):164-174 (2004).

Shedden et al., Efficacy and tolerability of timolol maleate ophthalmic gel-forming solution versus timolol ophthalmic solution in adults with open-angle glaucoma or ocular hypertension: a six-month, double-masked, multicenter study, Clin. Ther., 23(3):440-450 (2001).

Solt et al., Action of RORs and their ligands in (patho) physiology, Trends in Endocrinology and Metabolism, 23(12):619-627 (2012).

Traverso et al., The syntheses and pharmacological activities of amide, sulfamide, and urea derivatives of 4,6-diaminopyrimidines, J. Med. Pharm. Chem., 91:808-15 (1962).

Tyukavkina et al., Bioorganicheskaya himiya, moskva, Drofa., 83-85 with partial English translation (2005).

Upadhyaya et al., Identification of adducts formed in the reactions of 5'-acetoxy-N'-nitrosonornicotine with deoxyadenosine, thymidine, and DNA, Chem. Res. Toxicol., 21:2164-2171 (2008).

Wu et al., Discovery of aminoheterocycles as potent and brain penetrant prolylcarboxypeptidase inhibitors, Bioorganic & Medicinal Chemistry Letters, 22:1727-1730 (2012).

Yang et al., Discovery of Tertiary Amine and Indole Derivatives as Potent ROR.gamma.t Inverse Agonists, ACS Medical Chemistry Letters, 5:65-68 (2014).

Yoo et al., Synthesis of mono-, Di-, and triaminosubstituted-Pyrimidine derivatives, Korean J. Med. Chem., 9:83-86 (1999).

COMPOUNDS ACTIVE TOWARDS NUCLEAR RECEPTORS

CROSS REFERENCE TO RELATED APPLICATIONS

This application claims the priority benefit under 35 U.S.C. § 119(e) of U.S. Provisional Patent Application No. 62/951,239, filed Dec. 20, 2019 the disclosure of which is incorporated herein by reference in its entirety.

FIELD

Aspects and embodiments described herein relate to compounds active towards nuclear receptors, pharmaceutical compositions comprising the compounds, and methods of treating inflammatory, metabolic, oncologic and autoimmune diseases or disorders using the compounds.

BACKGROUND

Nuclear receptors are a family of transcription factors involved in the regulation of physiological functions, such as cell differentiation, embryonic development, and organ physiology. Nuclear receptors have also been identified as important pathological regulators in diseases such as cancer, diabetes, and autoimmune disorders.

Examples of nuclear receptors include the nuclear retinoic acid receptor-related orphan receptors (RORs). RORs contain four principal domains: an N-terminal A/B domain, a DNA-binding domain, a hinge domain and a ligand binding domain. Binding of ligands to the ligand-binding domain is believed to cause conformational changes in the domain resulting in downstream actions. Different isoforms exist and these isoforms differ in their N-terminal A/B domain only (Jetten, 2009, Nuclear Receptor Signaling).

RORs consist of three members, namely ROR alpha (RORα or RORa), ROR beta (RORβ or RORb) and ROR gamma (RORγ or RORc).

RORα is expressed in many tissues such as cerebellar Purkinje cells, the liver, thymus, skeletal muscle, skin, lung, adipose tissue and kidney. RORα regulates neuronal cell development, bone metabolism, and arteriosclerosis (Jetten, 2009, Nuclear Receptor Signaling). Additionally, RORα plays a role in the immune responses, such as in the regulation interleukin (IL) 17A expression in T helper (Th) 17 cells and the function of T regulatory (Treg) cells (Castro PLOS 2017; Malhotra 2018).

RORβ exhibits a restriction pattern of expression limited to certain regions of brain (cerebral cortex, thalamus, hypothalamus and pineal gland) as well as retina (Jetten, 2009, Nuclear Receptor Signaling). RORβ has been related to epilepsy and together with RORa also to bipolar disease (Rudolf 2016; Lai 2015).

RORγ shows a broad expression pattern and was the most recently discovered of the three members. To date two different protein isoforms have been recorded: RORγ1 and RORγ2 (RORγ2 is also known as RORγt). Generally RORγ is used to describe RORγ1 and/or RORγt. RORγ1 is expressed in many tissues and is predominantly expressed in the kidneys, liver, and skeletal muscle. In contrast, expression of RORγt is restricted to some cell types of the immune system and to lymphoid organs such as the thymus and secondary lymphoid tissues (Hirose 1994; Jetten, 2009, Nuclear Receptor Signaling).

RORγt has been identified as a key regulator of Th17 cell differentiation and IL-17 production by γδ T cells, Th17 cells, T cytotoxic (Tc) 17 cells and innate lymphoid cells type 3 (ILC3) cells (Gaffen 2014). Th17 cells are a subset of T helper cells which preferentially produce the cytokines IL-17A, IL-17F, IL-21 and IL-22 (Castro PLOS 2017). T cells lacking RORγt failed to differentiate into Th17 cells even under Th17-polarizing culture conditions, while overexpression of RORγt in naïve CD4+ T cells was sufficient to accelerate the expression of Th17-related cytokines and chemokines (Gaffen 2014, Nat Rev Immunol; Yang 2014, Trend Pharmacol Sci). IL-23 is a vital checkpoint in the generation, maintenance and activation of pathogenic Th17 cells. In response to IL-23 signals, RORγt cooperates with a network of transcription factors (STAT3, IRF4 and BATF) to initiate the complete differentiation program of Th17 cells (Gaffen 2014, Nat Rev Immunol).

Th17 cells and IL-17 immune response have been shown to be associated with the pathology of many human inflammatory and autoimmune disorders. Therapeutic strategies targeting the IL-23-IL-17 axis are being developed in many autoimmune diseases, and some of them have already demonstrated to provide clinical efficacy some diseases (Patel 2015; Krueger 2018 Exp Dermatol).

There is thus evidence that RORα, RORβ and RORγ play a role in the pathogenesis of many diseases.

It would be desirable to provide compounds that modulate the activity of RORα and/or RORγ for use in treating inflammatory, metabolic and autoimmune diseases.

WO2016020288 and WO2016020295 describe compounds that modulate the activity or RORgamma receptors. However, a need still exists for potent RORgamma modulators having improved physicho-chemical properties.

SUMMARY

In one aspect provided herein are compounds of Formula (I)

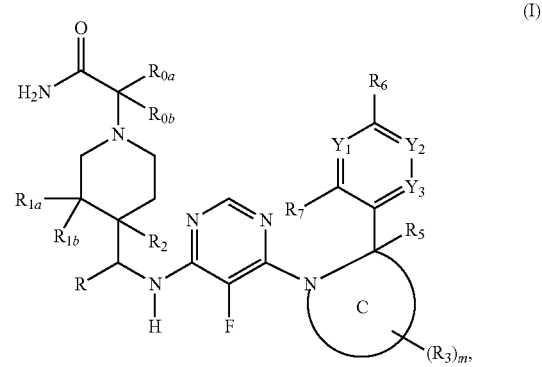

a stereoisomer thereof, or a pharmaceutically acceptable salt of the compound or stereoisomer, wherein:
$Y_1$, $Y_2$ and $Y_3$ are independently —N— or —$CR_8$—;
m is independently selected from 0, 1, and 2;
R is selected from the group consisting of hydrogen, $C_{1-6}$ alkyl and $C_{1-4}$ hydroxyalkyl;
$R_{0a}$ and $R_{0b}$ independently are selected from the group consisting of hydrogen, $C_{1-4}$ alkyl, $C_{1-4}$ hydroxyalkyl, and $C_{1-4}$ haloalkyl;
$R_{1a}$ and $R_{1b}$ are independently selected from the group consisting of hydrogen, hydroxyl, halogen, amino, $C_{1-4}$ alkyl, $C_{1-4}$ hydroxyalkyl, and $C_{1-4}$ haloalkyl;

$R_2$ is selected from the group consisting of hydrogen, hydroxyl, amino, cyano, halogen, $C_{1-4}$ alkyl, $C_{1-4}$ haloalkyl, $C_{1-4}$ hydroxyalkyl, —C(=O)NH$_2$, —C(=O)OH, —C(=O)O—$C_{1-4}$ alkyl, and substituted or unsubstituted heteroaryl;

Ring C is a 3 to 10 membered heteroalicyclyl ring system containing 0, 1, or 2 heteroatoms independently selected from N, O and S in addition to one N atom shown in the C ring in the compound of Formula I;

Each $R_3$ is independently selected from the group consisting of hydrogen, halogen, hydroxyl, $C_{1-4}$ alkyl, $C_{1-4}$ haloalkyl, $C_{1-4}$ hydroxyalkyl; and $C_{1-4}$ hydroxyhaloalkyl;

$R_5$ is absent, hydrogen or $C_{1-4}$ alkyl;

$R_6$ is selected from the group consisting of hydrogen, —CN, halogen, $C_{1-4}$ alkyl, $C_{1-4}$ haloalkyl, $C_{1-4}$ hydroxyalkyl, $C_{1-4}$ hydroxyhaloalkyl, $C_{1-4}$ alkoxy, $C_{1-4}$ haloalkoxy, substituted or unsubstituted heteroaryl;

$R_7$ is selected from the group consisting of hydrogen, hydroxyl, —CN, halogen, $C_{1-4}$ alkyl, $C_{1-4}$ haloalkyl, $C_{1-4}$ hydroxyalkyl, $C_{1-4}$ alkoxy, $C_{1-4}$ haloalkoxy;

each $R_8$ is independently selected from the group consisting of hydrogen, hydroxyl, —CN, halogen, $C_{1-4}$ alkyl, $C_{1-4}$ haloalkyl, $C_{1-4}$ hydroxy alkyl, $C_{1-4}$ alkoxy, and $C_{1-4}$ haloalkoxy;

and whenever $R_7$ is hydrogen and each $R_8$ present is hydrogen, then $R_6$ is selected from the group consisting of —CN, halogen, $C_{1-4}$ alkyl, $C_{1-4}$ haloalkyl, $C_{1-4}$ hydroxyalkyl, $C_{1-4}$ hydroxyhaloalkyl, $C_{1-4}$ alkoxy, $C_{1-4}$ haloalkoxy, substituted or unsubstituted heteroaryl, and wherein when substituted, a heteroaryl is substituted with 1 to 3 groups independently selected from the group consisting of $C_{1-4}$ alkyl, $C_{1-4}$ hydroxyalkyl, $C_{2-4}$ alkenyl, $C_{2-4}$ alkynyl, hydroxy, $C_{1-4}$ alkoxy, cyano, halogen, $C_{1-4}$ haloalkyl, $C_{1-4}$ haloalkoxy and $C_{1-6}$ hydroxyhaloalkyl.

In one aspect provided herein are pharmaceutical compositions comprising a compound of Formula (I) or a stereoisomer thereof, or a pharmaceutically acceptable salt of the compound or stereoisomer of Formula (I) and at least one pharmaceutical acceptable excipient.

In one aspect provided herein are compounds of Formula (I) or a stereoisomer thereof, or a pharmaceutically acceptable salt of the compound or stereoisomer of Formula (I), or pharmaceutical compositions thereof for use in treatment and/or prevention of a disease or disorder or a symptom thereof selected from the group consisting of asthma, acne, chronic obstructive pulmonary disease (COPD), bronchitis, atherosclerosis, *Helicobacter pylori* infection, allergic diseases including allergic rhinitis, allergic conjunctivitis and uveitis, sprue and food allergy, atopic dermatitis, lichen planus, cystic fibrosis, lung allograph rejection, multiple sclerosis, rheumatoid arthritis, juvenile idiopathic arthritis, osteoarthritis, ankylosing spondylitis, psoriasis, psoriatic arthritis, ichthyoses, bullous diseases, hidradenitis suppurativa, steatosis, steatohepatitis, non-alcoholic fatty liver disease (NAFLD), non-alcoholic steatohepatitis (NASH), lupus erythematosus, Hashimoto's disease, pancreatitis, autoimmune diabetes, autoimmune ocular disease, ulcerative colitis, colitis, Crohn's disease, inflammatory bowel disease (IBD), inflammatory bowel syndrome (IBS), Sjogren's syndrome, optic neuritis, type I diabetes, neuromyelitis optica, Myastehnia Gravis, Guillain-Barre syndrome, Graves' disease, scleritis, obesity, obesity-induced insulin resistance, type II diabetes, and cancer.

Further, advantageous features of various embodiments are defined in the dependent claims and within the detailed description below.

DETAILED DESCRIPTION OF PREFERRED EMBODIMENTS

Definitions

Unless defined otherwise, all technical and scientific terms used herein have the same meaning as is commonly understood by one of ordinary skill in the art. All patents, applications, published applications and other publications referenced herein are incorporated by reference in their entirety. In the event that there are a plurality of definitions for a term herein, those in this section prevail unless stated otherwise.

As used herein, any "R" group(s) such as, without limitation, R, $R_1$, $R_2$, $R_3$, $R_4$, $R_5$, $R_6$, $R_7$, $R_8$, $R_9$, and $R_{10}$, represent substituents that can be attached to the indicated atom. Examples of R groups includes but is not limited to hydrogen, hydroxy, alkyl, alkenyl, alkynyl, alkoxy, cycloalkyl, cycloalkenyl, cycloalkynyl, aryl, heteroaryl, and heteroalicyclyl. If two "R" groups are covalently bonded to the same atom or to adjacent atoms, then they may be "taken together" or "combined" as defined herein to form a cycloalkyl, aryl, heteroaryl or heteroalicyclyl group. For example, without limitation, if $R_a$ and $R_b$ of an $NR_aR_b$ group are indicated to be "taken together" or "combined", it means that they are covalently bonded to one another at their terminal atoms to form a ring that includes the nitrogen:

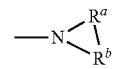

As readily recognized by the skilled person, any given group disclosed herein may comprise further hydrogen(s) than the one(s) provided by a R-group, being hydrogen, attached to the group.

Whenever a group is described as being "unsubstituted or substituted," if substituted, the substituent(s) (which may be present one or more times, such as 1, 2, 3 or 4 times) are independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, carbonyl, thiocarbonyl, C-amido, N-amido, S-sulfonamido, N-sulfonamido, nitro, silyl, sulfenyl, sulfinyl, sulfonyl, haloalkyl, hydroxyalkyl, haloalkoxy, trihalomethanesulfonyl, trihalomethanesulfonamido, and amino, including mono- and di-substituted amino groups, and the protected derivatives thereof. When a substituent on a group is deemed to be "substituted," the substitutent itself is substituted with one or more of the indicated substitutents. When the referenced substituent is substituted, it is meant that one or more hydrogen atoms on the referenced substituent may be replaced with a group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, carbonyl, thiocarbonyl, C-amido, N-amido, S-sulfonamido, N-sulfonamido, nitro, silyl, sulfenyl, sulfinyl, sulfonyl, haloalkyl, hydroxyalkyl, haloalkoxy, trihalomethanesulfonyl, trihalomethanesulfonamido, and amino, including mono- and di-substituted amino groups, and the protected derivatives thereof. The protecting groups that may form the protective derivatives of the above substituents are known to those of skill in the art and may be found in references Greene and Wuts, Protective Groups in Organic Synthesis, 3rd Ed., John Wiley & Sons, New York, N.Y., 1999, which is hereby incorporated by reference in its entirety.

As used herein, "$C_m$ to $C_n$," "$C_m$-$C_n$" or "$C_{m-n}$" in which "m" and "n" are integers refers to the number of carbon atoms in the relevant group. That is, the group can contain from "m" to "n", inclusive, carbon atoms. Thus, for example, a "$C_1$ to $C_6$ alkyl" group refers to all alkyl groups having from 1 to 6 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$—, $CH_3CH(CH)_3CH_2$—, $CH_3CH(CH)_3CH_2$— and $(CH_3)_3C$—. If no "m" and "n" are designated with regard to a group, the broadest range described in these definitions is to be assumed.

As used herein, "alkyl" refers to a straight or branched hydrocarbon chain group that is fully saturated (no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms, such as "$C_{1-6}$". The alkyl group could also be a lower alkyl having 1 to 4 carbon atoms. The alkyl group of the compounds may be designated as "$C_1$-$C_4$ alkyl," "$C_{1-4}$ alkyl" or similar designations. By way of example only, "$C_1$-$C_4$ alkyl" or "$C_{1-4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like. When substituted, the substituent group(s) is(are) one or more group(s) individually and independently selected from alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, carbonyl, thiocarbonyl, C-amido, N-amido, S-sulfonamido, N-sulfonamido, nitro, silyl, sulfenyl, sulfinyl, sulfonyl, haloalkyl, hydroxyalkyl, haloalkoxy, trihalomethanesulfonyl, trihalomethanesulfonamido, and amino, including mono- and di-substituted amino groups, and the protected derivatives thereof.

As used herein, "alkenyl" refers to an alkyl group that contains in the straight or branched hydrocarbon chain one or more double bonds. If more than one double bond is present, the double bonds may be conjugated or not conjugated. The alkenyl group may have 2 to 20 carbon atoms (whenever it appears herein, a numerical range such as "2 to 20" refers to each integer in the given range; e.g., "2 to 20 carbon atoms" means that the alkenyl group may consist of 2 carbon atoms, 3 carbon atoms, 4 carbon atoms, etc., up to and including 20 carbon atoms, although the present definition also covers the occurrence of the term "alkenyl" where no numerical range is designated). When substituted, the substituent group(s) is(are) one or more group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, mercapto, alkylthio, cyano, halogen, nitro, haloalkyl, hydroxyalkyl, haloalkoxy, and amino, including mono- and di-substituted amino groups, and the protected derivatives thereof.

As used herein, "alkynyl" refers to an alkyl group that contains in the straight or branched hydrocarbon chain one or more triple bonds. The alkynyl group may have 2 to 20 carbon atoms (whenever it appears herein, a numerical range such as "2 to 20" refers to each integer in the given range; e.g., "2 to 20 carbon atoms" means that the alkynyl group may consist of 2 carbon atoms, 3 carbon atoms, 4 carbon atoms, etc., up to and including 20 carbon atoms, although the present definition also covers the occurrence of the term "alkynyl" where no numerical range is designated). An alkynyl group may be unsubstituted or substituted. When substituted, the substituent(s) may be selected from the same groups disclosed above with regard to alkenyl group substitution.

As used herein, "hetero" may be attached to a group and refers to one or more carbon atom(s) and the associated hydrogen atom(s) in the attached group have been independently replaced with the same or different heteroatoms selected from nitrogen, oxygen, phosphorus and sulfur.

As used herein, "heteroalkyl," by itself or in combination with another term, refers to a straight or branched alkyl group consisting of the stated number of carbon atoms, where one or more carbon atom(s), such as 1, 2, 3 or 4 carbon atom(s), and the associated hydrogen atom(s) have been independently replaced with the same or different heteroatoms selected from nitrogen, oxygen and sulfur. The carbon atom(s) being replaced may be in the middle or at the end of the alkyl group. Examples of heteroalkyl include $C_{1-6}$ heteroalkyl wherein one or more of the carbon atom(s) has been replaced by a heteroatom selected from the group consisting of nitrogen, oxygen and sulfur, examples are, —S-alkyl, —O-alkyl, —NH-alkyl, -alkylene-O-alkyl, etc. A heteroalkyl may be substituted.

As used herein, "aryl" refers to a carbocyclic (all carbon) ring or two or more fused rings (rings that share two adjacent carbon atoms) that have a fully delocalized pi-electron system. In some embodiments described herein the aryl group is a $C_{1-10}$ aryl, which may be substituted or unsubstituted. Examples of aryl groups include, but are not limited to, benzene, naphthalene and azulene. An aryl group may be substituted. When substituted, hydrogen atoms are replaced by substituent group(s) that is(are) one or more group(s) independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, carbonyl, thiocarbonyl, C-amido, N-amido, S-sulfonamido, N-sulfonamido, nitro, silyl, sulfenyl, sulfinyl, sulfonyl, haloalkyl, hydroxyalkyl, haloalkoxy, trihalomethanesulfonyl, trihalomethanesulfonamido, and amino, including mono- and di-substituted amino groups, and the protected derivatives thereof. When substituted, substituents on an aryl group may form a non-aromatic ring fused to the aryl group, including a cycloalkyl, cycloalkenyl, cycloalkynyl, and heterocyclyl.

As used herein, "heteroaryl" refers to a monocyclic or multicyclic aromatic ring system (a ring system with fully delocalized pi-electron system), in which at least one of the atoms in the ring system is a heteroatom, that is, an element other than carbon, including but not limited to, nitrogen, oxygen and sulfur. In some embodiments described herein the heteroaryl includes, but is not limited to, $C_{6-10}$ heteroaryl, wherein one to four carbon atoms is/are replaced by one to four heteroatoms independently selected from the group consisting of nitrogen, oxygen and sulfur. Examples of monocyclic "heteroaryl" include, but are not limited to, furan, thiophene, phthalazine, pyrrole, oxazole, oxadiazole, thiazole, imidazole, pyrazole, isoxazole, isothiazole, triazole, thiadiazole, pyridine, pyridazine, pyrimidine, pyrazine, tetrazole, and triazine. Examples of multicyclic "heteroaryl" include, but are not limited to, quinoline, isoquinoline, quinazoline, quinoxaline, indole, purines, benzofuran, benzothiophene, benzopyranones (e.g. coumarin, chromone, and isocoumarin). A heteroaryl may be substituted. When substituted, hydrogen atoms are replaced by substituent group(s) that is(are) one or more group(s) independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, carbonyl, thiocarbonyl, C-amido, N-amido, S-sulfonamido, N-sulfonamido, nitro, silyl, sulfenyl, sulfinyl, sulfonyl, haloalkyl, hydroxyalkyl, haloalkoxy, trihalomethanesulfonyl, trihalomethanesulfonamido, and amino, including mono- and di-substituted amino groups, and the protected derivatives thereof. When substituted, substituents on a heteroayl group may form a non-aromatic ring fused to the aryl group, including a cycloalkyl, cycloalkenyl, cycloalkynyl, and heterocyclyl.

An "aralkyl" or "arylalkyl" is an aryl group connected, as a substituent, via an alkylene group. The alkylene and aryl group of an aralkyl may be substituted. Examples include but are not limited to benzyl, substituted benzyl, 2-phenylethyl, 3-phenylpropyl, and naphthylalkyl. In some cases, the alkylene group is a lower alkylene group.

A "heteroaralkyl" or "heteroarylalkyl" is heteroaryl group connected, as a substituent, via an alkylene group. The alkylene and heteroaryl group of heteroaralkyl may be substituted. Examples include but are not limited to 2-thienylmethyl, 3-thienylmethyl, furylmethyl, thienylethyl, pyrrolylalkyl, pyridylalkyl, isoxazolylalkyl, pyrazolylalkyl and imidazolylalkyl, and their substituted as well as benzo-fused analogs. In some cases, the alkylene group is a lower alkylene group.

An "alkylene" is a straight-chained tethering group, forming bonds to connect molecular fragments via their terminal carbon atoms. The alkylene may have 1 to 20 carbon atoms. The alkylene may also be a medium size alkylene having 1 to 10 carbon atoms, such as "$C_{1-6}$" The alkylene could also be a lower alkylene having 1 to 4 carbon atoms. The alkylene may be designated as "$C_1$-$C_4$ alkylene", "$C_{1-4}$ alkylene" or similar designations. Non-limiting examples include, methylene (—$CH_2$—), ethylene (—$CH_2CH_2$—), propylene (—$CH_2CH_2CH_2$—), and butylene (—$(CH_2)_4$—) groups. In the case of methylene, the two connected fragments are connected to the same carbon atom. A lower alkylene group may be substituted.

As used herein, "heteroalkylene" by itself or in combination with another term refers to an alkylene group consisting of the stated number of carbon atoms in which one or more of the carbon atoms, such as 1, 2, 3 or 4 carbon atom(s), are independently replaced with the same or different heteroatoms selected from oxygen, sulfur and nitrogen. Examples of heteroalkylene include, but not limited to —$CH_2$—O—, —$CH_2$—$CH_2$—O—, —$CH_2$—$CH_2$—$CH_2$—O—, —$CH_2$—NH—, —$CH_2$—$CH_2$—NH—, —$CH_2$—$CH_2$—$CH_2$—NH—, $CH_2$—$CH_2$—NH—$CH_2$—, —O—$CH_2$—$CH_2$—O—$CH_2$—$CH_2$—O—, —O—$CH_2$—$CH_2$—O—$CH_2$—$CH_2$—, and the like.

As used herein, "alkylidene" refers to a divalent group, such as =CR'R", which is attached to one carbon of another group, forming a double bond. Alkylidene groups include, but are not limited to, methylidene (=$CH_2$) and ethylidene (=$CHCH_3$). As used herein, "arylalkylidene" refers to an alkylidene group in which either R' or R" is an aryl group. An alkylidene group may be substituted.

As used herein, "alkoxy" refers to the group —OR wherein R is an alkyl, e.g. methoxy, ethoxy, n-propoxy, cyclopropoxy, 1-methylethoxy (isopropoxy), n-butoxy, isobutoxy, sec-butoxy, tert-butoxy, amoxy, tert-amoxy and the like. An alkoxy may be substituted.

As used herein, "alkylthio" refers to the formula —SR wherein R is an alkyl is defined as above, e.g. methylmercapto, ethylmercapto, n-propylmercapto, 1-methylethylmercapto (isopropylmercapto), n-butylmercapto, iso-butylmercapto, sec-butylmercapto, tert-butylmercapto, and the like. An alkylthio may be substituted.

As used herein, "aryloxy" and "arylthio" refers to RO- and RS-, in which R is an aryl as defined above, e.g., phenoxy, naphthalenyloxy, azulenyloxy, anthracenyloxy, naphthalenylthio, phenylthio and the like. Both an aryloxy and arylthio may be substituted.

As used herein, "alkenyloxy" refers to the formula —OR wherein R is an alkenyl as defined above, e.g., vinyloxy, propenyloxy, n-butenyloxy, iso-butenyloxy, sec-pentenyloxy, tert-pentenyloxy, and the like. The alkenyloxy may be substituted.

As used herein, "acyl" refers to a hydrogen, alkyl, alkenyl, alkynyl, or aryl connected, as substituents, via a carbonyl group. Examples include formyl, acetyl, propanoyl, benzoyl, and acryl. An acyl may be substituted.

As used herein, "cycloalkyl" refers to a completely saturated (no double bonds) mono- or multi-cyclic hydrocarbon ring system. When composed of two or more rings, the rings may be joined together in a fused, bridged or spiro-connected fashion. Cycloalkyl groups may range from $C_3$ to $C_{10}$, such as from $C_3$ to $C_6$. A cycloalkyl group may be unsubstituted or substituted. Typical cycloalkyl groups include, but are in no way limited to, cyclopropyl, cyclobutyl, cyclopentyl, cyclohexyl, and the like. If substituted, the substituent(s) may be an alkyl or selected from those indicated above with regard to substitution of an alkyl group unless otherwise indicated. When substituted, substituents on a cycloalkyl group may form an aromatic ring fused to the cycloalkyl group, including an aryl and a heteroaryl.

As used herein, "cycloalkenyl" refers to a cycloalkyl group that contains one or more double bonds in the ring although, if there is more than one, they cannot form a fully delocalized pi-electron system in the ring (otherwise the group would be "aryl," as defined herein). When composed of two or more rings, the rings may be connected together in a fused, bridged or spiro-connected fashion. Cycloalkenyl groups may range from $C_3$ to $C_{10}$, such as from $C_3$ to $C_8$ or from $C_5$ to $C_{10}$. For example, $C_{3-8}$ cycloalkenyl includes $C_{4-8}$ cycloalkenyl, $C_{5-8}$ cycloalkenyl or $C_{6-8}$ cycloalkenyl. A cycloalkenyl group may be unsubstituted or substituted. When substituted, the substituent(s) may be an alkyl or selected from the groups disclosed above with regard to alkyl group substitution unless otherwise indicated. When substituted, substituents on a cycloalkenyl group may form an aromatic ring fused to the cycloalkenyl group, including an aryl and a heteroaryl.

As used herein, "cycloalkynyl" refers to a cycloalkyl group that contains one or more triple bonds in the ring. When composed of two or more rings, the rings may be joined together in a fused, bridged or spiro-connected fashion. Cycloalkynyl groups may range from $C_8$ to $C_{12}$. A cycloalkynyl group may be unsubstituted or substituted.

When substituted, the substituent(s) may be an alkyl or selected from the groups disclosed above with regard to alkyl group substitution unless otherwise indicated. When substituted, substituents on a cycloalkynyl group may form an aromatic ring fused to the cycloalkynyl group, including an aryl and a heteroaryl.

As used herein, "heteroalicyclic" or "heteroalicyclyl" refers to a 3- to 18 membered ring which consists of carbon atoms and from one to five heteroatoms selected from the group consisting of nitrogen, oxygen and sulfur. The heteroalicyclic or heteroalicyclyl groups may range from $C_2$ to $C_{10}$, in some embodiments it may range from $C_2$ to $C_9$, and in other embodiments it may range from $C_2$ to $C_8$. In some embodiments The "heteroalicyclic" or "heteroalicyclyl" may be monocyclic, bicyclic, tricyclic, or tetracyclic ring system, which may be joined together in a fused, bridged or spiro-connected fashion; and the nitrogen, carbon and sulfur atoms in the "heteroalicyclic" or "heteroalicyclyl" may be oxidized; the nitrogen may be quaternized; and the rings may also contain one or more double bonds provided that they do not form a fully delocalized pi-electron system throughout all the rings, examples are 2H-benzo[b][1,4]oxazin-3(4H)-one, 3,4-dihydroquinolin-2(1H)-one, 1,2,3,4-tetrahydroquinoline, 3,4-dihydro-2H-benzo[b][1,4]oxazine, 2,3-dihydrobenzo[d]oxazole, 2,3-dihydro-1H-benzo[d]imidazole, indoline, and 1,3-dihydro-2H-benzo[d]imidazol-2-one, and benzo[d]oxazol-2(3H)-one. Heteroalicyclyl groups may be unsubstituted or substituted. When substituted, the substituent(s) may be one or more groups independently selected from the group consisting of alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, oxo, alkoxy, aryloxy, acyl, ester, O-carboxy, mercapto, alkylthio, arylthio, cyano, halogen, C-amido, N-amido, S-sulfonamido, N-sulfonamido, isocyanato, thiocyanato, isothiocyanato, nitro, silyl, haloalkyl, hydroxyalkyl, haloalkoxy, trihalomethanesulfonyl, trihalomethanesulfonamido, and amino, including mono- and di-substituted amino groups, and the protected derivatives thereof. Examples of such "heteroalicyclic" or "heteroalicyclyl" include but are not limited to, azepinyl, dioxolanyl, imidazolinyl, morpholinyl, oxetanyl, oxiranyl, piperidinyl N-Oxide, piperidinyl, piperazinyl, pyrrolidinyl, pyranyl, 4-piperidonyl, pyrazolidinyl, 2-oxopyrrolidinyl, tetrahydrofuranyl, tetrahydropyranyl, thiamorpholinyl, thiamorpholinyl sulfoxide, and thiamorpholinyl sulfone. When substituted, substituents on a heteroalicyclyl group may form an aromatic ring fused to the heteroalicyclyl group, including an aryl and a heteroaryl.

A "(cycloalkyl)alkyl" is a cycloalkyl group connected, as a substituent, via an alkylene group. The alkylene and cycloalkyl of a (cycloalkyl)alkyl may be substituted. Examples include but are not limited cyclopropylmethyl, cyclobutylmethyl, cyclopropylethyl, cyclopropylbutyl, cyclobutylethyl, cyclopropylisopropyl, cyclopentylmethyl, cyclopentylethyl, cyclohexylmethyl, cyclohexylethyl, cycloheptylmethyl, and the like. In some cases, the alkylene group is a lower alkylene group.

A "(cycloalkenyl)alkyl" is a cycloalkenyl group connected, as a substituent, via an alkylene group. The alkylene and cycloalkenyl of a (cycloalkenyl)alkyl may be substituted. In some cases, the alkylene group is a lower alkylene group.

A "(cycloalkynyl)alkyl" is a cycloalkynyl group connected, as a substituent, via an alkylene group. The alkylene and cycloalkynyl of a (cycloalkynyl)alkyl may be substituted. In some cases, the alkylene group is a lower alkylene group.

As used herein, "halo" or "halogen" refers to F (fluoro), Cl (chloro), Br (bromo) or I (iodo).

As used herein, "haloalkyl" refers to an alkyl group in which one or more of the hydrogen atoms are replaced by halogen. Such groups include but are not limited to, chloromethyl, fluoromethyl, difluoromethyl, trifluoromethyl and 1-chloro-2-fluoromethyl, 2-fluoroisobutyl. A haloalkyl may be substituted or unsubstituted, and some embodiments relate to a medium size haloalkyl having 1 to 10 carbon atoms, such as $C_{1-6}$ haloalkyl.

As used herein, "haloalkoxy" refers to a RO-group in which R is a haloalkyl group. Such groups include but are not limited to, chloromethoxy, fluoromethoxy, difluoromethoxy, trifluoromethoxy and 1-chloro-2-fluoromethoxy, 2-fluoroisobutyoxy. A haloalkoxy may be substituted.

As used herein, the term hydroxyalkyl refers to an alkyl group in which one of more of the hydrogen atoms are replaced by a hydroxyl group. Such groups include but are not limited to hydroxymethyl, hydroxyethyl, hydroxypropyl, hydroxybutyl, hydroxypentyl and hydroxyhexyl. A hydroxyalkyl group may be substituted or unsubstituted, and some embodiments relate to a medium size hydroxyalkyl having 1 to 10 carbon atoms, such as $C_{1-6}$ hydroxy alkyl.

An "O-carboxy" group refers to a "RC(=O)O—" group in which R can be hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined herein. An O-carboxy may be substituted.

A "C-carboxy" group refers to a "—C(=O)OR" group in which R can be the same as defined with respect to O-carboxy. A C-carboxy may be substituted.

A "trihalomethanesulfonyl" group refers to an "$X_3CSO_2$—" group" wherein X is a halogen.

A dashed bond, ----- represents an optional unsaturation between the atoms forming the bond. This bond may be unsaturated (e.g. C=C, C=N, C=O) or saturated (e.g. C—C, C—N, C—O). When a dashed bond is present in a ring system it may form part of an aromatic ring system.

As used herein, a straight (unwedged) bolded or hashed bond, ▬ or ׳׳׳׳׳׳, refers to relative stereochemistry inclusive of all possible stereoisomers at that position.

As used herein, and unless otherwise indicated, a wedged-bond (bolded, hashed, or otherwise), ▬, ◄, or ׳׳׳׳׳, refers to absolute stereochemistry referring to the particular stereoisomer as depicted that position.

A "nitro" group refers to a "—$NO_2$" group.
A "cyano" group refers to a "—CN" group.
A "cyanato" group refers to an "—OCN" group.
An "isocyanato" group refers to a "—NCO" group.
A "thiocyanato" group refers to a "—SCN" group.
A "carbonyl" group refers to a "—C(=O)—" group.
A "thiocarbonyl" group refers to a "—C(=S)—" group.
An "oxo" group refers to a "=O" group.
A "hydroxy" group or "hydroxyl" group refers to an "—OH" group.
An "isothiocyanato" group refers to an "—NCS" group.
A "sulfinyl" group refers to an "—S(=O)—R" group in which R can be the same as defined with respect to O-carboxy. A sulfinyl may be substituted.

A "sulfonyl" group refers to an "$SO_2R$" group in which R can be the same as defined with respect to O-carboxy. A sulfonyl may be substituted.

An "S-sulfonamido" group refers to a "—$SO_2NR_AR_B$" group in which $R_A$ and $R_B$ independently of each other can be the same as defined with respect to the R group as defined for O-carboxy, or combined to form a ring system selected from the group consisting of substituted or unsubstituted $C_{3-8}$ cycloalkyl, substituted or unsubstituted $C_{3-8}$ cycloalkenyl, substituted or unsubstituted $C_{3-8}$ cycloalkyl, substituted or unsubstituted $C_{3-8}$ cycloalkenyl substituted or unsubstituted heteroalicyclyl, substituted or unsubstituted aryl, and substituted or unsubstituted heteroaryl. A S-sulfonamido may be substituted.

An "N-sulfonamido" group refers to a "$RSO_2N(R_A)$—" group in which R and $R_A$ independently of each other can be the same as defined with respect to the R group as defined for O-carboxy. An N-sulfonamido may be substituted.

A "trihalomethanesulfonamido" group refers to an "$X_3CSO_2N(R)$—" group with X as halogen and R can be the same as defined with respect to O-carboxy. A trihalomethanesulfonamido may be substituted.

A "C-amido" group refers to a "—C(=O)$NR_AR_B$" group in which $R_A$ and $R_B$ independently of each other can be the same as defined with respect to the R group as defined for O-carboxy, or combined to form a ring system selected from the group consisting of substituted or unsubstituted $C_{3-8}$ cycloalkyl, substituted or unsubstituted $C_{3-8}$ cycloalkenyl, substituted or unsubstituted $C_{3-8}$ cycloalkyl, substituted or unsubstituted $C_{3-8}$ cycloalkenyl substituted or unsubstituted heteroalicyclyl, substituted or unsubstituted aryl, and substituted or unsubstituted heteroaryl. A C-amido may be substituted.

An "N-amido" group refers to a "RC(=O)$NR_A$—" group in which R and $R_A$ independently of each other can be the same as defined with respect to the R group as defined for O-carboxy. An N-amido may be substituted.

An "ester" refers to a "—C(=O)OR" group in which R can be the same as defined with respect to O-carboxy. An ester may be substituted.

A lower alkoxyalkyl refers to an alkoxy group connected via a lower alkylene group. A lower alkoxyalkyl may be substituted.

An "amine" or "amino" refers to "$RNH_2$" (a primary amine), "$R_2NH$" (a secondary amine), "$R_3N$" (a tertiary amine). An amino group may be substituted.

A lower aminoalkyl refers to an amino group connected via a lower alkylene group. A lower aminoalkyl may be substituted.

Any unsubstituted or monosubstituted amine group on a compound herein can be converted to an amide, any hydroxyl group can be converted to an ester and any carboxyl group can be converted to either an amide or ester using techniques well-known to those skilled in the art (see, for example, Greene and Wuts, Protective Groups in Organic Synthesis, $3^{rd}$ Ed., John Wiley & Sons, New York, N.Y., 1999).

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

List of Abbreviations

DMF dimethylformamide
DMSO dimethylsulfoxide
MeOH methanol
EtOH ethanol
THF tetrahydrofurane
DCM dichloromethane, methylene chloride
DCE 1,2-dichloroethane
LRMS low resolution mass spectrometry
HPLC high pressure liquid chromatography
Prep-HPLC preparative high pressure liquid chromatography
h hour
min minutes
EA ethyl acetate
EDC. HCl 3-((ethylimino)methyleneamino)-N,N-dimethylpropan-1-aminium chloride
DIEA diisopropylethyamine
TEA triethylamine
TFA trifluoroacetic acid
HCl hydrochloric acid, hydrogen chloride
HOBt 1-hydroxybenzotriazole hydrate
HOAt 1-hydroxy-7-azabenzotriazole
HATU 1-[bis(dimethylamino)methylene]-1H-1,2,3-triazolo[4,5-b]pyridinium 3-oxid hexafluorophosphate
DMAP 4-(dimethylamino)pyridine
DAST (diethylamino)sulfur trifluoride
DMP Dess-Martin Periodinane, 1,1,1-tris(acetyloxy)-1,1-dihydro-1,2-benziodoxol-3-(1H)-one
TBAF tetrabutylammonium fluoride trihydrate
TBDMSCl tert-butyldimethylsilyl chloride
MsCl methanesulfonyl chloride
NAS nucleophilic aromatic substitution
nBuLi n-Butyllithium
iPr isopropyl
Boc tert-Butyloxycarbonyl
Flash CC Flash Column Chromatography
on overnight
rt room temperature
aq aqueous
ND Not Determined
Cbz Carboxybenzyl
Hex hexane
Hept heptane
DEA diethylamine
PE petroleum ether
DAD Diode Array Detector
TOF Time of Flight
IPA isopropanol
Pg Protective group It is understood that, in any compound disclosed herein having one or more chiral centers, if an absolute stereochemistry is not expressly indicated, then each center may independently be of R-configuration or S-configuration or a mixture thereof. Thus, the compounds provided herein may be enantiomeric ally pure or be stereoisomeric mixtures. Further, compounds provided herein may be scalemic mixtures. In addition, it is understood that in any compound having one or more double bond(s) generating geometrical isomers that can be defined as E or Z each double bond may independently be E or Z or a mixture thereof. Likewise, all tautomeric forms are also intended to be included.

As used herein, the term "rac" refers to "racemic", "racemate", etc., as is understood by one of ordinary skill in the art. For example, a racemate comprises a mixture of enantiomers of a chiral molecule in equivalent amounts. Typically, a racemate does not exhibit optical activity.

As used herein, the term "rel" refers to the relative, but not absolute, configuration of a stereogenic center with respect to any other stereogenic center within the same compound, as is understood by one of ordinary skill in the art.

As used herein, "tautomer" and "tautomeric" refer to alternate forms of a compound disclosed herein that differ in the position of a proton. Non-limiting examples include enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

It is understood that isotopes may be present in the compounds described herein. Each chemical element as represented in a compound structure may include any isotope of said element. For example, in a compound described herein a hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

As used herein, reference to an element, whether by description or chemical structure, encompasses all isotopes of that element unless otherwise described. By way of example, the term "hydrogen" or "H" in a chemical structure as used herein is understood to encompass, for example, not only $^1$H, but also deuterium ($^2$H), tritium ($^3$H), and mixtures thereof unless otherwise denoted by use of a specific isotope. Other specific non-limiting examples of elements for which isotopes are encompassed include carbon, phosphorous, iodine, and fluorine.

As used herein, "pharmaceutically acceptable salt" refers to a salt of a compound that does not abrogate the biological activity and properties of the compound. Pharmaceutical salts can be obtained by reaction of a compound disclosed herein with an acid or base. Base-formed salts include, without limitation, ammonium salt ($NH_4^+$); alkali metal, such as, without limitation, sodium or potassium, salts; alkaline earth, such as, without limitation, calcium or magnesium, salts; salts of organic bases such as, without limitation, dicyclohexylamine, piperidine, piperazine, methylpiperazine, N-methyl-D-glucamine, diethylamine, ethylenediamine, tris(hydroxymethyl)methylamine; and salts with the amino group of amino acids such as, without limitation, arginine and lysine. Useful acid-based salts include, without limitation, acetates, adipates, aspartates, ascorbates, benzoates, butyrates, caparate, caproate, caprylate, camsylates, citrates, decanoates, formates, fumarates, gluconates, glutarate, glycolates, hexanoates, laurates, lactates, maleates, nitrates, oleates, oxalates, octanoates, propanoates, palmitates, phosphates, sebacates, succinates, stearates, sulfates, sulfonates, such as methanesulfonates, ethanesulfonates, p-toluenesulfonates, salicylates, tartrates, and tosylates.

Pharmaceutically acceptable solvates and hydrates are complexes of a compound with one or more solvent of water molecules, or 1 to about 100, or 1 to about 10, or one to about 2, 3 or 4, solvent or water molecules.

As used herein, a "prodrug" refers to a compound that may not be pharmaceutically active but that is converted into an active drug upon in vivo administration. The prodrug may be designed to alter the metabolic stability or the transport characteristics of a drug, to mask side effects or toxicity, to improve the flavor of a drug or to alter other characteristics or properties of a drug. Prodrugs are often useful because they may be easier to administer than the parent drug. They may, for example, be bioavailable by oral administration whereas the parent drug is not. The prodrug may also have better solubility than the active parent drug in pharmaceutical compositions. An example, without limitation, of a prodrug would be a compound disclosed herein, which is administered as an ester (the "prodrug") to facilitate absorption through a cell membrane where water solubility is detrimental to mobility but which then is metabolically hydrolyzed to a carboxylic acid (the active entity) once inside the cell where water-solubility is beneficial. A further example of a prodrug might be a short peptide (polyaminoacid) bonded to an acid group where the peptide is metabolized in vivo to release the active parent compound. By virtue of knowledge of pharmacodynamic processes and drug metabolism in vivo, those skilled in the art, once a pharmaceutically active compound is known, can design prodrugs of the compound (see, e.g. Nogrady (1985) Medicinal Chemistry A Biochemical Approach, Oxford University Press, New York, pages 388-392).

As used herein, to "modulate" the activity of a receptor means either to activate it, i.e., to increase its cellular function over the base level measured in the particular environment in which it is found, or deactivate it, i.e., decrease its cellular function to less than the measured base level in the environment in which it is found and/or render it unable to perform its cellular function at all, even in the presence of a natural binding partner. A natural binding partner is an endogenous molecule that is an agonist for the receptor.

An "agonist" is defined as a compound that increases the basal activity of a receptor (i.e. signal transduction mediated by the receptor).

As used herein, "partial agonist" refers to a compound that has an affinity for a receptor but, unlike an agonist, when bound to the receptor it elicits only a fractional degree of the pharmacological response normally associated with the receptor even if a large number of receptors are occupied by the compound.

An "inverse agonist" is defined as a compound, which reduces, or suppresses the basal activity of a receptor, such that the compound is not technically an antagonist but, rather, is an agonist with negative intrinsic activity.

As used herein, "antagonist" refers to a compound that binds to a receptor to form a complex that does not give rise to any response, as if the receptor was unoccupied. An antagonist attenuates the action of an agonist on a receptor. An antagonist may bind reversibly or irreversibly, effectively eliminating the activity of the receptor permanently or at least until the antagonist is metabolized or dissociates or is otherwise removed by a physical or biological process.

As used herein, a "subject" refers to an animal that is the object of treatment, observation or experiment. "Animal" includes cold- and warm-blooded vertebrates and invertebrates such as birds, fish, shellfish, reptiles and, in particular, mammals. "Mammal" includes, without limitation, mice; rats; rabbits; guinea pigs; dogs; cats; sheep; goats; cows; horses; primates, such as monkeys, chimpanzees, and apes, and, in particular, humans.

As used herein, a "patient" refers to a subject that is being treated by a medical professional such as an M.D. or a D.V.M. to attempt to cure, or at least ameliorate the effects of, a particular disease or disorder or to prevent the disease or disorder from occurring in the first place.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

A "receptor" is intended to include any molecule present inside or on the surface of a cell that may affect cellular physiology when it is inhibited or stimulated by a ligand. Typically, a receptor comprises an extracellular domain with ligand-binding properties, a transmembrane domain that anchors the receptor in the cell membrane, and a cytoplasmic domain that generates a cellular signal in response to ligand binding ("signal transduction"). A receptor also includes any intracellular molecule that in response to ligation generates a signal. A receptor also includes any molecule having the characteristic structure of a receptor, but with no identifiable ligand. In addition, a receptor includes a truncated, modified, mutated receptor, or any molecule comprising partial or all of the sequences of a receptor.

"Ligand" is intended to include any substance that interacts with a receptor.

"Selective" or "selectivity" is defined as a compound's ability to generate a desired response from a particular receptor type, subtype, class or subclass while generating less or little response from other receptor types. "Selective" or "selectivity" of one or more particular subtypes of a compound means a compound's ability to increase the activity of the subtypes while causing less, little or no increase in the activity of other subtypes.

As used herein, "coadministration" of pharmacologically active compounds refers to the delivery of two or more separate chemical entities, whether in vitro or in vivo. Coadministration means the simultaneous delivery of separate agents; the simultaneous delivery of a mixture of agents; as well as the delivery of one agent followed by delivery of a second agent or additional agents. Agents that are coadministered are typically intended to work in conjunction with each other.

The term "an effective amount" as used herein means an amount of active compound or pharmaceutical agent that elicits the biological or medicinal response in a tissue, system, animal or human that is being sought by a researcher, veterinarian, medical doctor or other clinician, which includes alleviation or palliation of the symptoms of the disease being treated.

When used herein, "prevent/preventing" should not be construed to mean that a condition and/or a disease never might occur again after use of a compound or pharmaceutical composition according to embodiments disclosed herein to achieve prevention. Further, the term should neither be construed to mean that a condition not might occur, at least to some extent, after such use to prevent said condition. Rather, "prevent/preventing" is intended to mean that the condition to be prevented, if occurring despite such use, will be less severe than without such use.

Compounds

In one embodiment the present disclosure relates to a compound of Formula (I)

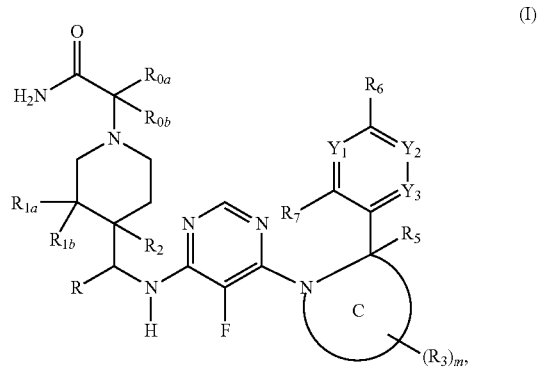

a stereoisomer thereof, or a pharmaceutically acceptable salt of the compound or stereoisomer, wherein $Y_1$, $Y_2$ and $Y_3$ are independently —N— or —$CR_8$—;

m is independently selected from 0, 1, and 2;

R is selected from the group consisting of hydrogen, $C_{1-6}$ alkyl and $C_{1-4}$ hydroxyalkyl;

$R_{0a}$ and $R_{0b}$ independently are selected from the group consisting of hydrogen, $C_{1-4}$ alkyl, $C_{1-4}$ hydroxyalkyl, and $C_{1-4}$ haloalkyl;

$R_{1a}$ and $R_{1b}$ are independently selected from the group consisting of hydrogen, hydroxyl, halogen, amino, $C_{1-4}$ alkyl, $C_{1-4}$ hydroxyalkyl, and $C_{1-4}$ haloalkyl;

$R_2$ is selected from the group consisting of hydrogen, hydroxyl, amino, cyano, halogen, $C_{1-4}$ alkyl, $C_{1-4}$ haloalkyl, $C_{1-4}$ hydroxyalkyl, —C(=O)$NH_2$, —C(=O)OH, —C(=O)O—$C_{1-4}$ alkyl, and substituted or unsubstituted heteroaryl;

Ring C is a 3 to 10 membered heteroalicyclyl ring system containing 0, 1, or 2 heteroatoms independently selected from N, O and S in addition to one N atom shown in the C ring in the compound of Formula I;

Each $R_3$ is independently selected from the group consisting of hydrogen, halogen, hydroxyl, $C_{1-4}$ alkyl, $C_{1-4}$ haloalkyl, $C_{1-4}$ hydroxyalkyl; and $C_{1-4}$ hydroxyhaloalkyl;

$R_5$ is absent, hydrogen or $C_{1-4}$ alkyl;

$R_6$ is selected from the group consisting of hydrogen, —CN, halogen, $C_{1-4}$ alkyl, $C_{1-4}$ haloalkyl, $C_{1-4}$ hydroxyalkyl, $C_{1-4}$ hydroxyhaloalkyl, $C_{1-4}$ alkoxy, $C_{1-4}$ haloalkoxy, substituted or unsubstituted heteroaryl;

$R_7$ is selected from the group consisting of hydrogen, hydroxyl, —CN, halogen, $C_{1-4}$ alkyl, $C_{1-4}$ haloalkyl, $C_{1-4}$ hydroxyalkyl, $C_{1-4}$ alkoxy, $C_{1-4}$ haloalkoxy;

each $R_8$ is independently selected from the group consisting of hydrogen, hydroxyl, —CN, halogen, $C_{1-4}$ alkyl, $C_{1-4}$ haloalkyl, $C_{1-4}$ hydroxy alkyl, $C_{1-4}$ alkoxy, and $C_{1-4}$ haloalkoxy; and whenever $R_7$ is hydrogen and each $R_8$ present is hydrogen, then $R_6$ is selected from the group consisting of —CN, halogen, $C_{1-4}$ alkyl, $C_{1-4}$ haloalkyl, $C_{1-4}$ hydroxyalkyl, $C_{1-4}$ hydroxyhaloalkyl, $C_{1-4}$alkoxy, $C_{1-4}$haloalkoxy, substituted or unsubstituted heteroaryl, and
wherein when substituted, a heteroaryl is substituted with 1 to 3 groups independently selected from the group consisting of $C_{1-4}$ alkyl, $C_{1-4}$ hydroxyalkyl, $C_{2-4}$ alkenyl, $C_{2-4}$ alkynyl, hydroxy, $C_{1-4}$ alkoxy, cyano, halogen, $C_{1-4}$ haloalkyl, $C_{1-4}$ haloalkoxy and $C_{1-6}$ hydroxyhaloalkyl.

In some embodiments disclosed herein, R is hydrogen.

In some embodiments disclosed herein, $R_{0a}$ is selected from the group consisting of hydrogen, methyl, —$CH_2OH$, —$CH_2CH_2OH$, —$CH_2F$, and —$CHF_2$. In some embodiments $R_{0b}$ is selected from the group consisting of hydrogen, $C_{1-4}$ alkyl, $C_{1-4}$ hydroxyalkyl, and $C_{1-4}$ haloalkyl. In other embodiments, $R_{0a}$ is selected from the group consisting of hydrogen, methyl, —$CH_2OH$, —$CH_2CH_2OH$, —$CH_2F$, and —$CHF_2$ and $R_{0b}$ is selected from the group consisting of hydrogen, $C_{1-4}$ alkyl, $C_{1-4}$ hydroxyalkyl, and $C_{1-4}$ haloalkyl. In other embodiments, at least one of $R_{0a}$ and $R_{0b}$ is hydrogen, e.g. $R_{0a}$ is selected from the group consisting of hydrogen, methyl, —$CH_2OH$, —$CH_2CH_2OH$ and $R_{0b}$ is hydrogen. In some embodiments, $R_{0a}$ is hydrogen. In many embodiments $R_{0a}$ and $R_{0b}$ are hydrogen.

In some embodiments disclosed herein, $R_{1a}$ is selected from the group consisting of hydroxyl, fluoro and —$CF_3$ and $R_{1b}$ is selected from the group consisting of hydrogen, fluoro, and methyl, e.g. $R_{1a}$ is hydroxyl or fluoro, and $R_{1b}$ is hydrogen, or fluoro, e.g. both $R_{1a}$ and $R_{1b}$ are fluoro, or $R_{1a}$ is hydroxyl and $R_{1b}$ is hydrogen. In some embodiments, $R_{1a}$ is hydroxyl or fluoro. In many embodiments, $R_{1a}$ is hydroxyl. In many embodiments, $R_{1b}$ is hydrogen.

In some embodiments disclosed herein, $R_2$ is selected from the group consisting of hydrogen, halogen, hydroxyl, cyano, methyl, ethyl, —$CH_2OH$, —$CH_2CH_2OH$ and —$C(=O)O$—$C_{1-2}$ alkyl, e.g. hydrogen, fluoro, hydroxyl, methyl, —$CH_2OH$, and —$C(=O)OCH_3$. In some embodiments, $R_2$ is selected from the group consisting of hydrogen, fluoro and hydroxyl, e.g. hydroxyl.

In some embodiments, at least one of $R_{1a}$, $R_{1b}$ and $R_2$ is a substituent other than hydrogen. In some embodiments, two of $R_{1a}$, $R_{1b}$ and $R_2$ are a substituent other than hydrogen, e.g. $R_{1a}$ and $R_{1b}$ are fluoro, or $R_{1a}$ is hydroxyl and $R_2$ is hydroxyl. In some embodiments, $R_{1a}$ is hydroxyl and $R_{1b}$ and $R_2$ are hydrogen.

In some embodiments, disclosed herein the ring system C is selected from the group consisting of 4 membered heteroalicyclyl, 5-membered heteroalicyclyl, and 6-membered heteroalicyclyl; examples are azetidinyl, pyrrolidinyl, piperidinyl, morpholinyl, 2-azabicyclo[3.1.0]hexanyl and 3-azabicyclo[3.1.0]hexanyl. In some embodiments the ring system C is morpholinyl or pyrrolidinyl, which may be unsubstituted or in some embodiments substituted with $R_3$. In some embodiments, C is morpholinyl. $R_3$ may be absent (m is 0), or present one or two times (m is 1 or 2). In some embodiments m is 0. When present two times, each $R_3$ may be attached to the same atom. Each $R_3$ is independently selected from the group consisting $C_{1-4}$ alkyl, $C_{1-4}$ haloalkyl, and halogen, particular examples are methyl, fluoro, difluoro. In some embodiments, $R_3$ is halogen, or methyl and m is 1 or 2. In some embodiments the ring system C is morpholinyl, i.e. $R_3$ is absent (m is 0).

For clarification, $R_4$ is not used within the present disclosure.

In some embodiments of the present disclosure, $R_5$ can be absent when the heteroalicyclyl ring system C is a bicyclic, tricyclic, or tetracyclic ring system, and the carbon atom to which $R_5$ is attached is a bridgehead atom. $R_5$ can also be absent when the carbon atom to which it is attached is part of a double bond.

In some embodiments disclosed herein, $R_5$ is absent (e.g. when rings system C is a bicyclic ring such as 2-azabicyclo[3.1.0]hexanyl making $R_5$ unavailable (absent)), or hydrogen. In some embodiments, $R_5$ is hydrogen.

In some embodiments disclosed herein, $R_6$ is selected from the group consisting of hydrogen, halogen, $C_{1-4}$ haloalkyl, $C_{1-4}$haloalkoxy, $C_{1-4}$ hydroxyalkyl, $C_{1-4}$ hydroxyhaloalkyl, and substituted or unsubstituted 5 membered heteroaryl, e.g. $R_6$ is selected from the group consisting of hydrogen, halogen, —$CF_3$, —$CHF_2$, —$CCH_3F_2$, —$OCF_3$, —$OCHF_2$, —$C(CF_3)_2OH$, and 5 membered heteroaryl, and 5 membered heteroaryl substituted with 1 or 2 methyl.

In many embodiments, $R_6$ is —$CF_3$.

In some embodiments disclosed herein, $R_7$ is selected from the group consisting of hydrogen, halogen, hydroxyl, cyano, —$CF_3$, —$OCHF_2$, —$CHF_2$ and —$OCF_3$, e.g. $R_7$ is selected from the group consisting of hydrogen, fluoro, $CF_3$, and hydroxyl. In some embodiments, $R_7$ is hydrogen.

In some embodiments disclosed herein, $Y_1$, $Y_2$, and $Y_3$ independently are each —CH. In some embodiments, $Y_1$ is —N— and $Y_2$ and $Y_3$ independently are each —CH—. In some embodiments, $Y_2$ is —N— and $Y_1$ and $Y_3$ independently are each —CH—. In some embodiments, $Y_3$ is —N— and $Y_1$ and $Y_2$ independently are each CH. In some embodiments, $Y_3$ is —CH— and $Y_1$ and $Y_2$ are —N—. In some embodiments, $Y_1$ is —CH—, and $Y_2$ and $Y_3$ are independently —$CR_8$— wherein each $R_8$ is selected from the group consisting of hydrogen, methyl, fluoro, hydroxyl and —$CF_3$, or each $R_8$ is hydrogen.

In some embodiments disclosed herein $R_6$ is hydrogen and at least one of $Y_2$ or $Y_3$ is —$CR_8$, wherein $R_8$ is selected from the group consisting of —CN, hydroxyl, halogen, $C_{1-4}$ alkyl, $C_{1-4}$haloalkyl, $C_{1-4}$ hydroxyalkyl, $C_{1-4}$alkoxy, and $C_{1-4}$haloalkoxy.

In one embodiment of Formula (I), R is hydrogen; $R_{0a}$ and $R_{0b}$ independently are hydrogen or methyl; $R_{1a}$ is selected from the group consisting of hydrogen, fluoro and hydroxyl; $R_{1b}$ is hydrogen or fluoro; $R_2$ is selected from the group consisting of hydrogen, fluoro and hydroxyl; ring C is selected from the group consisting of azetidinyl, pyrrolidinyl, morpholinyl, 2-azabicyclo[3.1.0]hexanyl and 3-azabicyclo[3.1.0]hexanyl; m is selected from the group consisting of 0, 1 and 2; $R_3$ is selected from the group consisting of hydrogen, fluoro and methyl; $R_5$ is absent or hydrogen; $R_6$ is selected from the group consisting of hydrogen, —$CF_3$, —$OCF_3$ and —Cl; $R_7$ is hydrogen or fluoro; $Y_1$, $Y_2$ and $Y_3$ are each —CH—; or $Y_1$ is —CH—, $Y_2$ is —CH— and $Y_3$ is —C(OH)—; or $Y_1$ is —CH—, $Y_2$ is —CH— and $Y_3$ is —N—; or $Y_1$ is —CH—, $Y_2$ is —C($CF_3$)— and $Y_3$ is —CH—; or $Y_1$ is —CH—, $Y_2$ is —N— and $Y_3$ is —CH—.

In one embodiment of Formula (I), R is hydrogen; $R_{0a}$ is selected from the group consisting of hydrogen, methyl, —$CH_2OH$, —$CH_2CH_2OH$ and $R_{0b}$ is hydrogen, e.g. both $R_{0a}$ and $R_{0b}$ are hydrogen; $R_{1a}$ is selected from the group consisting of hydroxyl, fluoro and —$CF_3$ and $R_{1b}$ is selected from the group consisting of hydrogen, fluoro, and methyl, e.g., $R_{1a}$ is hydroxyl or fluoro, and $R_{1b}$ is hydrogen, or fluoro; $R_2$ is selected from the group consisting of hydrogen, fluoro and hydroxyl, e.g. hydroxyl; ring system C is morpholinyl or pyrrolidinyl, which may be unsubstituted or in some embodiments substituted with one or two $R_3$ groups, e.g. substituted by methyl, fluoro, difluoro; $R_5$ is hydrogen; $R_6$ is —$CF_3$; $R_7$ is selected from the group consisting of hydrogen, fluoro, —$CF_3$ and hydroxyl, e.g. hydrogen; $Y_2$ is —N— and $Y_1$ and $Y_3$ independently are —CH—, or $Y_3$ is —N— and $Y_1$ and $Y_2$ independently are —CH— or $Y_1$ is —CH—, and $Y_2$ and $Y_3$ are independently —$CR_8$— wherein each $R_8$ is selected from the group consisting of hydrogen, methyl, fluoro, hydroxyl and —$CF_3$, e.g. each $R_8$ is hydrogen.

In one embodiment, the compound, stereoisomer, or salt according to Formula (I), is selected from a compound of one of the following Formulae

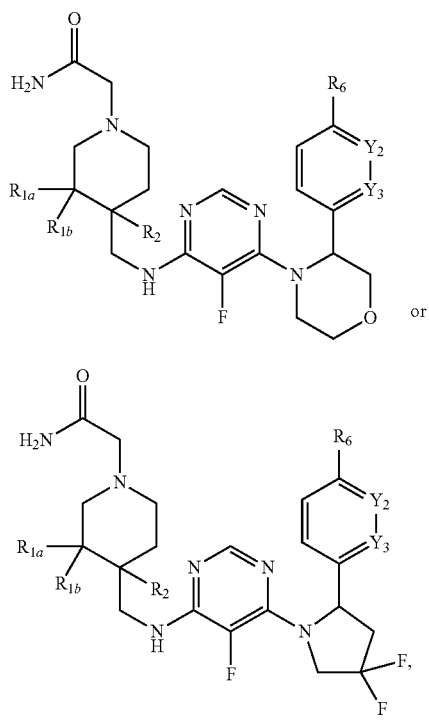

wherein
$R_{1a}$ is fluoro or hydroxyl;
$R_{1b}$ is hydrogen or fluoro;
$R_2$ is hydrogen or hydroxyl;
$R_6$ is $CF_3$; and
$Y_2$ and $Y_3$ each are independently selected from the group consisting of —N—, —CH—, and —CF—. For example, both $Y_2$ and $Y_3$ are —CH—, or $Y_2$ is —CH—, and $Y_3$ is —CF. Or for example both $Y_2$ and $Y_3$ are each —CH—, or $Y_2$ is —CH—, and $Y_3$ is —CF—, and $R_{1a}$ is hydroxyl and $R_{1b}$ is hydrogen, or $R_{1a}$ is fluoro and $R_{1b}$ is hydrogen or fluoro.

In one embodiment, the compound, stereoisomer, or salt according to Formula (I) is selected from the group consisting of:
2-(4-(((5-Fluoro-6-((S)-3-(5-trifluoromethyl)pyridin-2-yl)morpholino)pyrimidin-4-yl)amino)methyl)piperidin-1-yl)propanamide,
(S)-2-(4-(((5-fluoro-6-(3-(5-trifluoromethyl)pyridin-2-yl)morpholino)pyrimidin-4-yl)amino)methyl)piperidin-1-yl)acetamide,
(S)-2-(4-(((5-fluoro-6-(3-(5-trifluoromethyl)pyridin-2-yl)morpholino)pyrimidin-4-yl)amino)methyl)piperidin-1-yl)-2-methylpropanamide,
(S)-2-(4-fluoro-4-(((5-fluoro-6-(3-(4-(trifluoromethyl)phenyl)morpholino)pyrimidin-4-yl)amino)methyl)piperidin-1-yl)acetamide,
(S)-2-(4-(((5-fluoro-6-(3-(4-(trifluoromethyl)phenyl)morpholino)pyrimidin-4-yl)amino)methyl)piperidin-1-yl)acetamide,
(S)-2-(4-fluoro-4-(((5-fluoro-6-(3-(4-(trifluoromethoxy)phenyl)morpholino)pyrimidin-4-yl)amino)methyl)piperidin-1-yl)acetamide,
2-((3RS,4RS)-4-(((5-fluoro-6-((S)-3-(4-(trifluoromethyl)phenyl)morpholino)pyrimidin-4-yl)amino)methyl)-3-hydroxypiperidin-1-yl)acetamide,
2-((3R*,4R*)-4-(((5-fluoro-6-((S)-3-(4-(trifluoromethyl)phenyl)morpholino)pyrimidin-4-yl)amino)methyl)-3-hydroxypiperidin-1-yl)acetamide, $1^{st}$ eluting isomer,
2-((3R*,4R*)-4-(((5-fluoro-6-((S)-3-(4-(trifluoromethyl)phenyl)morpholino)pyrimidin-4-yl)amino)methyl)-3-hydroxypiperidin-1-yl)acetamide, $2^{nd}$ eluting isomer,
(S)-2-(4-fluoro-4-(((5-fluoro-6-(3-(5-(trifluoromethyl)pyridin-2-yl)morpholino)pyrimidin-4-yl)amino)methyl)piperidin-1-yl)acetamide,
2-((R*)-3,3-difluoro-4-(((5-fluoro-6-((S)-3-(4-(trifluoromethyl)phenyl)morpholino)-pyrimidin-4-yl)amino)methyl)piperidin-1-yl)acetamide, $1^{st}$ eluting isomer,
2-((R*)-3,3-difluoro-4-(((5-fluoro-6-((S)-3-(4-(trifluoromethyl)phenyl)morpholino)-pyrimidin-4-yl)amino)methyl)piperidin-1-yl)acetamide, $2^{nd}$ eluting isomer,
2-((3R*,4R*)-3-fluoro-4-(((5-fluoro-6-((S)-3-(4-(trifluoromethyl)phenyl)morpholino)-pyrimidin-4-yl)amino)methyl)piperidin-1-yl)acetamide, $1^{st}$ eluting isomer,
2-((3R*,4R*)-3-fluoro-4-(((5-fluoro-6-((S)-3-(4-(trifluoromethyl)phenyl)morpholino)-pyrimidin-4-yl)amino)methyl)piperidin-1-yl)acetamide, $2^{nd}$ eluting isomer,
2-((R*)-3,3-difluoro-4-(((5-fluoro-6-((S)-3-(5-(trifluoromethyl)pyridin-2-yl)morpholino)-pyrimidin-4-yl)amino)methyl)piperidin-1-yl)acetamide, $1^{st}$ eluting isomer,
2-((R*)-3,3-difluoro-4-(((5-fluoro-6-((S)-3-(5-(trifluoromethyl)pyridin-2-yl)-morpholino)pyrimidin-4-yl)amino)methyl)piperidin-1-yl)acetamide, $2^{nd}$ eluting isomer,
2-((3R*,4S*)-3-fluoro-4-(((5-fluoro-6-((S)-3-(5-(trifluoromethyl)pyridin-2-yl)-morpholino)pyrimidin-4-yl)amino)methyl)piperidin-1-yl)acetamide, $1^{st}$ eluting isomer,
2-((3R*,4S*)-3-fluoro-4-(((5-fluoro-6-((S)-3-(5-(trifluoromethyl)pyridin-2-yl)-morpholino)pyrimidin-4-yl)amino)methyl)piperidin-1-yl)acetamide, $2^{nd}$ eluting isomer,
2-((3R*,4R*)-3-fluoro-4-(((5-fluoro-6-((S)-3-(5-(trifluoromethyl)pyridin-2-yl)-morpholino)pyrimidin-4-yl)amino)methyl)piperidin-1-yl)acetamide, $1^{st}$ eluting isomer,
2-((3R*,4R*)-3-fluoro-4-(((5-fluoro-6-((S)-3-(5-(trifluoromethyl)pyridin-2-yl)-morpholino)pyrimidin-4-yl)amino)methyl)piperidin-1-yl)acetamide, $2^{nd}$ eluting isomer,
(R)-2-(4-(((6-(4,4-difluoro-2-(4-(trifluoromethyl)phenyl)pyrrolidin-1-yl)-5-fluoropyrimidin-4-yl)amino)methyl)-4-hydroxypiperidin-1-yl)acetamide,
2-((R*)-4-(((6-((R)-4,4-difluoro-2-(4-(trifluoromethyl)phenyl)pyrrolidin-1-yl)-5-fluoro-pyrimidin-4-yl)amino)methyl)-3,3-difluoropiperidin-1-yl)acetamide, $1^{st}$ eluting isomer,
2-((R*)-4-(((6-((R)-4,4-difluoro-2-(4-(trifluoromethyl)phenyl)pyrrolidin-1-yl)-5-fluoro-pyrimidin-4-yl)amino)methyl)-3,3-difluoropiperidin-1-yl)acetamide, $2^{nd}$ eluting isomer,
2-((3R*,4R*)-4-(((6-((R)-4,4-difluoro-2-(4-(trifluoromethyl)phenyl)pyrrolidin-1-yl)-5-fluoro-pyrimidin-4-yl)amino)methyl)-3-fluoropiperidin-1-yl)acetamide, $1^{st}$ eluting isomer, 2-((3R*,4R*)-4-(((6-((R)-4,4-difluoro-2-(4-(trifluoromethyl)phenyl)pyrrolidin-1-yl)-5-fluoropyrimidin-4-yl)amino)methyl)-3-fluoropiperidin-1-yl)acetamide, 2$^{nd}$ eluting isomer, 2-((3RS,4RS)-4-(((6-((R)-4,4-difluoro-2-(4-(trifluoromethyl)phenyl)pyrrolidin-1-yl)-5-fluoropyrimidin-4-yl)amino)methyl)-3-hydroxypiperidin-1-yl)acetamide, 2-((3R*,4R*)-4-(((6-((R)-4,4-difluoro-2-(4-(trifluoromethyl)phenyl)pyrrolidin-1-yl)-5-fluoropyrimidin-4-yl)amino)methyl)-3-hydroxypiperidin-1-yl)acetamide, 1$^{st}$ eluting isomer, 2-((3R*,4R*)-4-(((6-((R)-4,4-difluoro-2-(4-(trifluoromethyl)phenyl)pyrrolidin-1-yl)-5-fluoropyrimidin-4-yl)amino)methyl)-3-hydroxypiperidin-1-yl)acetamide, 2$^{nd}$ eluting isomer, 2-((3R*,4R*)-4-(((6-((R)-4,4-difluoro-2-(5-(trifluoromethyl)pyridin-2-yl)pyrrolidin-1-yl)-5-fluoropyrimidin-4-yl)amino)methyl)-3-fluoropiperidin-1-yl)acetamide, 1$^{st}$ eluting isomer, 2-((3R*,4R*)-4-(((6-((R)-4,4-difluoro-2-(5-(trifluoromethyl)pyridin-2-yl)pyrrolidin-1-yl)-5-fluoropyrimidin-4-yl)amino)methyl)-3-fluoropiperidin-1-yl)acetamide, 2$^{nd}$ eluting isomer, 2-((R*)-4-(((6-((R)-4,4-difluoro-2-(5-(trifluoromethyl)pyridin-2-yl)pyrrolidin-1-yl)-5-fluoropyrimidin-4-yl)amino)methyl)-3,3-difluoropiperidin-1-yl)acetamide, 1$^{st}$ eluting isomer, 2-((R*)-4-(((6-((R)-4,4-difluoro-2-(5-(trifluoromethyl)pyridin-2-yl)pyrrolidin-1-yl)-5-fluoropyrimidin-4-yl)amino)methyl)-3,3-difluoropiperidin-1-yl)acetamide, 2$^{nd}$ eluting isomer, 2-((3RS,4RS)-4-(((6-((R)-4,4-difluoro-2-(5-(trifluoromethyl)pyridin-2-yl)pyrrolidin-1-yl)-5-fluoropyrimidin-4-yl)amino)methyl)-3-hydroxypiperidin-1-yl)acetamide, rel-2-((3R,4R)-4-(((5-fluoro-6-((3S,5R)-3-methyl-5-(3-(trifluoromethyl)phenyl)morpholino)-pyrimidin-4-yl)amino)methyl)-3-hydroxypiperidin-1-yl)acetamide or rel-2-((3R,4R)-4-(((5-fluoro-6-((3R,5S)-3-methyl-5-(3-(trifluoromethyl)phenyl)morpholino)pyrimidin-4-yl)amino)methyl)-3-hydroxypiperidin-1-yl)acetamide, 1$^{st}$ eluting isomer, rel-2-((3R,4R)-4-(((5-fluoro-6-((3S,5R)-3-methyl-5-(3-(trifluoromethyl)phenyl)-morpholino)pyrimidin-4-yl)amino)methyl)-3-hydroxypiperidin-1-yl)acetamide or rel-2-((3R,4R)-4-(((5-fluoro-6-((3R,5S)-3-methyl-5-(3-(trifluoromethyl)phenyl)morpholino)-pyrimidin-4-yl)amino)methyl)-3-hydroxypiperidin-1-yl)acetamide, 2$^{nd}$ eluting isomer, rel-2-((3R,4R)-4-(((5-fluoro-6-((3S,5R)-3-methyl-5-(3-(trifluoromethyl)phenyl)morpholino)-pyrimidin-4-yl)amino)methyl)-3-hydroxypiperidin-1-yl)acetamide or rel-2-((3R,4R)-4-(((5-fluoro-6-((3R,5S)-3-methyl-5-(3-(trifluoromethyl)phenyl)morpholino)-pyrimidin-4-yl)amino)methyl)-3-hydroxypiperidin-1-yl)acetamide, 1$^{st}$ eluting isomer, rel-2-((3R,4R)-4-(((5-fluoro-6-((3S,5R)-3-methyl-5-(4-(trifluoromethyl)phenyl)morpholino)pyrimidin-4-yl)amino)methyl)-3-hydroxypiperidin-1-yl)acetamide or rel-2-((3R,4R)-4-(((5-fluoro-6-((3R,5S)-3-methyl-5-(4-(trifluoromethyl)phenyl)morpholino)pyrimidin-4-yl)amino)methyl)-3-hydroxypiperidin-1-yl)acetamide, 1$^{st}$ eluting isomer, rel-2-((3R,4R)-4-(((5-fluoro-6-((3S,5R)-3-methyl-5-(4-(trifluoromethyl)phenyl)-morpholino)pyrimidin-4-yl)amino)methyl)-3-hydroxypiperidin-1-yl)acetamide or rel-2-((3R,4R)-4-(((5-fluoro-6-((3R,5S)-3-methyl-5-(4-(trifluoromethyl)phenyl)-morpholino)pyrimidin-4-yl)amino)methyl)-3-hydroxypiperidin-1-yl)acetamide, 2$^{nd}$ eluting isomer, rel-2-((3R,4R)-4-(((5-fluoro-6-((3S,5R)-3-methyl-5-(4-(trifluoromethyl)phenyl)morpholino)-pyrimidin-4-yl)amino)methyl)-3-hydroxypiperidin-1-yl)acetamide or rel-2-((3R,4R)-4-(((5-fluoro-6-((3R,5S)-3-methyl-5-(4-(trifluoromethyl)phenyl)morpholino)pyrimidin-4-yl)amino)methyl)-3-hydroxypiperidin-1-yl)acetamide, 2$^{nd}$ eluting isomer, (S)-2-(4-(((5-fluoro-6-(3-(4-(trifluoromethoxy)phenyl)morpholino)pyrimidin-4-yl)amino)methyl)piperidin-1-yl)acetamide, 2-(4-(((6-(4,4-difluoro-2-(4-(trifluoromethyl)phenyl)pyrrolidin-1-yl)-5-fluoropyrimidin-4-yl)amino)methyl)piperidin-1-yl)acetamide, 2-(4-(((5-fluoro-6-(2-(4-(trifluoromethyl)phenyl)pyrrolidin-1-yl)pyrimidin-4-yl)amino)methyl)piperidin-1-yl)acetamide, (R)-2-(4-(((5-fluoro-6-(2-(4-(trifluoromethyl)phenyl)pyrrolidin-1-yl)pyrimidin-4-yl)amino)methyl)piperidin-1-yl)acetamide, 2-(4-(((5-fluoro-6-(2-(2-hydroxy-4-(trifluoromethyl)phenyl)pyrrolidin-1-yl)pyrimidin-4-yl)amino)methyl)piperidin-1-yl)acetamide, rac-2-(4-(((5-fluoro-6-((2R,4R)-4-fluoro-2-(4-(trifluoromethyl)phenyl)pyrrolidin-1-yl)pyrimidin-4-yl)amino)methyl)piperidin-1-yl)acetamide, 2-(4-(((5-fluoro-6-(2-(4-(trifluoromethyl)phenyl)azetidin-1-yl)pyrimidin-4-yl)amino)methyl)piperidin-1-yl)acetamide, rac-2-((3R,4R)-4-(((6-(2-(4-chlorophenyl)pyrrolidin-1-yl)-5-fluoropyrimidin-4-yl)amino)methyl)-3-hydroxypiperidin-1-yl)acetamide, 2-((3RS,4RS)-4-(((5-fluoro-6-((1S*,5R*)-1-(6-(trifluoromethyl)pyridin-3-yl)-2-azabicyclo[3.1.0]hexan-2-yl)pyrimidin-4-yl)amino)methyl)-3-hydroxypiperidin-1-yl)acetamide, rac-2-((3R,4R)-4-(((5-fluoro-6-(2-(6-(trifluoromethyl)pyridin-3-yl)-3-azabicyclo[3.1.0]hexan-3-yl)pyrimidin-4-yl)amino)methyl)-3-hydroxypiperidin-1-yl)acetamide, rac-2-((3R,4R)-4-(((5-fluoro-6-(2-(4-(trifluoromethyl)phenyl)azetidin-1-yl)pyrimidin-4-yl)amino)methyl)-3-hydroxypiperidin-1-yl)acetamide, 2-((3R*,4R*)-4-(((5-fluoro-6-((S)-3-(2-fluoro-4-(trifluoromethyl)phenyl)morpholino)-pyrimidin-4-yl)amino)methyl)-3-hydroxypiperidin-1-yl)acetamide, 2-((3R*,4R*)-4-(((5-fluoro-6-((R)-2-(2-fluoro-4-(trifluoromethyl)phenyl)pyrrolidin-1-yl)pyrimidin-4-yl)amino)methyl)-3-hydroxypiperidin-1-yl)acetamide, 2-((3R*,4R*)-3-fluoro-4-(((5-fluoro-6-((R)-2-(2-fluoro-4-(trifluoromethyl)phenyl)pyrrolidin-1-yl)pyrimidin-4-yl)amino)methyl)piperidin-1-yl)acetamide, 2-((3R*,4R*)-3-fluoro-4-(((5-fluoro-6-((S)-3-(2-fluoro-4-(trifluoromethyl)phenyl)-morpholino)pyrimidin-4-yl)amino)methyl)piperidin-1-yl)acetamide,
2-((3R*,4R*)-4-(((6-((R)-4,4-difluoro-2-(2-fluoro-4-(trifluoromethyl)phenyl)pyrrolidin-1-yl)-5-fluoropyrimidin-4-yl)amino)methyl)-3-hydroxypiperidin-1-yl)acetamide,
2-((3R*,4R*)-4-(((6-((R)-4,4-difluoro-2-(2-fluoro-4-(trifluoromethyl)phenyl)pyrrolidin-1-yl)-5-fluoropyrimidin-4-yl)amino)methyl)-3-fluoropiperidin-1-yl)acetamide,
2-((R*)-3,3-difluoro-4-(((5-fluoro-6-((S)-3-(2-fluoro-4-(trifluoromethyl)phenyl)-morpholino)pyrimidin-4-yl)amino)methyl)piperidin-1-yl)acetamide,
2-((R*)-3,3-difluoro-4-(((5-fluoro-6-((R)-2-(2-fluoro-4-(trifluoromethyl)phenyl)pyrrolidin-1-yl)pyrimidin-4-yl)amino)methyl)piperidin-1-yl)acetamide, and
2-((R*)-4-(((6-((R)-4,4-difluoro-2-(2-fluoro-4-(trifluoromethyl)phenyl)pyrrolidin-1-yl)-5-fluoropyrimidin-4-yl)amino)methyl)-3,3-difluoropiperidin-1-yl)acetamide.

In some cases, the compound, stereoisomer, or salt of a stereoisomer, according to Formula (I) is selected from the group consisting of:
2-((3R*,4R*)-4-(((5-fluoro-6-((S)-3-(4-(trifluoromethyl)phenyl)morpholino)pyrimidin-4-yl)amino)methyl)-3-hydroxypiperidin-1-yl)acetamide, 1$^{st}$ eluting isomer,
2-((3R*,4R*)-4-(((5-fluoro-6-((S)-3-(4-(trifluoromethyl)phenyl)morpholino)pyrimidin-4-yl)amino)methyl)-3-hydroxypiperidin-1-yl)acetamide, 2$^{nd}$ eluting isomer,
2-((R*)-3,3-difluoro-4-(((5-fluoro-6-((S)-3-(4-(trifluoromethyl)phenyl)morpholino)-pyrimidin-4-yl)amino)methyl)piperidin-1-yl)acetamide, 1$^{st}$ eluting isomer,
2-((R*)-3,3-difluoro-4-(((5-fluoro-6-((S)-3-(4-(trifluoromethyl)phenyl)morpholino)-pyrimidin-4-yl)amino)methyl)piperidin-1-yl)acetamide, 2$^{nd}$ eluting isomer,
2-((3R*,4R*)-3-fluoro-4-(((5-fluoro-6-((S)-3-(4-(trifluoromethyl)phenyl)morpholino)-pyrimidin-4-yl)amino)methyl)piperidin-1-yl)acetamide, 1$^{st}$ eluting isomer,
2-((3R*,4R*)-3-fluoro-4-(((5-fluoro-6-((S)-3-(4-(trifluoromethyl)phenyl)-morpholino)pyrimidin-4-yl)amino)methyl)piperidin-1-yl)acetamide, 2$^{nd}$ eluting isomer,
2-((R*)-4-(((6-((R)-4,4-difluoro-2-(4-(trifluoromethyl)phenyl)pyrrolidin-1-yl)-5-fluoro-pyrimidin-4-yl)amino)methyl)-3,3-difluoropiperidin-1-yl)acetamide, 1$^{st}$ eluting isomer,
2-((R*)-4-(((6-((R)-4,4-difluoro-2-(4-(trifluoromethyl)phenyl)pyrrolidin-1-yl)-5-fluoro-pyrimidin-4-yl)amino)methyl)-3,3-difluoropiperidin-1-yl)acetamide, 2$^{nd}$ eluting isomer,
2-((3R*,4R*)-4-(((6-((R)-4,4-difluoro-2-(4-(trifluoromethyl)phenyl)pyrrolidin-1-yl)-5-fluoro-pyrimidin-4-yl)amino)methyl)-3-fluoropiperidin-1-yl)acetamide, 1$^{st}$ eluting isomer,
2-((3R*,4R*)-4-(((6-((R)-4,4-difluoro-2-(4-(trifluoromethyl)phenyl)pyrrolidin-1-yl)-5-fluoropyrimidin-4-yl)amino)methyl)-3-fluoropiperidin-1-yl)acetamide, 2$^{nd}$ eluting isomer,
2-((3R*,4R*)-4-(((6-((R)-4,4-difluoro-2-(4-(trifluoromethyl)phenyl)pyrrolidin-1-yl)-5-fluoropyrimidin-4-yl)amino)methyl)-3-hydroxypiperidin-1-yl)acetamide, 1$^{st}$ eluting isomer, and
2-((3R*,4R*)-4-(((6-((R)-4,4-difluoro-2-(4-(trifluoromethyl)phenyl)pyrrolidin-1-yl)-5-fluoropyrimidin-4-yl)amino)methyl)-3-hydroxypiperidin-1-yl)acetamide, 2$^{nd}$ eluting isomer.

In one embodiment, the compound or stereoisomer, or salt of the compound or stereoisomer according to Formula (I) is selected from the group consisting of:

2-(4-(((5-Fluoro-6-((S)-3-(5-trifluoromethyl)pyridin-2-yl)morpholino)pyrimidin-4-yl)amino)methyl)piperidin-1-yl)propanamide,
(S)-2-(4-(((5-fluoro-6-(3-(5-(trifluoromethyl)pyridin-2-yl)morpholino)pyrimidin-4-yl)amino)methyl)piperidin-1-yl)acetamide,
(S)-2-(4-(((5-fluoro-6-(3-(5-(trifluoromethyl)pyridin-2-yl)morpholino)pyrimidin-4-yl)amino)methyl)piperidin-1-yl)-2-methylpropanamide,
(S)-2-(4-fluoro-4-(((5-fluoro-6-(3-(4-(trifluoromethyl)phenyl)morpholino)pyrimidin-4-yl)amino)methyl)piperidin-1-yl)acetamide,
(S)-2-(4-(((5-fluoro-6-(3-(4-(trifluoromethyl)phenyl)morpholino)pyrimidin-4-yl)amino)methyl)piperidin-1-yl)acetamide,
(S)-2-(4-fluoro-4-(((5-fluoro-6-(3-(4-(trifluoromethoxy)phenyl)morpholino)pyrimidin-4-yl)amino)methyl)piperidin-1-yl)acetamide,
2-((3RS,4RS)-4-(((5-fluoro-6-((S)-3-(4-(trifluoromethyl)phenyl)morpholino)pyrimidin-4-yl)amino)methyl)-3-hydroxypiperidin-1-yl)acetamide,
2-((3R*,4R*)-4-(((5-fluoro-6-((S)-3-(4-(trifluoromethyl)phenyl)morpholino)pyrimidin-4-yl)amino)methyl)-3-hydroxypiperidin-1-yl)acetamide,
(S)-2-(4-fluoro-4-(((5-fluoro-6-(3-(5-(trifluoromethyl)pyridin-2-yl)morpholino)pyrimidin-4-yl)amino)methyl)piperidin-1-yl)acetamide,
2-((R*)-3,3-difluoro-4-(((5-fluoro-6-((S)-3-(4-(trifluoromethyl)phenyl)-morpholino)pyrimidin-4-yl)amino)methyl)piperidin-1-yl)acetamide,
2-((3R*,4R*)-3-fluoro-4-(((5-fluoro-6-((S)-3-(4-(trifluoromethyl)phenyl)-morpholino)pyrimidin-4-yl)amino)methyl)piperidin-1-yl)acetamide,
2-((R*)-3,3-difluoro-4-(((5-fluoro-6-((S)-3-(5-(trifluoromethyl)pyridin-2-yl)morpholino)pyrimidin-4-yl)amino)methyl)piperidin-1-yl)acetamide,
2-((3R*,4S*)-3-fluoro-4-(((5-fluoro-6-((S)-3-(5-(trifluoromethyl)pyridin-2-yl)morpholino)pyrimidin-4-yl)amino)methyl)piperidin-1-yl)acetamide,
2-((3R*,4R*)-3-fluoro-4-(((5-fluoro-6-((S)-3-(5-(trifluoromethyl)pyridin-2-yl)morpholino)pyrimidin-4-yl)amino)methyl)piperidin-1-yl)acetamide,
(R)-2-(4-(((6-(4,4-difluoro-2-(4-(trifluoromethyl)phenyl)pyrrolidin-1-yl)-5-fluoropyrimidin-4-yl)amino)methyl)-4-hydroxypiperidin-1-yl)acetamide,
2-((R*)-4-(((6-((R)-4,4-difluoro-2-(4-(trifluoromethyl)phenyl)pyrrolidin-1-yl)-5-fluoropyrimidin-4-yl)amino)methyl)-3,3-difluoropiperidin-1-yl)acetamide,
2-((3R*,4R*)-4-(((6-((R)-4,4-difluoro-2-(4-(trifluoromethyl)phenyl)pyrrolidin-1-yl)-5-fluoropyrimidin-4-yl)amino)methyl)-3-fluoropiperidin-1-yl)acetamide,
2-((3RS,4RS)-4-(((6-((R)-4,4-difluoro-2-(4-(trifluoromethyl)phenyl)pyrrolidin-1-yl)-5-fluoropyrimidin-4-yl)amino)methyl)-3-hydroxypiperidin-1-yl)acetamide,
2-((3R*,4R*)-4-(((6-((R)-4,4-difluoro-2-(4-(trifluoromethyl)phenyl)pyrrolidin-1-yl)-5-fluoropyrimidin-4-yl)amino)methyl)-3-hydroxypiperidin-1-yl)acetamide,
2-((3R*,4R*)-4-(((6-((R)-4,4-difluoro-2-(5-(trifluoromethyl)pyridin-2-yl)pyrrolidin-1-yl)-5-fluoropyrimidin-4-yl)amino)methyl)-3-fluoropiperidin-1-yl)acetamide,
2-((R*)-4-(((6-((R)-4,4-difluoro-2-(5-(trifluoromethyl)pyridin-2-yl)pyrrolidin-1-yl)-5-fluoropyrimidin-4-yl)amino)methyl)-3,3-difluoropiperidin-1-yl)acetamide,
2-((3RS,4RS)-4-(((6-((R)-4,4-difluoro-2-(5-(trifluoromethyl)pyridin-2-yl)pyrrolidin-1-yl)-5-fluoropyrimidin-4-yl)amino)methyl)-3-hydroxypiperidin-1-yl)acetamide, rel-2-((3R,4R)-4-(((5-fluoro-6-((3S,5R)-3-methyl-5-(3-(trifluoromethyl)-phenyl)morpholino)pyrimidin-4-yl)amino)methyl)-3-hydroxypiperidin-1-yl)acetamide, rel-2-((3R,4R)-4-(((5-fluoro-6-((3R,5S)-3-methyl-5-(3-(trifluoromethyl)phenyl)-morpholino)pyrimidin-4-yl)amino)methyl)-3-hydroxypiperidin-1-yl)acetamide, rel-2-((3R,4R)-4-(((5-fluoro-6-((3S,5R)-3-methyl-5-(4-(trifluoromethyl)phenyl)-morpholino)pyrimidin-4-yl)amino)methyl)-3-hydroxypiperidin-1-yl)acetamide, rel-2-((3R,4R)-4-(((5-fluoro-6-((3R,5S)-3-methyl-5-(4-(trifluoromethyl)phenyl)-morpholino)pyrimidin-4-yl)amino)methyl)-3-hydroxypiperidin-1-yl)acetamide, (S)-2-(4-(((5-fluoro-6-(3-(4-(trifluoromethoxy)phenyl)morpholino)pyrimidin-4-yl)amino)methyl)piperidin-1-yl)acetamide, 2-(4-(((6-(4,4-difluoro-2-(4-(trifluoromethyl)phenyl)pyrrolidin-1-yl)-5-fluoropyrimidin-4-yl)amino)methyl)piperidin-1-yl)acetamide, 2-(4-(((5-fluoro-6-(2-(4-(trifluoromethyl)phenyl)pyrrolidin-1-yl)pyrimidin-4-yl)amino)methyl)piperidin-1-yl)acetamide, (R)-2-(4-(((5-fluoro-6-(2-(4-(trifluoromethyl)phenyl)pyrrolidin-1-yl)pyrimidin-4-yl)amino)methyl)piperidin-1-yl)acetamide, 2-(4-(((5-fluoro-6-(2-(2-hydroxy-4-(trifluoromethyl)phenyl)pyrrolidin-1-yl)pyrimidin-4-yl)amino)methyl)piperidin-1-yl)acetamide, rac-2-(4-(((5-fluoro-6-((2R,4R)-4-fluoro-2-(4-(trifluoromethyl)phenyl)pyrrolidin-1-yl)pyrimidin-4-yl)amino)methyl)piperidin-1-yl)acetamide, 2-(4-(((5-fluoro-6-(2-(4-(trifluoromethyl)phenyl)azetidin-1-yl)pyrimidin-4-yl)amino)methyl)piperidin-1-yl)acetamide, rac-2-((3R,4R)-4-(((6-(2-(4-chlorophenyl)pyrrolidin-1-yl)-5-fluoropyrimidin-4-yl)amino)methyl)-3-hydroxypiperidin-1-yl)acetamide, 2-((3RS,4RS)-4-(((5-fluoro-6-((1S*,5R*)-1-(6-(trifluoromethyl)pyridin-3-yl)-2-azabicyclo-[3.1.0]hexan-2-yl)pyrimidin-4-yl)amino)methyl)-3-hydroxypiperidin-1-yl)acetamide, rac-2-((3R,4R)-4-(((5-fluoro-6-(2-(6-(trifluoromethyl)pyridin-3-yl)-3-azabicyclo-[3.1.0]hexan-3-yl)pyrimidin-4-yl)amino)methyl)-3-hydroxypiperidin-1-yl)acetamide, rac-2-((3R,4R)-4-(((5-fluoro-6-(2-(4-(trifluoromethyl)phenyl)azetidin-1-yl)pyrimidin-4-yl)amino)methyl)-3-hydroxypiperidin-1-yl)acetamide, 2-((3R*,4R*)-4-(((5-fluoro-6-((S)-3-(2-fluoro-4-(trifluoromethyl)phenyl)morpholino)-pyrimidin-4-yl)amino)methyl)-3-hydroxypiperidin-1-yl)acetamide, 2-((3R*,4R*)-4-(((5-fluoro-6-((R)-2-(2-fluoro-4-(trifluoromethyl)phenyl)pyrrolidin-1-yl)pyrimidin-4-yl)amino)methyl)-3-hydroxypiperidin-1-yl)acetamide, 2-((3R*,4R*)-3-fluoro-4-(((5-fluoro-6-((R)-2-(2-fluoro-4-(trifluoromethyl)phenyl)pyrrolidin-1-yl)pyrimidin-4-yl)amino)methyl)piperidin-1-yl)acetamide, 2-((3R*,4R*)-3-fluoro-4-(((5-fluoro-6-((S)-3-(2-fluoro-4-(trifluoromethyl)phenyl)-morpholino)pyrimidin-4-yl)amino)methyl)piperidin-1-yl)acetamide, 2-((3R*,4R*)-4-(((6-((R)-4,4-difluoro-2-(2-fluoro-4-(trifluoromethyl)phenyl)pyrrolidin-1-yl)-5-fluoropyrimidin-4-yl)amino)methyl)-3-hydroxypiperidin-1-yl)acetamide, 2-((3R*,4R*)-4-(((6-((R)-4,4-difluoro-2-(2-fluoro-4-(trifluoromethyl)phenyl)pyrrolidin-1-yl)-5-fluoropyrimidin-4-yl)amino)methyl)-3-fluoropiperidin-1-yl)acetamide, 2-((R*)-3,3-difluoro-4-(((5-fluoro-6-((S)-3-(2-fluoro-4-(trifluoromethyl)phenyl)-morpholino)pyrimidin-4-yl)amino)methyl)piperidin-1-yl)acetamide, 2-((R*)-3,3-difluoro-4-(((5-fluoro-6-((R)-2-(2-fluoro-4-(trifluoromethyl)phenyl)pyrrolidin-1-yl)pyrimidin-4-yl)amino)methyl)piperidin-1-yl)acetamide, and 2-((R*)-4-(((6-((R)-4,4-difluoro-2-(2-fluoro-4-(trifluoromethyl)phenyl)pyrrolidin-1-yl)-5-fluoropyrimidin-4-yl)amino)methyl)-3,3-difluoropiperidin-1-yl)acetamide.

In some cases, the compound, stereoisomer or salt is selected from the group consisting of 2-(4-(((5-fluoro-6-(3-(5-trifluoromethyl)pyridin-2-yl)morpholino)pyrimidin-4-yl)amino)methyl)piperidin-1-yl)propanamide, 2-(4-(((5-fluoro-6-(3-(5-(trifluoromethyl)pyridin-2-yl)morpholino)pyrimidin-4-yl)amino)methyl)piperidin-1-yl)acetamide, 2-(4-(((5-fluoro-6-(3-(5-(trifluoromethyl)pyridin-2-yl)morpholino)pyrimidin-4-yl)amino)methyl)piperidin-1-yl)-2-methylpropanamide, 2-(4-fluoro-4-(((5-fluoro-6-(3-(4-(trifluoromethyl)phenyl)morpholino)pyrimidin-4-yl)amino)methyl)piperidin-1-yl)acetamide, 2-(4-(((5-fluoro-6-(3-(4-(trifluoromethyl)phenyl)morpholino)pyrimidin-4-yl)amino)methyl)piperidin-1-yl)acetamide, 2-(4-fluoro-4-(((5-fluoro-6-(3-(4-(trifluoromethoxy)phenyl)morpholino)pyrimidin-4-yl)amino)methyl)piperidin-1-yl)acetamide, 2-(4-(((5-fluoro-6-(3-(4-(trifluoromethyl)phenyl)morpholino)pyrimidin-4-yl)amino)methyl)-3-hydroxypiperidin-1-yl)acetamide, 2-(4-fluoro-4-(((5-fluoro-6-(3-(5-(trifluoromethyl)pyridin-2-yl)morpholino)pyrimidin-4-yl)amino)methyl)piperidin-1-yl)acetamide, 2-(3,3-difluoro-4-(((5-fluoro-6-(3-(4-(trifluoromethyl)phenyl)morpholino)pyrimidin-4-yl)amino)methyl)piperidin-1-yl)acetamide, 2-(3-fluoro-4-(((5-fluoro-6-(3-(4-(trifluoromethyl)phenyl)morpholino)pyrimidin-4-yl)amino)methyl)piperidin-1-yl)acetamide, 2-(3,3-difluoro-4-(((5-fluoro-6-(3-(5-(trifluoromethyl)pyridin-2-yl)morpholino)pyrimidin-4-yl)amino)methyl)piperidin-1-yl)acetamide, 2-(3-fluoro-4-(((5-fluoro-6-(3-(5-(trifluoromethyl)pyridin-2-yl)morpholino)pyrimidin-4-yl)amino)methyl)piperidin-1-yl)acetamide, 2-(4-(((6-(4,4-difluoro-2-(4-(trifluoromethyl)phenyl)pyrrolidin-1-yl)-5-fluoropyrimidin-4-yl)amino)methyl)-4-hydroxypiperidin-1-yl)acetamide, 2-(4-(((6-(4,4-difluoro-2-(4-(trifluoromethyl)phenyl)pyrrolidin-1-yl)-5-fluoropyrimidin-4-yl)amino)methyl)-3,3-difluoropiperidin-1-yl)acetamide, 2-(4-(((6-(4,4-difluoro-2-(4-(trifluoromethyl)phenyl)pyrrolidin-1-yl)-5-fluoropyrimidin-4-yl)amino)methyl)-3-fluoropiperidin-1-yl)acetamide, 2-(4-(((6-(4,4-difluoro-2-(4-(trifluoromethyl)phenyl)pyrrolidin-1-yl)-5-fluoropyrimidin-4-yl)amino)methyl)-3-hydroxypiperidin-1-yl)acetamide, 2-(4-(((6-(4,4-difluoro-2-(5-(trifluoromethyl)pyridin-2-yl)pyrrolidin-1-yl)-5-fluoropyrimidin-4-yl)amino)methyl)-3-fluoropiperidin-1-yl)acetamide, 2-(4-(((6-(4,4-difluoro-2-(5-(trifluoromethyl)pyridin-2-yl)pyrrolidin-1-yl)-5-fluoropyrimidin-4-yl)amino)methyl)-3,3-difluoropiperidin-1-yl)acetamide, 2-(4-(((6-(4,4-difluoro-2-(5-(trifluoromethyl)pyridin-2-yl)pyrrolidin-1-yl)-5-fluoropyrimidin-4-yl)amino)methyl)-3-hydroxypiperidin-1-yl)acetamide, 2-(4-(((5-fluoro-6-(3-methyl-5-(3-(trifluoromethyl)phenyl)morpholino)pyrimidin-4-yl)amino)methyl)-3-hydroxypiperidin-1-yl)acetamide, 2-(4-(((5-fluoro-6-(3-methyl-5-(4-(trifluoromethyl)phenyl)morpholino)pyrimidin-4-yl)amino)methyl)-3-hydroxypiperidin-1-yl)acetamide, 2-(4-(((5-fluoro-6-(3-(4-(trifluoromethoxy)phenyl)morpholino)pyrimidin-4-yl)amino)methyl)piperidin-1-yl)acetamide, 2-(4-(((6-(4,4-difluoro-2-(4-(trifluoromethyl)phenyl)pyrrolidin-1-yl)-5-fluoropyrimidin-4-yl)amino)methyl)piperidin-1-yl)acetamide, 2-(4-(((5-fluoro-6-(2-(4-(trifluoromethyl)phenyl)pyrrolidin-1-yl)pyrimidin-4-yl)amino)methyl)piperidin-1-yl)acetamide, 2-(4-(((5-fluoro-6-(2-(2-hydroxy-4-(trifluoromethyl)phenyl)pyrrolidin-1-yl)pyrimidin-4-yl)amino)methyl)piperidin-1-yl)acetamide, 2-(4-(((5-fluoro-6-(4-fluoro-2-(4-(trifluoromethyl)phenyl)pyrrolidin-1-yl)pyrimidin-4-yl)amino)methyl)piperidin-1-yl)acetamide, 2-(4-(((5-fluoro-6-(2-(4-(trifluoromethyl)phenyl)azetidin-1-yl)pyrimidin-4-yl)amino)methyl)piperidin-1-yl)acetamide, 2-(4-(((6-(2-(4-chlorophenyl)pyrrolidin-1-yl)-5-fluoropyrimidin-4-yl)amino)methyl)-3-hydroxypiperidin-1-yl)acetamide, 2-(4-(((5-fluoro-6-(1-(6-(trifluoromethyl)pyridin-3-yl)-2-azabicyclo[3.1.0]hexan-2-yl)pyrimidin-4-yl)amino)methyl)-3-hydroxypiperidin-1-yl)acetamide, 2-(4-(((5-fluoro-6-(2-(6-(trifluoromethyl)pyridin-3-yl)-3-azabicyclo[3.1.0]hexan-3-yl)pyrimidin-4-yl)amino)methyl)-3-hydroxypiperidin-1-yl)acetamide, 2-(4-(((5-fluoro-6-(2-(4-(trifluoromethyl)phenyl)azetidin-1-yl)pyrimidin-4-yl)amino)methyl)-3-hydroxypiperidin-1-yl)acetamide, 2-(4-(((5-fluoro-6-(3-(2-fluoro-4-(trifluoromethyl)phenyl)morpholino)pyrimidin-4-yl)amino)methyl)-3-hydroxypiperidin-1-yl)acetamide, 2-(4-(((5-fluoro-6-(2-(2-fluoro-4-(trifluoromethyl)phenyl)pyrrolidin-1-yl)pyrimidin-4-yl)amino)methyl)-3-hydroxypiperidin-1-yl)acetamide, 2-(3-fluoro-4-(((5-fluoro-6-(2-(2-fluoro-4-(trifluoromethyl)phenyl)pyrrolidin-1-yl)-pyrimidin-4-yl)amino)methyl)piperidin-1-yl)acetamide, 2-(3-fluoro-4-(((5-fluoro-6-(3-(2-fluoro-4-(trifluoromethyl)phenyl)-morpholino)pyrimidin-4-yl)amino)methyl)piperidin-1-yl)acetamide, 2-(4-(((6-(4,4-difluoro-2-(2-fluoro-4-(trifluoromethyl)phenyl)pyrrolidin-1-yl)-5-fluoropyrimidin-4-yl)amino)methyl)-3-hydroxypiperidin-1-yl)acetamide, 2-(4-(((6-(4,4-difluoro-2-(2-fluoro-4-(trifluoromethyl)phenyl)pyrrolidin-1-yl)-5-fluoropyrimidin-4-yl)amino)methyl)-3-fluoropiperidin-1-yl)acetamide, 2-(3,3-difluoro-4-(((5-fluoro-6-(3-(2-fluoro-4-(trifluoromethyl)phenyl)-morpholino)pyrimidin-4-yl)amino)methyl)piperidin-1-yl)acetamide, 2-(3,3-difluoro-4-(((5-fluoro-6-(2-(2-fluoro-4-(trifluoromethyl)phenyl)pyrrolidin-1-yl)pyrimidin-4-yl)amino)methyl)piperidin-1-yl)acetamide, and 2-(4-(((6-(4,4-difluoro-2-(2-fluoro-4-(trifluoromethyl)phenyl)pyrrolidin-1-yl)-5-fluoropyrimidin-4-yl)amino)methyl)-3,3-difluoropiperidin-1-yl)acetamide.

In one embodiment, the compound or stereoisomer, or salt of the compound or stereoisomer is selected from the group consisting of:

2-((3R*,4R*)-4-(((5-fluoro-6-((S)-3-(4-(trifluoromethyl)phenyl)morpholino)pyrimidin-4-yl)amino)methyl)-3-hydroxypiperidin-1-yl)acetamide, 2-((R*)-3,3-difluoro-4-(((5-fluoro-6-((S)-3-(4-(trifluoromethyl)phenyl)morpholino)-pyrimidin-4-yl)amino)methyl)piperidin-1-yl)acetamide, 2-((3R*,4R*)-3-fluoro-4-(((5-fluoro-6-((S)-3-(4-(trifluoromethyl)phenyl)-morpholino)pyrimidin-4-yl)amino)methyl)piperidin-1-yl)acetamide, 2-((R*)-4-(((6-((R)-4,4-difluoro-2-(4-(trifluoromethyl)phenyl)pyrrolidin-1-yl)-5-fluoropyrimidin-4-yl)amino)methyl)-3,3-difluoropiperidin-1-yl)acetamide, 2-((3R*,4R*)-4-(((6-((R)-4,4-difluoro-2-(4-(trifluoromethyl)phenyl)pyrrolidin-1-yl)-5-fluoropyrimidin-4-yl)amino)methyl)-3-fluoropiperidin-1-yl)acetamide, and 2-((3R*,4R*)-4-(((6-((R)-4,4-difluoro-2-(4-(trifluoromethyl)phenyl)pyrrolidin-1-yl)-5-fluoropyrimidin-4-yl)amino)methyl)-3-hydroxypiperidin-1-yl)acetamide.

In one embodiment, the compound or stereoisomer, or salt of the compound or stereoisomer is selected from the group consisting of:

2-(4-(((5-fluoro-6-(3-(4-(trifluoromethyl)phenyl)morpholino)pyrimidin-4-yl)amino)methyl)-3-hydroxypiperidin-1-yl)acetamide, 2-(3,3-difluoro-4-(((5-fluoro-6-(3-(4-(trifluoromethyl)phenyl)morpholino)pyrimidin-4-yl)amino)methyl)piperidin-1-yl)acetamide, 2-(3-fluoro-4-(((5-fluoro-6-(3-(4-(trifluoromethyl)phenyl)morpholino)pyrimidin-4-yl)amino)methyl)piperidin-1-yl)acetamide, 2-(4-(((6-(4,4-difluoro-2-(4-(trifluoromethyl)phenyl)pyrrolidin-1-yl)-5-fluoropyrimidin-4-yl)amino)methyl)-3,3-difluoropiperidin-1-yl)acetamide, 2-(4-(((6-(4,4-difluoro-2-(4-(trifluoromethyl)phenyl)pyrrolidin-1-yl)-5-fluoropyrimidin-4-yl)amino)methyl)-3-fluoropiperidin-1-yl)acetamide, and 2-(4-(((6-(4,4-difluoro-2-(4-(trifluoromethyl)phenyl)pyrrolidin-1-yl)-5-fluoropyrimidin-4-yl)amino)methyl)-3-hydroxypiperidin-1-yl)acetamide.

In various cases, the compound, stereoisomer, or salt is selected from the group consisting of

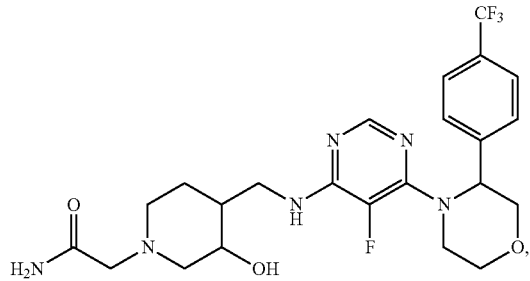

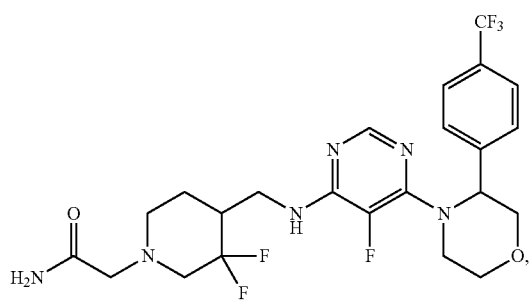

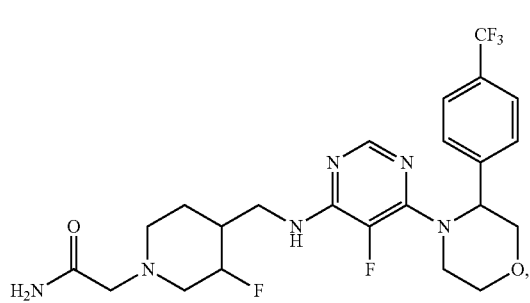

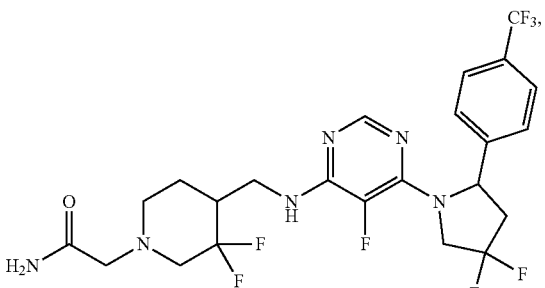

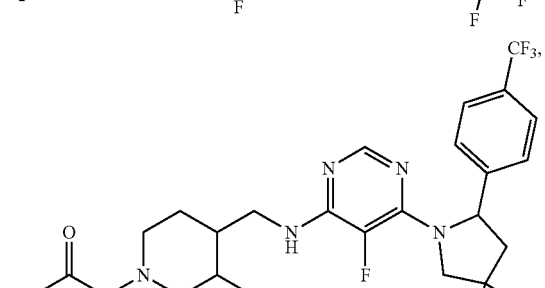

and

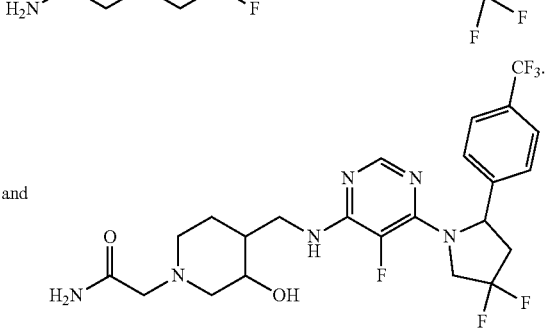

In some embodiments whenever a halogen is specified as a substituent the halogen is selected from fluoro or chloro.

Embodiments and particular disclosures used herein are to illustrate different alternatives of the disclosure and embodiments may be combined with other applicable embodiments.

Specific examples of compounds are disclosed in Table 1 below.

TABLE 1

Example compounds by Structure and Name.

| Ex. No. | Structure | Name |
|---|---|---|
| H6-1 | 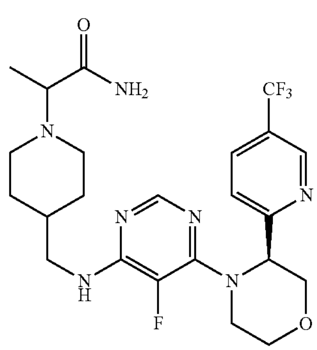 [SMILES: CC(C(N)=O)N1CCC(CNc2ncnc(N3CCOC[C@@H]3c3ccc(C(F)(F)F)cn3)c2F)CC1] | 2-(4-(((5-Fluoro-6-((S)-3-(5-trifluoromethyl)pyridin-2-yl)morpholino)pyrimidin-4-yl)amino)methyl)piperidin-1-yl)propanamide |

TABLE 1-continued

Example compounds by Structure and Name.

| Ex. No. | Structure | Name |
|---|---|---|
| H6-2 | 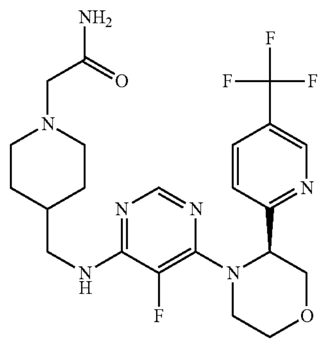 [SMILES: NC(=O)CN1CCC(CNc2ncnc(N3CCOC[C@@H]3c3ccc(C(F)(F)F)cn3)c2F)CC1] | (S)-2-(4-(((5-fluoro-6-(3-(5-(trifluoromethyl)pyridin-2-yl)morpholino)pyrimidin-4-yl)amino)methyl)piperidin-1-yl)acetamide |
| H6-3 | 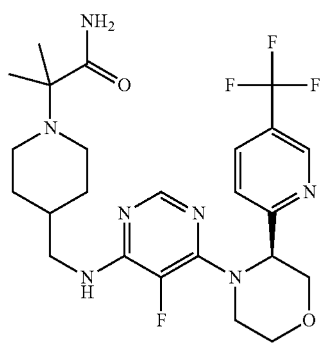 [SMILES: CC(C)(C(N)=O)N1CCC(CNc2ncnc(N3CCOC[C@@H]3c3ccc(C(F)(F)F)cn3)c2F)CC1] | (S)-2-(4-(((5-fluoro-6-(3-(5-(trifluoromethyl)pyridin-2-yl)morpholino)pyrimidin-4-yl)amino)methyl)piperidin-1-yl)-2-methylpropanamide |
| H6-4 | 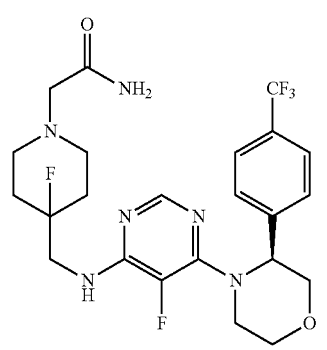 | (S)-2-(4-fluoro-4-(((5-fluoro-6-(3-(4-(trifluoromethyl)phenyl)morpholino)pyrimidin-4-yl)amino)methyl)piperidin-1-yl)acetamide |
| H6-5 | 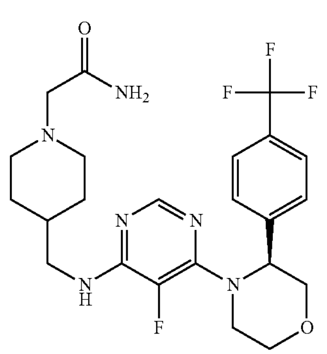 [SMILES: NC(=O)CN1CCC(CNc2ncnc(N3CCOC[C@@H]3c3ccc(C(F)(F)F)cc3)c2F)CC1] | (S)-2-(4-(((5-fluoro-6-(3-(4-(trifluoromethyl)phenyl)morpholino)pyrimidin-4-yl)amino)methyl)piperidin-1-yl)acetamide |

TABLE 1-continued

Example compounds by Structure and Name.

| Ex. No. | Structure | Name |
| --- | --- | --- |
| H6-6 | 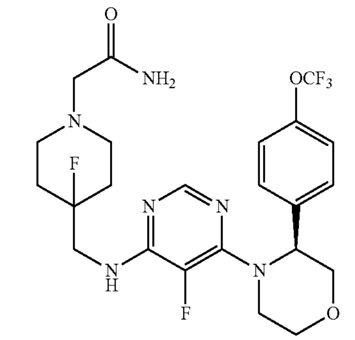 | (S)-2-(4-fluoro-4-(((5-fluoro-6-(3-(4-(trifluoromethoxy)phenyl)morpholino)pyrimidin-4-yl)amino)methyl)piperidin-1-yl)acetamide |
| H6-7 | 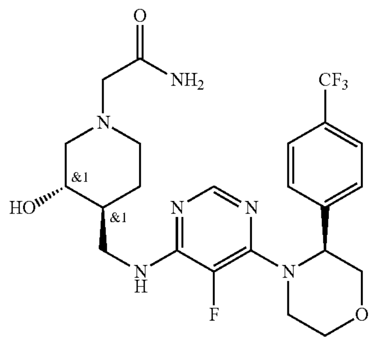 | 2-((3RS,4RS)-4-(((5-fluoro-6-((S)-3-(4-(trifluoromethyl)phenyl)morpholino)pyrimidin-4-yl)amino)methyl)-3-hydroxypiperidin-1-yl)acetamide |
| H6-7-1 | 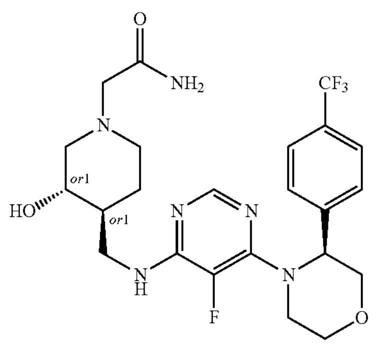 | 2-((3R*,4R*)-4-(((5-fluoro-6-((S)-3-(4-(trifluoromethyl)phenyl)morpholino)pyrimidin-4-yl)amino)methyl)-3-hydroxypiperidin-1-yl)acetamide 1$^{st}$ eluting isomer |
| H6-7-2 | | 2-((3R*,4R*)-4-(((5-fluoro-6-((S)-3-(4-(trifluoromethyl)phenyl)morpholino)pyrimidin-4-yl)amino)methyl)-3-hydroxypiperidin-1-yl)acetamide 2$^{nd}$ eluting isomer |
| H6-8 | 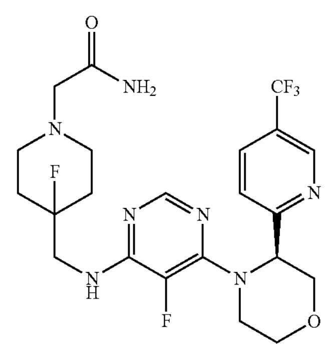 | (S)-2-(4-fluoro-4-(((5-fluoro-6-(3-(5-(trifluoromethyl)pyridin-2-yl)morpholino)pyrimidin-4-yl)amino)methyl)piperidin-1-yl)acetamide |

TABLE 1-continued

Example compounds by Structure and Name.

| Ex. No. | Structure | Name |
| --- | --- | --- |
| H6-9-1 | 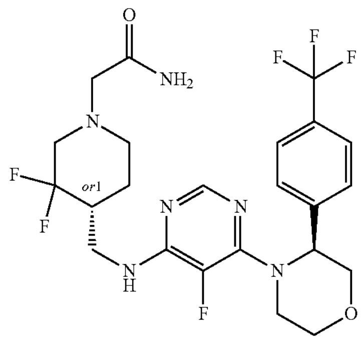 | 2-((R*)-3,3-difluoro-4-(((5-fluoro-6-((S)-3-(4-(trifluoromethyl)phenyl)morpholino)pyrimidin-4-yl)amino)methyl)piperidin-1-yl)acetamide<br>1st eluting isomer |
| H6-9-2 | | 2-((R*)-3,3-difluoro-4-(((5-fluoro-6-((S)-3-(4-(trifluoromethyl)phenyl)morpholino)pyrimidin-4-yl)amino)methyl)piperidin-1-yl)acetamide<br>2nd eluting isomer |
| H6-10-1 | 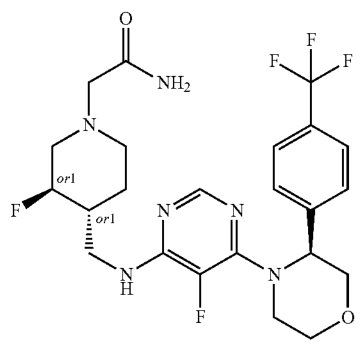 | 2-((3R*,4R*)-3-fluoro-4-(((5-fluoro-6-((S)-3-(4-(trifluoromethyl)phenyl)morpholino)pyrimidin-4-yl)amino)methyl)piperidin-1-yl)acetamide<br>1st eluting isomer |
| H6-10-2 | | 2-((3R*,4R*)-3-fluoro-4-(((5-fluoro-6-((S)-3-(4-(trifluoromethyl)phenyl)morpholino)pyrimidin-4-yl)amino)methyl)piperidin-1-yl)acetamide<br>2nd eluting isomer |
| H6-11-1 | 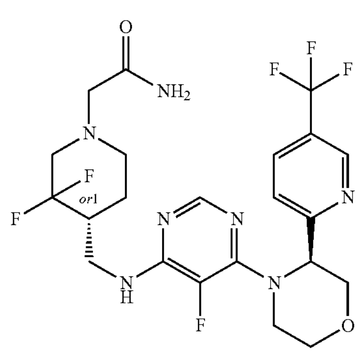 | 2-((R*)-3,3-difluoro-4-(((5-fluoro-6-((S)-3-(5-(trifluoromethyl)pyridin-2-yl)morpholino)pyrimidin-4-yl)amino)methyl)piperidin-1-yl)acetamide<br>1st eluting isomer |

TABLE 1-continued

Example compounds by Structure and Name.

| Ex. No. | Structure | Name |
|---|---|---|
| H6-11-2 | | 2-((R*)-3,3-difluoro-4-(((5-fluoro-6-((S)-3-(5-(trifluoromethyl)pyridin-2-yl)morpholino)pyrimidin-4-yl)amino)methyl)piperidin-1-yl)acetamide<br>2$^{nd}$ eluting isomer |
| H6-12-1 | 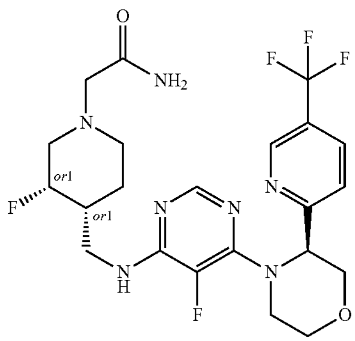 | 2-((3R*,4S*)-3-fluoro-4-(((5-fluoro-6-((S)-3-(5-(trifluoromethyl)pyridin-2-yl)morpholino)pyrimidin-4-yl)amino)methyl)piperidin-1-yl)acetamide<br>1$^{st}$ eluting isomer |
| H6-12-2 | | 2-((3R*,4S*)-3-fluoro-4-(((5-fluoro-6-((S)-3-(5-(trifluoromethyl)pyridin-2-yl)morpholino)pyrimidin-4-yl)amino)methyl)piperidin-1-yl)acetamide<br>2$^{nd}$ eluting isomer |
| H6-13-1 | 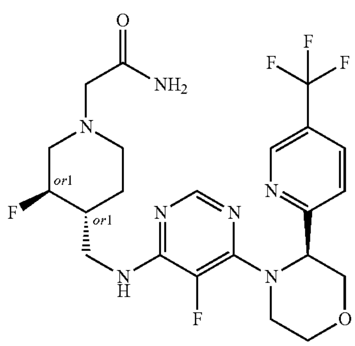 | 2-((3R*,4R*)-3-fluoro-4-(((5-fluoro-6-((S)-3-(5-(trifluoromethyl)pyridin-2-yl)morpholino)pyrimidin-4-yl)amino)methyl)piperidin-1-yl)acetamide<br>1$^{st}$ eluting isomer |
| H6-13-2 | | 2-((3R*,4R*)-3-fluoro-4-(((5-fluoro-6-((S)-3-(5-(trifluoromethyl)pyridin-2-yl)morpholino)pyrimidin-4-yl)amino)methyl)piperidin-1-yl)acetamide<br>2$^{nd}$ eluting isomer |
| H6-14 | 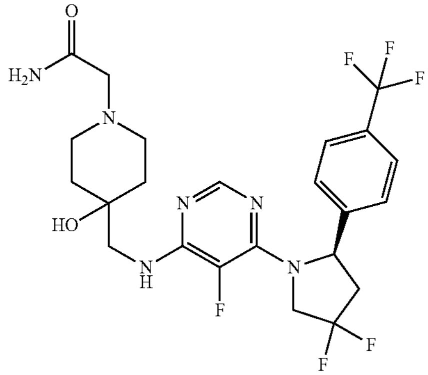 [SMILES: NC(=O)CN1CCC(O)(CNc2ncnc(N3CC(F)(F)C[C@@H]3c3ccc(C(F)(F)F)cc3)c2F)CC1] | (R)-2-(4-(((6-(4,4-difluoro-2-(4-(trifluoromethyl)phenyl)pyrrolidin-1-yl)-5-fluoropyrimidin-4-yl)amino)methyl)-4-hydroxypiperidin-1-yl)acetamide |

TABLE 1-continued

Example compounds by Structure and Name.

| Ex. No. | Structure | Name |
|---|---|---|
| H6-15-1 | 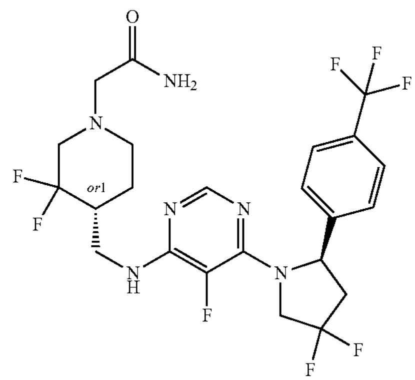 | 2-((R*)-4-(((6-((R)-4,4-difluoro-2-(4-(trifluoromethyl)phenyl)pyrrolidin-1-yl)-5-fluoropyrimidin-4-yl)amino)methyl)-3,3-difluoropiperidin-1-yl)acetamide<br>1$^{st}$ eluting isomer |
| H6-15-2 | | 2-((R*)-4-(((6-((R)-4,4-difluoro-2-(4-(trifluoromethyl)phenyl)pyrrolidin-1-yl)-5-fluoropyrimidin-4-yl)amino)methyl)-3,3-difluoropiperidin-1-yl)acetamide<br>2$^{nd}$ eluting isomer |
| H6-16-1 | 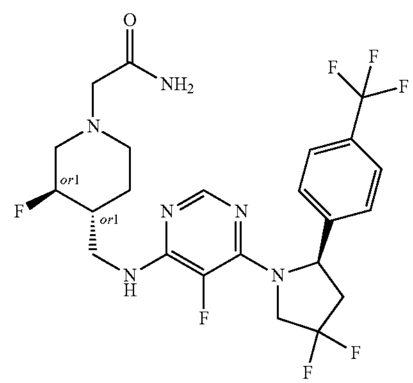 | 2-((3R*,4R*)-4-(((6-((R)-4,4-difluoro-2-(4-(trifluoromethyl)phenyl)pyrrolidin-1-yl)-5-fluoropyrimidin-4-yl)amino)methyl)-3-fluoropiperidin-1-yl)acetamide<br>1$^{st}$ eluting isomer |
| H6-16-2 | | 2-((3R*,4R*)-4-(((6-((R)-4,4-difluoro-2-(4-(trifluoromethyl)phenyl)pyrrolidin-1-yl)-5-fluoropyrimidin-4-yl)amino)methyl)-3-fluoropiperidin-1-yl)acetamide<br>2$^{nd}$ eluting isomer |
| H6-17 | 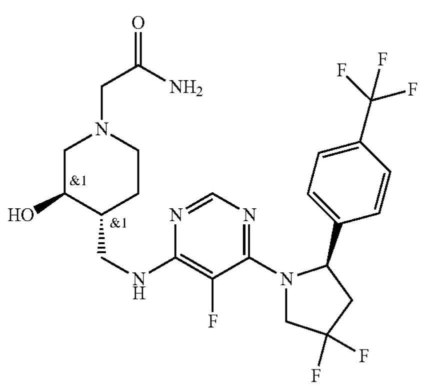 | 2-((3RS,4RS)-4-(((6-((R)-4,4-difluoro-2-(4-(trifluoromethyl)phenyl)pyrrolidin-1-yl)-5-fluoropyrimidin-4-yl)amino)methyl)-3-hydroxypiperidin-1-yl)acetamide |

TABLE 1-continued

Example compounds by Structure and Name.

| Ex. No. | Structure | Name |
|---|---|---|
| H6-17-1 | 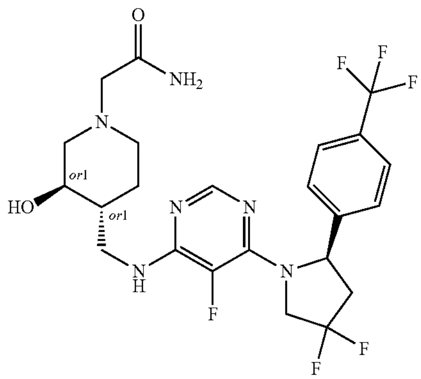 | 2-((3R*,4R*)-4-(((6-((R)-4,4-difluoro-2-(4-(trifluoromethyl)phenyl)pyrrolidin-1-yl)-5-fluoropyrimidin-4-yl)amino)methyl)-3-hydroxypiperidin-1-yl)acetamide<br>1st eluting isomer |
| H6-17-2 | | 2-((3R*,4R*)-4-(((6-((R)-4,4-difluoro-2-(4-(trifluoromethyl)phenyl)pyrrolidin-1-yl)-5-fluoropyrimidin-4-yl)amino)methyl)-3-hydroxypiperidin-1-yl)acetamide<br>2nd eluting isomer |
| H6-18-1 | 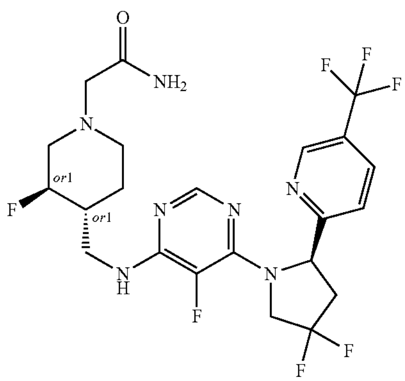 | 2-((3R*,4R*)-4-(((6-((R)-4,4-difluoro-2-(5-(trifluoromethyl)pyridin-2-yl)pyrrolidin-1-yl)-5-fluoropyrimidin-4-yl)amino)methyl)-3-fluoropiperidin-1-yl)acetamide<br>1st eluting isomer |
| H6-18-2 | | 2-((3R*,4R*)-4-(((6-((R)-4,4-difluoro-2-(5-(trifluoromethyl)pyridin-2-yl)pyrrolidin-1-yl)-5-fluoropyrimidin-4-yl)amino)methyl)-3-fluoropiperidin-1-yl)acetamide<br>2nd eluting isomer |
| H6-19-1 | 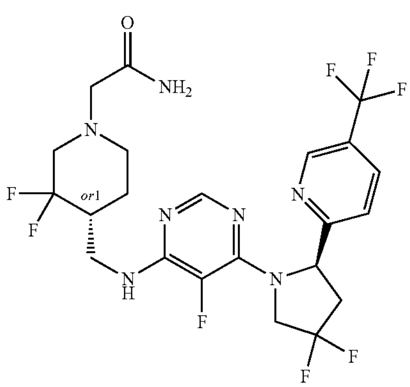 | 2-((R*)-4-(((6-((R)-4,4-difluoro-2-(5-(trifluoromethyl)pyridin-2-yl)pyrrolidin-1-yl)-5-fluoropyrimidin-4-yl)amino)methyl)-3,3-difluoro-piperidin-1-yl)acetamide<br>1st eluting isomer |
| H6-19-2 | | 2-((R*)-4-(((6-((R)-4,4-difluoro-2-(5-(trifluoromethyl)pyridin-2-yl)pyrrolidin-1-yl)-5-fluoropyrimidin-4-yl)amino)methyl)-3,3-difluoro-piperidin-1-yl)acetamide<br>2nd eluting isomer |

TABLE 1-continued

Example compounds by Structure and Name.

| Ex. No. | Structure | Name |
|---|---|---|
| H6-20 | 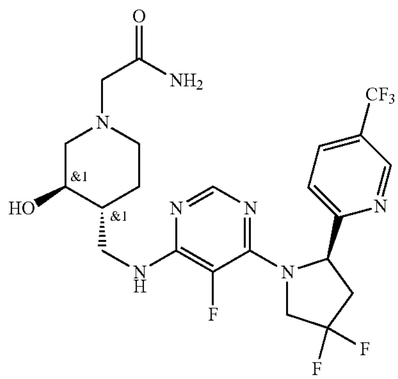 | 2-((3RS,4RS)-4-(((6-((R)-4,4-difluoro-2-(5-(trifluoromethyl)pyridin-2-yl)pyrrolidin-1-yl)-5-fluoropyrimidin-4-yl)amino)methyl)-3-hydroxy-piperidin-1-yl)acetamide |
| H6-21-1 | 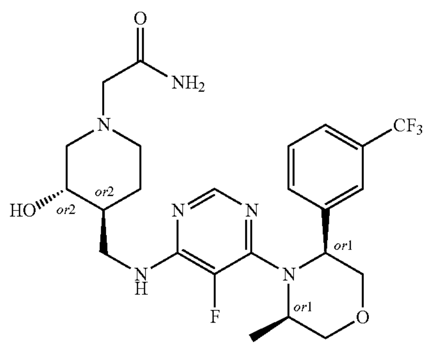 | rel-2-((3R,4R)-4-(((5-fluoro-6-((3S,5R)-3-methyl-5-(3-(trifluoromethyl)phenyl)morpholino)pyrimidin-4-yl)amino)methyl)-3-hydroxypiperidin-1-yl)acetamide<br>OR<br>rel-2-((3R,4R)-4-(((5-fluoro-6-((3R,5S)-3-methyl-5-(3-(trifluoromethyl)phenyl)morpholino)pyrimidin-4-yl)amino)methyl)-3-hydroxypiperidin-1-yl)acetamide<br>1st eluting isomer |
| H6-21-2 | | rel-2-((3R,4R)-4-(((5-fluoro-6-((3S,5R)-3-methyl-5-(3-(trifluoromethyl)phenyl)morpholino)pyrimidin-4-yl)amino)methyl)-3-hydroxypiperidin-1-yl)acetamide<br>OR<br>rel-2-((3R,4R)-4-(((5-fluoro-6-((3R,5S)-3-methyl-5-(3-(trifluoromethyl)phenyl)morpholino)pyrimidin-4-yl)amino)methyl)-3-hydroxypiperidin-1-yl)acetamide<br>2nd eluting isomer |
| H6-21-3 | | rel-2-((3R,4R)-4-(((5-fluoro-6-((3S,5R)-3-methyl-5-(3-(trifluoromethyl)phenyl)morpholino)pyrimidin-4-yl)amino)methyl)-3-hydroxypiperidin-1-yl)acetamide<br>OR<br>rel-2-((3R,4R)-4-(((5-fluoro-6-((3R,5S)-3-methyl-5-(3-(trifluoromethyl)phenyl)morpholino)pyrimidin-4-yl)amino)methyl)-3-hydroxypiperidin-1-yl)acetamide<br>1st eluting isomer |
| H6-21-4 | | rel-2-((3R,4R)-4-(((5-fluoro-6-((3S,5R)-3-methyl-5-(3-(trifluoromethyl)phenyl)morpholino)pyrimidin-4-yl)amino)methyl)-3-hydroxypiperidin-1-yl)acetamide<br>OR<br>rel-2-((3R,4R)-4-(((5-fluoro-6-((3R,5S)-3-methyl-5-(3-(trifluoromethyl)phenyl)morpholino)pyrimidin-4-yl)amino)methyl)-3-hydroxypiperidin-1-yl)acetamide<br>2nd eluting isomer |

TABLE 1-continued

Example compounds by Structure and Name.

| Ex. No. | Structure | Name |
|---|---|---|
| H6-22-1 | 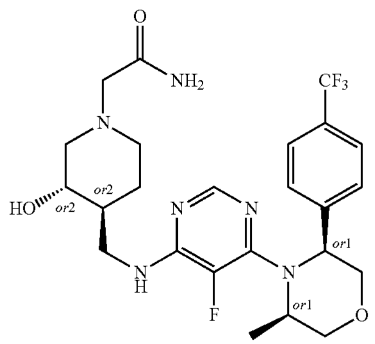 | rel-2-((3R,4R)-4-(((5-fluoro-6-((3S,5R)-3-methyl-5-(4-(trifluoromethyl)phenyl)morpholino)pyrimidin-4-yl)amino)methyl)-3-hydroxypiperidin-1-yl)acetamide OR rel-2-((3R,4R)-4-(((5-fluoro-6-((3R,5S)-3-methyl-5-(4-(trifluoromethyl)phenyl)morpholino)pyrimidin-4-yl)amino)methyl)-3-hydroxypiperidin-1-yl)acetamide 1$^{st}$ eluting isomer |
| H6-22-2 | | rel-2-((3R,4R)-4-(((5-fluoro-6-((3S,5R)-3-methyl-5-(4-(trifluoromethyl)phenyl)morpholino)pyrimidin-4-yl)amino)methyl)-3-hydroxypiperidin-1-yl)acetamide OR rel-2-((3R,4R)-4-(((5-fluoro-6-((3R,5S)-3-methyl-5-(4-(trifluoromethyl)phenyl)morpholino)pyrimidin-4-yl)amino)methyl)-3-hydroxypiperidin-1-yl)acetamide 2$^{nd}$ eluting isomer |
| H6-22-3 | | rel-2-((3R,4R)-4-(((5-fluoro-6-((3S,5R)-3-methyl-5-(4-(trifluoromethyl)phenyl)morpholino)pyrimidin-4-yl)amino)methyl)-3-hydroxypiperidin-1-yl)acetamide OR rel-2-((3R,4R)-4-(((5-fluoro-6-((3R,5S)-3-methyl-5-(4-(trifluoromethyl)phenyl)morpholino)pyrimidin-4-yl)amino)methyl)-3-hydroxypiperidin-1-yl)acetamide 1$^{st}$ eluting isomer |
| H6-22-4 | | rel-2-((3R,4R)-4-(((5-fluoro-6-((3S,5R)-3-methyl-5-(4-(trifluoromethyl)phenyl)morpholino)pyrimidin-4-yl)amino)methyl)-3-hydroxypiperidin-1-yl)acetamide OR rel-2-((3R,4R)-4-(((5-fluoro-6-((3R,5S)-3-methyl-5-(4-(trifluoromethyl)phenyl)morpholino)pyrimidin-4-yl)amino)methyl)-3-hydroxypiperidin-1-yl)acetamide 2$^{nd}$ eluting isomer |
| H6-23 | 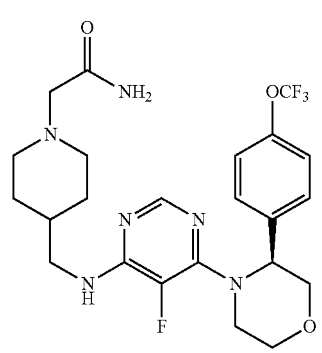 [SMILES: NC(=O)CN1CCC(CNc2ncnc(N3CCOC[C@@H]3c3ccc(OC(F)(F)F)cc3)c2F)CC1] | (S)-2-(4-(((5-fluoro-6-(3-(4-(trifluoromethoxy)phenyl)morpholino)pyrimidin-4-yl)amino)methyl)piperidin-1-yl)acetamide |

TABLE 1-continued

Example compounds by Structure and Name.

| Ex. No. | Structure | Name |
|---|---|---|
| H6-24 | 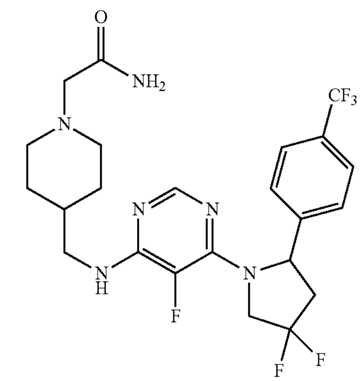 [SMILES: NC(=O)CN1CCC(CNc2ncnc(N3CC(F)(F)CC3c3ccc(C(F)(F)F)cc3)c2F)CC1] | 2-(4-(((6-(4,4-difluoro-2-(4-(trifluoromethyl)phenyl)pyrrolidin-1-yl)-5-fluoropyrimidin-4-yl)amino)methyl)piperidin-1-yl)acetamide |
| H6-25 | 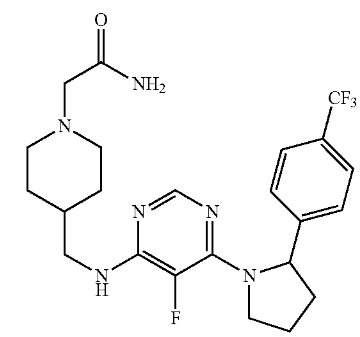 [SMILES: NC(=O)CN1CCC(CNc2ncnc(N3CCCC3c3ccc(C(F)(F)F)cc3)c2F)CC1] | 2-(4-(((5-fluoro-6-(2-(4-(trifluoromethyl)phenyl)pyrrolidin-1-yl)pyrimidin-4-yl)amino)methyl)piperidin-1-yl)acetamide |
| H6-25-1 | 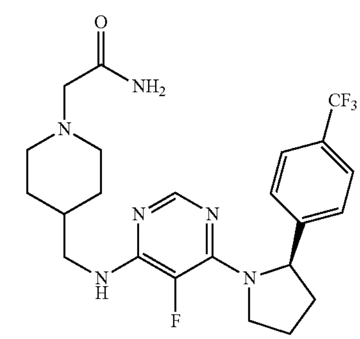 [SMILES: NC(=O)CN1CCC(CNc2ncnc(N3CCC[C@@H]3c3ccc(C(F)(F)F)cc3)c2F)CC1] | (R)-2-(4-(((5-fluoro-6-(2-(4-(trifluoromethyl)phenyl)pyrrolidin-1-yl)pyrimidin-4-yl)amino)methyl)piperidin-1-yl)acetamide |
| H6-26 | 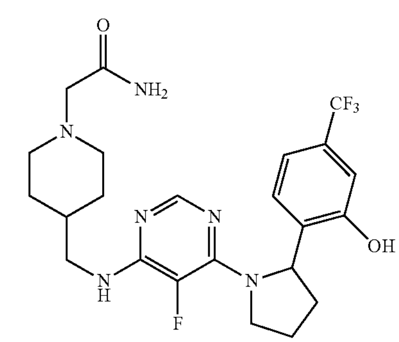 [SMILES: NC(=O)CN1CCC(CNc2ncnc(N3CCCC3c3ccc(C(F)(F)F)cc3O)c2F)CC1] | 2-(4-(((5-fluoro-6-(2-(2-hydroxy-4-(trifluoromethyl)phenyl)pyrrolidin-1-yl)pyrimidin-4-yl)amino)methyl)piperidin-1-yl)acetamide |

TABLE 1-continued

Example compounds by Structure and Name.

| Ex. No. | Structure | Name |
|---|---|---|
| H6-27 | 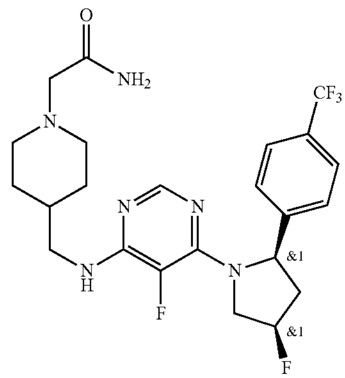 | rac-2-(4-(((5-fluoro-6-((2R,4R)-4-fluoro-2-(4-(trifluoromethyl)phenyl)pyrrolidin-1-yl)pyrimidin-4-yl)amino)methyl)piperidin-1-yl)acetamide |
| H6-28 | 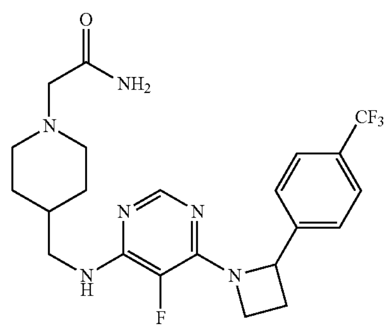 [SMILES: NC(=O)CN1CCC(CNc2ncnc(N3CCC3c3ccc(C(F)(F)F)cc3)c2F)CC1] | 2-(4-(((5-fluoro-6-(2-(4-(trifluoromethyl)phenyl)azetidin-1-yl)pyrimidin-4-yl)amino)methyl)piperidin-1-yl)acetamide |
| H6-29 | 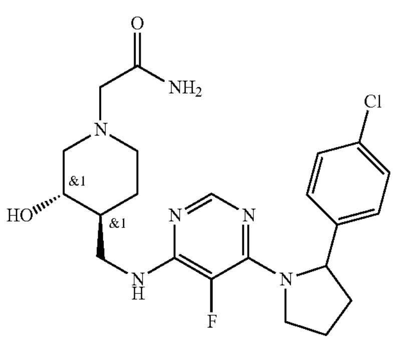 | rac-2-((3R,4R)-4-(((6-(2-(4-chlorophenyl)pyrrolidin-1-yl)-5-fluoropyrimidin-4-yl)amino)methyl)-3-hydroxypiperidin-1-yl)acetamide |
| H6-30 | 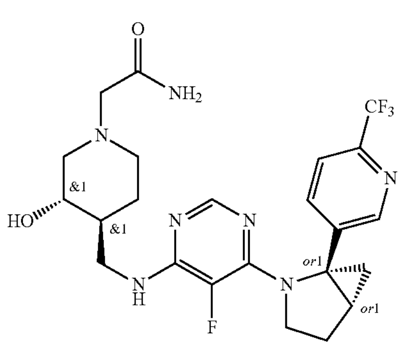 | 2-((3RS,4RS)-4-(((5-fluoro-6-((1S*,5R*)-1-(6-(trifluoromethyl)pyridin-3-yl)-2-azabicyclo[3.1.0]hexan-2-yl)pyrimidin-4-yl)amino)methyl)-3-hydroxypiperidin-1-yl)acetamide |

TABLE 1-continued

Example compounds by Structure and Name.

| Ex. No. | Structure | Name |
|---|---|---|
| H6-31 | 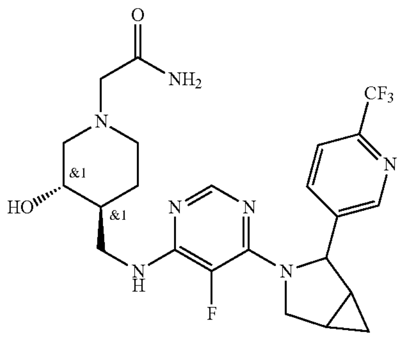 | rac-2-((3R,4R)-4-(((5-fluoro-6-(2-(6-(trifluoromethyl)pyridin-3-yl)-3-azabicyclo[3.1.0]hexan-3-yl)pyrimidin-4-yl)amino)methyl)-3-hydroxypiperidin-1-yl)acetamide |
| H6-32 | 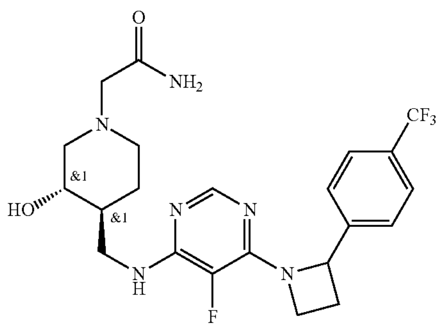 | rac-2-((3R,4R)-4-(((5-fluoro-6-(2-(4-(trifluoromethyl)phenyl)azetidin-1-yl)pyrimidin-4-yl)amino)methyl)-3-hydroxypiperidin-1-yl)acetamide |
| H6-100 | 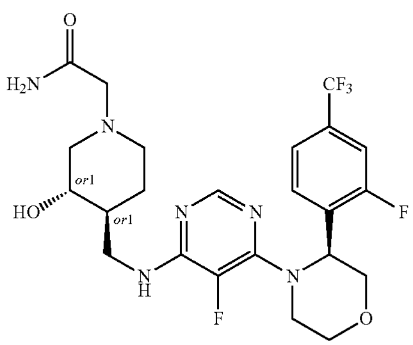 | 2-((3R*,4R*)-4-(((5-fluoro-6-((S)-3-(2-fluoro-4-(trifluoromethyl)phenyl)morpholino)pyrimidin-4-yl)amino)methyl)-3-hydroxypiperidin-1-yl)acetamide |
| H6-101 | 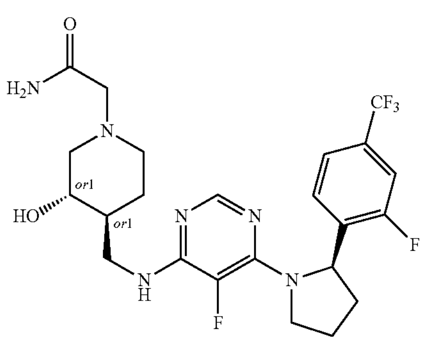 | 2-((3R*,4R*)-4-(((5-fluoro-6-(®-2-(2-fluoro-4-(trifluoromethyl)phenyl)53yrrolidine-1-yl)pyrimidin-4-yl)amino)methyl)-3-hydroxypiperidin-1-yl)acetamide |

TABLE 1-continued

Example compounds by Structure and Name.

| Ex. No. | Structure | Name |
|---|---|---|
| H6-102 | 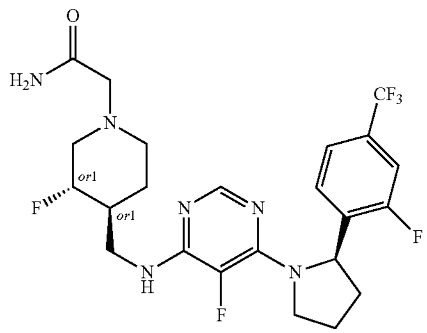 | 2-((3R*,4R*)-3-fluoro-4-(((5-fluoro-6-((R)-2-(2-fluoro-4-(trifluoromethyl)phenyl)pyrrolidin-1-yl)pyrimidin-4-yl)amino)methyl)piperidin-1-yl)acetamide |
| H6-103 | 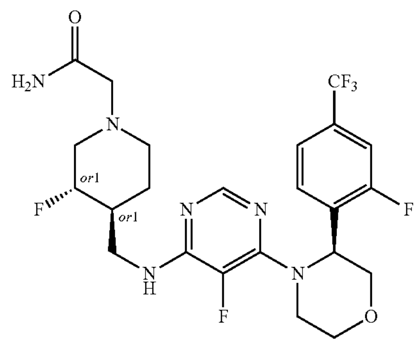 | 2-((3R*,4R*)-3-fluoro-4-(((5-fluoro-6-((S)-3-(2-fluoro-4-(trifluoromethyl)phenyl)morpholino)pyrimidin-4-yl)amino)methyl)piperidin-1-yl)acetamide |
| H6-104 | 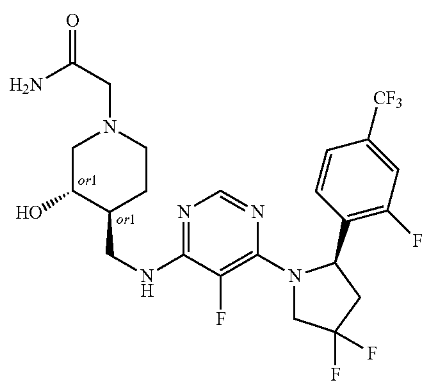 | 2-((3R*,4R*)-4-(((6-(®-4,4-difluoro-2-(2-fluoro-4-(trifluoromethyl)phenyl)53yrrolidine-1-yl)-5-fluoropyrimidin-4-yl)amino)methyl)-3-hydroxypiperidin-1-yl)acetamide |
| H6-105 | 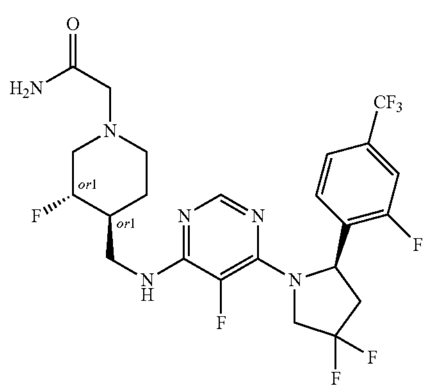 | 2-((3R*,4R*)-4-(((6-((R)-4,4-difluoro-2-(2-fluoro-4-(trifluoromethyl)phenyl)pyrrolidin-1-yl)-5-fluoropyrimidin-4-yl)amino)methyl)-3-fluoropiperidin-1-yl)acetamide |

TABLE 1-continued

Example compounds by Structure and Name.

| Ex. No. | Structure | Name |
|---|---|---|
| H6-106 | 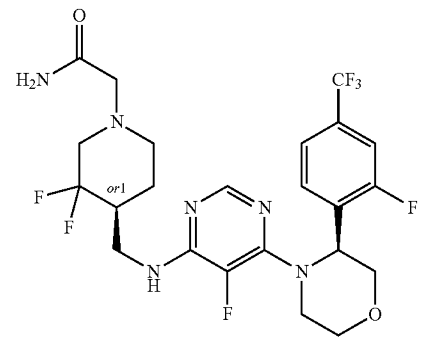 | 2-((R*)-3,3-difluoro-4-(((5-fluoro-6-((S)-3-(2-fluoro-4-(trifluoromethyl)phenyl)morpholino)pyrimidin-4-yl)amino)methyl)piperidin-1-yl)acetamide |
| H6-107 | 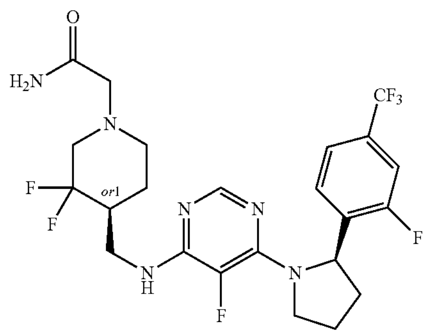 | 2-((R*)-3,3-difluoro-4-(((5-fluoro-6-((R)-2-(2-fluoro-4-(trifluoromethyl)phenyl)pyrrolidin-1-yl)pyrimidin-4-yl)amino)methyl)piperidin-1-yl)acetamide |
| H6-108 | 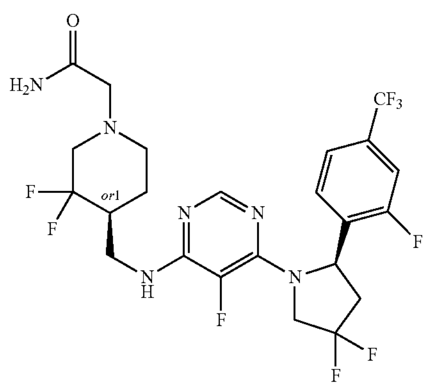 | 2-((R*)-4-(((6-((R)-4,4-difluoro-2-(2-fluoro-4-(trifluoromethyl)phenyl)pyrrolidin-1-yl)-5-fluoropyrimidin-4-yl)amino)methyl)-3,3-difluoropiperidin-1-yl)acetamide |

In a related aspect there is provided a prodrug of a compound of Formula (I) as described herein.

The compounds of the present disclosure are active, e.g. having a RORγ Gal4<1000 nM, such as <500 nM, such as <100 nM, and have a log P substantially lower (e.g. a decreased log P of 1.5, such as 2.0, such as 2.5 log units) than compounds disclosed in WO2016020288 and WO2016020295. In certain embodiments Log D and Log P are substantially lower than compounds in WO2016020288 and WO2016020295. The compounds disclosed herein thus have an improved lipophilicity at similar potency. The compounds disclosed herein may thus be improved modulators of RORγ, e.g. having an attractive interaction (e.g. higher binding ability) to the hydrophobic binding sites of the ligand binding domain (LBD) of the RORγ and a low log P and/or low log D.

Pharmaceutical Compositions

In another aspect, the present disclosure relates to a pharmaceutical composition comprising physiologically acceptable surface active agents, carriers, diluents, excipients, smoothing agents, suspension agents, film forming substances, and coating assistants, or a combination thereof; and a compound as disclosed herein, e.g., a compound of Formulae (I), (II), and (III) as disclosed herein, or a salt, stereoisomer, or salt of a stereoisomer thereof. The compound of Formulae (I), (II), and (III) included in the pharmaceutical composition may also be any compound of the preferred embodiments described above. In another aspect, the present disclosure relates to a pharmaceutical composition comprising physiologically acceptable surface active agents, carriers, diluents, excipients, smoothing agents, suspension agents, film forming substances, and coating assistants, or a combination thereof; and a compound of any one of Formulae I, II or III as disclosed herein. Acceptable carriers or diluents, as well as other additives to be combined with one or more compound(s) of Formula I, II or III as disclosed herein to provide a pharmaceutical composition, for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives, stabilizers, dyes, sweeteners, fragrances, flavoring agents, taste masking agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

The term "pharmaceutical composition" refers to a mixture of a compound disclosed herein with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Similar, pharmaceutical compositions can also be obtained by reacting compounds with inorganic or organic bases, such as ammonia, sodium carbonate, sodium hydrogen carbonate, sodium hydroxide, and the like.

The term "carrier" defines a chemical compound that facilitates the incorporation of a compound into cells or tissues. For example, and without limitation dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

The term "physiologically acceptable" defines a carrier or diluent that does not abrogate the biological activity and properties of the compound.

The pharmaceutical compositions described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., 18th edition, 1990.

Suitable routes of administration may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal, or intraocular injections. The compounds can also be administered in sustained or controlled release dosage forms, including depot injections, osmotic pumps, pills, transdermal (including electrotransport) patches, and the like, for prolonged and/or timed, pulsed administration at a predetermined rate.

The pharmaceutical compositions may be manufactured in a manner that is itself known, e.g., by means of conventional mixing, dissolving, granulating, dragee-making, levigating, emulsifying, encapsulating, entrapping or tableting processes.

Pharmaceutical compositions for use as described herein may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations (for example, liposomes), may be utilized.

For transmucosal administration, penetrants appropriate to the barrier to be permeated may be used in the formulation.

Pharmaceutical formulations for parenteral administration, e.g., by bolus injection or continuous infusion, include aqueous solutions of the active compounds in water-soluble form. Additionally, suspensions of the active compounds may be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

For oral administration, the compounds can be formulated readily by combining the active compounds with pharmaceutically acceptable carriers well known in the art. Such carriers enable the compounds disclosed herein to be formulated as tablets, pills, dragees, capsules, liquids, gels, syrups, slurries, suspensions and the like, for oral ingestion by a patient to be treated. Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use as described herein are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Further disclosed herein are various pharmaceutical compositions well known in the pharmaceutical art for uses that include intraocular, intranasal, and intraauricular delivery. Suitable penetrants for these uses are generally known in the art. Topical ophthalmic compositions may be formulated as a solution in water buffered at a pH of 5.0 to 8.0. Other ingredients that may be desirable to use in the ophthalmic preparations include preservatives (such as benzalkonium chloride, stabilized oxychloro complex, which is sold as Purite™, or stabilized chlorine dioxide), cosolvents (such as polysorbate 20, 60 and 80, Pluronic® F-68, F-84 and P-103, cyclodextrin, or Solutol) and viscosity-building agents (such as polyvinyl alcohol, polyvinyl pyrrolidone, methyl cellulose, hydroxypropyl methyl cellulose, hydroxyethyl cellulose, carboxymethyl cellulose, or hydroxypropyl cellulose). The compounds disclosed herein may also be used in an intraocular implant as described in U.S. Pat. No. 7,931,909 which is hereby incorporated by reference. Pharmaceutical compositions for intraocular delivery include aqueous ophthalmic solutions of the active compounds in water-soluble form, such as eyedrops, or in gellan gum (Shedden et al., Clin. Ther., 23(3):440-50 (2001)) or hydrogels (Mayer et al., Ophthalmologica, 210(2): 101-3 (1996)); ophthalmic ointments; ophthalmic suspensions, such as microparticulates, drug-containing small polymeric particles that are suspended in a liquid carrier medium (Joshi, A., J. Ocul. Pharmacol., 10(1):29-45 (1994)), lipid-soluble formulations (Alm et al., Prog. Clin. Biol. Res., 312:447-58 (1989)), and microspheres (Mordenti, Toxicol. Sci., 52(1): 101-6 (1999)); and ocular inserts. All of the above-mentioned references, are incorporated herein by reference in their entireties. Such suitable pharmaceutical formulations for intraocular delivery are most often and preferably formulated to be sterile, isotonic and buffered for stability and comfort. Pharmaceutical compositions for intranasal delivery may also include drops and sprays often prepared to simulate in many respects nasal secretions to ensure maintenance of normal ciliary action. As disclosed in Remington's Pharmaceutical Sciences, 18th Ed., Mack Publishing Co., Easton, Pa. (1990), which is incorporated herein by reference in its entirety, and well-known to those skilled in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intraauricular delivery include suspensions and ointments for topical application in the ear. Common solvents for such aural formulations include glycerin and water.

The compounds disclosed herein may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For hydrophobic compounds, a suitable pharmaceutical carrier may be a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Agents intended to be administered intracellularly may be administered using techniques well known to those of ordinary skill in the art. For example, such agents may be encapsulated into liposomes. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. The liposome may be coated with a tissue-specific antibody. The liposomes will be targeted to and taken up selectively by the desired organ. Alternatively, small hydrophobic organic molecules may be directly administered intracellularly.

Additional therapeutic or diagnostic agents may be incorporated into the pharmaceutical compositions. Alternatively or additionally, pharmaceutical compositions may be combined with other compositions that contain other therapeutic or diagnostic agents.

Combinations

The compounds disclosed herein may also be combined with other active compounds in the treatment and/or prevention of inflammatory, metabolic, oncologic and autoimmune diseases or disorders or a symptom thereof.

The combinations provided herein comprise the compounds disclosed herein and one or more additional active substances, such as:

a) Corticosteroids, such as prednisone, methylprednisolone or beta-methasone;
b) Immunosuppressants, such as cyclosporine, tacrolimus methotrexate, hydroxyurea, mycophenolate mofetil, mycophenolic acid, sulfasalazine, 6-thioguanine or azathioprine;
c) Fumaric acid esters, such as dimethyl fumarate;
d) Dihydroorotate dehydrogenase (DHODH) inhibitors such as leflunomide;
e) Retinoids, such as acitretin or isotretinoin;
f) Anti-inflammatories such as apremilast, crisaborole, celecoxib, diclofenac, aceclofenac, aspirin or naproxen;
g) JAK inhibitors such as tofacitinib, baricitinib, upadacitinib, ruxolitinib or delgocitinib;
h) Antibiotics such as gentamicin;
i) Anti-cancer agents such as lenalidomide, pomalidomide, pembrolizumab, nivolumab, daratumumab, bortezomib, carfilzomib, ixazomib, bendamustine or ventoclast;
j) T-cell blockers such as alefacept or efalizumab;
k) Tumor necrosis factor-alpha (TNF-alpha) blockers such as etanercept, adalimumab, infliximab, golimumab, certolizumab pegol;
l) interleukin 12/23 blockers such as ustekinumab;
m) IL-23 blockers such as risankizumab, guselkumab or tildrakizumab;
n) anti-IL4/IL13 antagonist such as dupilumab, lebrikizumab or tralokinumab;
o) IL-113 blockers such as canakinumab;
p) IL-alpha blockers such as bermekimab;
q) CD6 blockers such as itolizumab;
r) IL-36R blockers such as BI-655130 or bimekizumab;
s) IL-6 antagonist such as tocilizumab;
t) Calcineurin inhibitors such as pimecrolimus, tacrolimus or cyclosporine;
u) Phototherapy agents such as psoralen, methoxypsoralen or 5-methoxypsoralen+UVA (PUVA) or treatment with UVB (with or without tar);
v) Fixed combinations of corticosteroids and vitamin D derivatives;
w) Fixed combinations of corticosteroids and retinoids;
x) Corticosteroid tapes; and
y) an agent selected from BMS986165, PF-06700841, PF-06826647, piclidenoson, tepilamide fumarate, LYC-30937, LEO-32731, BI-730357, PRCL-02, LNP-1955, GSK-2982772, CBP-307, KD-025, MP-1032, petesicatib, JTE-451, Hemay-005, SM-04755, EDP-1815, BI-730460, SFA-002 ER, JNJ-3534, SAR-441169, BOS-172767, SCD-044, ABBV-157, BAY-1834845, AUR-101, R-835, PBF-1650, RTA-1701, AZD-0284, mirikizumab, CD20 antagonist, salicylic acid, coal tar, Mical-1, DUR-928, AM-001, BMX-010, TA-102, SNA-125, brepocitinib tosylate, pegcantratinib, ESR-114, NP-000888, SM-04755, BOS-475, SB-414, LEO-134310, CBS-3595, PF-06763809, XCUR-17 or BTX-1308.

The active compounds in the combination, i.e the compounds provided herein, and the other optional active compounds may be administered together in the same pharmaceutical composition or in different compositions intended for separate, simultaneous, concomitant or sequential administration by the same or a different route.

Uses

The compounds or pharmaceutical compositions disclosed herein as described above may be used to modulate the activity of a retinoic acid receptor-related orphan receptor (ROR), such as a RORα, RORβ and/or RORγ receptor. Modulators of RORγ have been reviewed by B. Fauber and S. Magnuson in J. Med. Chem., Feb. 6, 2014, and Pandya et al in J. Med. Chem. 2018, 61, 24, 10976-10995 which hereby are incorporated by reference in its entirety. Examples of RORγ receptors are RORγ1 and RORγt receptors. The compounds or pharmaceutical compositions as described above may also display selective modulation of a particular ROR receptor relative to a different ROR receptor. For example, according to some embodiments disclosed herein some compounds or pharmaceutical compositions modulate the activity of an RORγ receptor to a larger extent than they modulate the activity of RORα and/or RORβ receptors.

The compounds or pharmaceutical compositions disclosed herein may also be used to modulate the activity of cells producing IL-17A in a RORγt dependent manner, for example, γδT cells, Th17 cells, Tc17 cells and ILC3 cells. The compounds or pharmaceutical compositions disclosed herein may also be used to inhibit RORγt function upon IL-23 stimulation, which in turn negatively impacts on the differentiation and expansion of pathogenic Tc17 and Th17.

Publications providing useful background information are Arthritis & Rheumatism, 2014, 66, 579-588; Curr Top Microbial Immun, 2014, 378, 171-182; Drug Disc. Today, 2014, May; Nature Rev. Drug Disc. 2012, 11, 763-776, and Nature Rev. Drug Disc., 2014, 13, 197-216, all of which are hereby incorporated by reference in their entirety.

The compounds or pharmaceutical compositions as described herein and above may also be used in therapy or may be used to treat inflammatory, metabolic, oncologic and autoimmune diseases or disorders or a symptom thereof. Examples of such diseases or disorders are inflammatory, metabolic, oncologic and autoimmune diseases or disorders mediated or affected by IL-17A and/or RORγ. The role of RORγ in the pathogenesis of autoimmune or inflammatory diseases has been disclosed in Immunity 2007, 26(5), 643-654; Nat. Rev. Immunol. 2006, 6, 205-217; J. Immunol. 2009, 183, 7169-7177; Brain Pathol. 2004, 14, 164-174; Brain 2007, 130, 1089-1104; and Nat Rev. Immunol. 2008, 8, 183-192 all of which are hereby incorporated by reference in their entirety.

More specific examples of diseases or disorders, or a symptom thereof include asthma, acne, chronic obstructive pulmonary disease (COPD), bronchitis, atherosclerosis, *Helicobacter pylori* infection, allergic diseases including allergic rhinitis, allergic conjunctivitis and uveitis, sprue and food allergy, atopic dermatitis, lichen planus, cystic fibrosis, lung allograph rejection, multiple sclerosis, rheumatoid arthritis, juvenile idiopathic arthritis, osteoarthritis, ankylosing spondylitis, psoriasis, psoriatic arthritis, ichtyoses, bullous diseases, hidradenitis suppurativa, steatosis, steatohepatitis, non-alcoholic fatty liver disease (NAFLD), non-alcoholic steatohepatitis (NASH), lupus erythematosus, Hashimoto's disease, pancreatitis, autoimmune diabetes, autoimmune ocular disease, ulcerative colitis, colitis, Crohn's disease, inflammatory bowel disease (IBD), inflammatory bowel syndrome (IBS), Sjogren's syndrome, optic neuritis, type I diabetes, neuromyelitis optica, Myasthenia Gravis, Guillain-Barre syndrome, Graves' disease, scleritis, obesity, obesity-induced insulin resistance, type II diabetes and cancer.

More preferably, the diseases or disorders, or a symptom thereof include acne, atopic dermatitis, lichen planus, multiple sclerosis, rheumatoid arthritis, juvenile idiopathic arthritis, osteoarthritis, ankylosing spondylitis, psoriasis, psoriatic arthritis, ichthyoses, bullous diseases, hidradenitis suppurativa, ulcerative colitis, colitis, Crohn's disease, inflammatory bowel disease (IBD) and lupus erythematosus.

An example of a symptom is a physical or mental feature which is regarded as indicating a condition of disease, particularly such a feature that is apparent to the patient, e.g. treating o preventing a symptom is not considered disease-modifying but preventing or alleviating one or more symptoms commonly experience in connection with such a disease.

More specifically, compounds or pharmaceutical compositions having an antagonistic or inverse agonistic effect on RORγ may be used to reduce levels of IL-17A and/or other gene products, such as interleukins, and cytokines, regulated RORγ. This may for example be in subjects suffering from for example, asthma, acne, chronic obstructive pulmonary disease (COPD), bronchitis, atherosclerosis, *Helicobacter pylori* infection, allergic diseases including allergic rhinitis, allergic conjunctivitis and uveitis, sprue and food allergy, atopic dermatitis, lichen planus, cystic fibrosis, lung allograph rejection, multiple sclerosis, rheumatoid arthritis, juvenile idiopathic arthritis, osteoarthritis, ichthyoses, bullous diseases, hidradenitis suppurativa, ankylosing spondylitis, psoriasis, psoriatic arthritis, steatosis, steatohepatitis, non-alcoholic fatty liver disease (NAFLD), non-alcoholic steatohepatitis (NASH), lupus erythematosus, Hashimoto's disease, pancreatitis, autoimmune diabetes, autoimmune ocular disease, ulcerative colitis, colitis, Crohn's disease, inflammatory bowel disease (IBD), inflammatory bowel syndrome (IBS), Sjogren's syndrome, optic neuritis, type I diabetes, neuromyelitis optica, Myasthenia Gravis, Guillain-Barre syndrome, Graves' disease, scleritis, obesity, obesity-induced insulin resistance and type II diabetes.

Conversely, compounds or pharmaceutical compositions having an agonistic effect on RORγ may be used to increase IL-17A levels. Increasing IL-17A levels may be particularly useful in immune compromised conditions or boosting the immune system response for example during infections and in cancer.

The compounds described herein may be used in the manufacture of a medicament for the treatment and/or prevention of inflammatory, metabolic, oncologic and autoimmune diseases or disorders or a symptom thereof.

Methods of Administration

The compounds or pharmaceutical compositions may be administered to the patient by any suitable means. Non-limiting examples of methods of administration include, among others, (a) administration though oral pathways, which administration includes administration in capsule, tablet, granule, spray, syrup, or other such forms; (b) administration through non-oral pathways such as rectal, vaginal, intraurethral, intraocular, intranasal, or intraauricular, which administration includes administration as an aqueous suspension, an oily preparation or the like or as a drip, spray, suppository, salve, ointment or the like; (c) administration via injection, subcutaneously, intraperitoneally, intravenously, intramuscularly, intradermally, intraorbitally, intracapsularly, intraspinally, intrasternally, or the like, including infusion pump delivery; (d) administration locally such as by injection directly in the renal or cardiac area, e.g., by depot implantation, by intratumoral injection, or by intralymph node injection; (e) administration topically; as well as as well as (f) administration to cells ex vivo followed by insertion of said cells into the patient; as deemed appropriate by those of skill in the art for bringing the compound disclosed herein into contact with living tissue.

Pharmaceutical compositions suitable for administration include compositions where the active ingredients are contained in an amount effective to achieve its intended purpose. The therapeutically effective amount of the compounds disclosed herein required as a dose will depend on the route of administration, the type of animal, including mammal, e.g. human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or adverse side effects disappear. The dosage may range broadly, depending upon the desired effects and the therapeutic indication.

Typically, dosages may be between about 10 microgram/kg and 100 mg/kg body weight, preferably between about 100 microgram/kg and 10 mg/kg body weight. Alternatively dosages may be based and calculated upon the surface area of the patient, as understood by those of skill in the art.

The exact formulation, route of administration and dosage for the pharmaceutical compositions disclosed herein can be chosen by the individual physician in view of the patient's condition. (See e.g., Fingl et al. 1975, in "The Pharmacological Basis of Therapeutics", which is hereby incorporated herein by reference in its entirety, with particular reference to Ch. 1, p. 1). Typically, the dose range of the composition administered to the patient can be from about 0.5 to 1000 mg/kg of the patient's body weight. The dosage may be a single one or a series of two or more given in the course of one or more days, as is needed by the patient. In instances where human dosages for compounds have been established for at least some condition, those same dosages may be used, or dosages that are between about 0.1% and 500%, more preferably between about 25% and 250% of the established human dosage. Where no human dosage is established, as will be the case for newly-discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps the dose frequency will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. The daily dosage regimen for an adult human patient may be, for example, an oral dose of between 0.1 mg and 2000 mg of each active ingredient, preferably between 1 mg and 500 mg, e.g. 5 to 200 mg. An ocular eye drop may range in concentration between 0.005 and 5 percent. In one embodiment, an eye drop may range between 0.01 and 1 percent, or between 0.01 and 0.3 percent in another embodiment. In other embodiments, an intravenous, subcutaneous, or intramuscular dose of each active ingredient of between 0.01 mg and 100 mg, preferably between 0.1 mg and 60 mg, e.g. 1 to 40 mg is used. In cases of administration of a pharmaceutically acceptable salt, dosages may be calculated as the free base. In some embodiments, the composition is administered 1 to 4 times per day. Alternatively the compositions disclosed herein may be administered by continuous intravenous infusion, preferably at a dose of each active ingredient up to 1000 mg per day. As will be understood by those of skill in the art, in certain situations it may be necessary to administer the compounds disclosed herein in amounts that exceed, or even far exceed, the above-stated, preferred dosage range or frequency in order to effectively and aggressively treat particularly aggressive diseases or infections. In some embodiments, the compounds will be administered for a period of continuous therapy, for example for a week or more, or for months or years.

Dosage amount and interval may be adjusted individually to provide plasma or tissue levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen which maintains plasma levels above the MEC for 10-90% of the time, preferably between 30-90% and most preferably between 50-90%.

In cases of local or ex vivo administration or selective uptake, the effective local concentration of the drug may not be related to plasma concentration.

The amount of composition administered may be dependent on the subject being treated, on the subject's weight, the severity of the affliction, the manner of administration and the judgment of the prescribing physician.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition, including but not limited to cancer, cardiovascular disease, and various immune dysfunction. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound disclosed herein formulated in a compatible pharmaceutical carrier may also be prepared, placed in an appropriate container, and labeled for treatment of an indicated condition.

General Remarks

As described above with reference to specific illustrative embodiments, it is not intended to be limited to the specific form set forth herein. Any combination of the above mentioned embodiments should be appreciated as being within the scope of the disclosure. Rather, the disclosure is limited only by the accompanying claims and other embodiments than the specific above are equally possible within the scope of these appended claims.

In the claims, the term "comprises/comprising" does not exclude the presence of other species or steps. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc. do not preclude a plurality. The phrases "at least one" or "one or more" refer to 1 or a number greater than 1, such as to 1, 2, 3, 4, 5, 6, 7, 8, 9, or 10.

Whenever a chemical name or structure has been given it has been generated by conventional means or by means of a suitable software. Names for the compounds were generated with ChemDraw Professional, version 17.1.0.105 (19).

In the present disclosure, in the drawings of the structures, the labels "or1", "or2", "&1", or "&2" at each stereogenic center specify the "stereochemical group" to which the center belongs.

In the case of the "or" groups, the meaning is a structure that represents one stereoisomer that has either the "stereochemical group" as drawn ((R,S), for instance) or the stereoisomer in which the stereogenic centers of the group have the opposite configuration (S,R).

In the case of the "&" groups, & in combination with the number given (e.g. &1) indicate a mixture of the marked asymmetrically substituted atoms. When the numbering pools several asymmetrically substituted atoms together this displays their configuration relative to each other. If they are displayed as (R,S) the opposite configuration (S,R) is also present for the specified pooled group.

Experimental

The following examples are mere examples and should by no mean be interpreted to limit the scope of the disclosure. Rather, the disclosure is limited only by the accompanying claims.

General Chemical Procedures

General

Unless otherwise stated, starting materials were obtained from commercial suppliers, such as (but not limited to); AbBchem, ABCR, Alfa Aesar, Anaspec, Anichem, Apollo Scientific, ASDI-Inter, Asiba Pharmatech, Astatech, ArkPharm, Bachem, Chem-Impex, ChemCollect, Chembridge, Combi-Blocks, Enamine, FCH, Fluka, Fluorochem, Frontier Scientific, HDH Pharma, InFarmatik, InterBioScreen, Fife Chemicals, Manchester organics, Matrix, MercaChem, NetChem, Oakwood Chemical, PepTech, Pharmcore, PrincetonBio, Sigma-Aldrich, TRC, Tyger Scientific and Ukrorgsyn, and were used without further purification. Solvents such as DMF, DMSO and DCM, etc were used directly or dried over molecular sieves.

Equipment

NMR $^1$H NMR spectra were recorded on the following; Bruker Avance 300 spectrometer (at 300 MHz), Bruker Avance III 400 spectrometer (at 400 MHz), Bruker Avance Neo (400 MHz), Bruker Avance III 600 (at 600 MHz), Varian VNMR spectrometer (at 400 MHz) using $CD_3OD$, $CDCl_3$ or $DMSO$-$d_6$ solvents. Chemical shifts are reported in ppm ($\delta$) using residual solvent as an internal standard; $CDCl_3$: 7.26 ppm; $CD_3OD$: 3.31; $DMSO$-$d_6$: 2.50 ppm. Coupling constants (J) are given in Hz.

Analytical U/HPLC

The following equipment was used for analytical U/HPFC:

Waters Acquity system equipped with an Acquity BEH C18 (1.7 µm, 2.1×50 mm) with a linear gradient of a binary solvent system using a flow rate of 0.5 mF/min and DAD at ambient temperature, combined with MS detection SQD I.

Agilent Infinity I/II-TOF6230B/CFND Antek 8060 equipped with Acquity BEH C18 (1.7 µm, 2.1×50 mm) with a linear gradient of a binary solvent system using a flow rate of 0.75 mF/min combined with DAD.

Agilent 1200 series-1260 Infinity equipped with a Waters XBridge C18 (5 µm, 4.6×50 mm) with a linear gradient of a binary solvent system using a flow rate of 1.5 mF/min and UV detection at 214 nm or 254 nm, combined with MS detection (Agilent).

Shimadzu Nexera equipped with a Waters XBridge C18 (5 µm, 4.6×50 mm) with a linear gradient of a binary solvent system using a flow rate of 1.5 mF/min and UV detection at 214 nm or 254 nm, combined with MS detection (Shimadzu).

Waters Acquity system equipped with an Acquity BEH C18 (1.7 µm, 2.1×50 mm) with a linear gradient of a binary solvent system using a flow rate of 0.65 mF/min and DAD at ambient temperature, combined with MS detection Waters spectrometer.

Preparative HPLC

The following equipment was used for Prep-HPFC:

Waters Acquity system equipped with a Supelco DISCOVERY C18 (5 µm, 25 cm×21.2 mm), with a linear gradient of a binary solvent system using a flow rate of 45 mL/min and UV detection at 254 nm, combined with MS detection on a Waters Micromass ZQ Quadrupole MS.

Shimadzu Nexera X2 equipped with a Merck Chromolith SpeedROD RP-18E (5 µm, 10×100 mm) with a linear gradient of a binary solvent system using a flow rate between 4 and 7 mL/min and UV detection at 254 nm, combined with MS detecting on a Shimadzu LCMS-2020.

Waters Masslynx system equipped with a Waters XBridge C18 column (5 µm, 19×150 mm) with a linear gradient of a binary solvent system using a flow rate of 15 mL/min and UV detection at 214 nm or 254 nm, combined with MS detection (Waters).

Gilson GX-281 TRILUTION equipped with a Phenomenex Gemini NX-C18 column (5 µm, 21.2×150 mm) with a linear gradient of a binary solvent system using a flow rate of 15 mL/min and UV detection at 214 nm or 254 nm, combined with MS detection (Waters).

The following linear gradients have been used:

HCO₂H—(H₂O/CH₃CN/HCO₂H (100/0/0.1% to 0/100/0.1%))

NH₄OAC—(H₂O/CH₃CN/NH₄OAC (100/0/0.02% to 0/100/0.02%))

TFA—(H₂O/CH₃CN/TFA (100/0/0.1% to 0/100/0.1%))

NH₄HCO₃—(H₂O/CH₃CN/NH₄HCO₃(100/0/0.1% to 0/100/0.1%))

NH₄OH—(H₂O/CH₃CN/NH₄OH (100/0/0.1% to 0/100/0.1%))

HCO₂ NH₄—(H₂O/50% MeOH+50% CH₃CN/HCO₂H/NH₃ (95/5/0.05%/0.01% to 5/95/0.05%/0.01%))

Flash CC was most often performed on a Isolera® automated systems. Flash CC and Prep TLC were performed employing SiO₂, if not otherwise mentioned. However, C18 columns have also been employed (using a gradient of water-acetonitrile/MeOH (1:1), with or without 0.1% v/v ammonium formate in both phases, from 0% to 100% acetonitrile/MeOH (1:1)).

Analytical Chiral Chromatography

Was performed on a Waters UPC2 system coupled to a DAD detector and a Waters QDa MS detector, equipped with a chiral column with gradient elution using a flow rate of 1 mL/min. The available chiral columns were CHIRAL-PAK (3 μm, 4.6×100 mm) IA, IB, IC and ID and Trefoil AMY1 (2.5 μm, 2.1×150 mm).

The following linear gradients have been used for analytical UPC2:

CO₂/MeOH/DEA (99/1/0.2% to 60/40/0.2%))
CO₂/EtOH/DEA (99/1/0.2% to 60/40/0.2%)
CO₂/IPA/DEA (99/1/0.2% to 60/40/0.2%)

Preparative Chiral Chromatography

Before chiral separation, compounds were purified by the standards methods previously described using the appropriate solvents.

Preparative chiral separations were performed either on a Gilson (306, GX-281 trilution, 156-UV/Vis, Waters 3100 MSD), or a Waters SFC-80, equipped with a chiral column with the solvents specified using flow rates between 10-50 mL/min (only 50 g/min for SCF) and detection at either 214 or 230 nm; The available chiral columns were Reprosil AMS (5 μm, 20 mm×250 mm), Lux C2 (5 μm, 21.2 mm×250 mm), Lux C4 (5 μm, 21.2 mm×250 mm), Chiralpak® column IA, IB, IC, ID, IF or IG (5 μm, 20 mm×250 mm) or Chiralcel® OJ-H or OD-H. Exact column and elution conditions used for each compound are described in the experimental part.

Synthetic Methods

The compounds disclosed herein may be synthesized by one of the following three general methods: General Method H, General Method I and General Method J.

General Method H

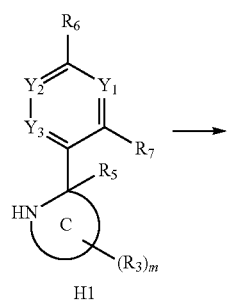

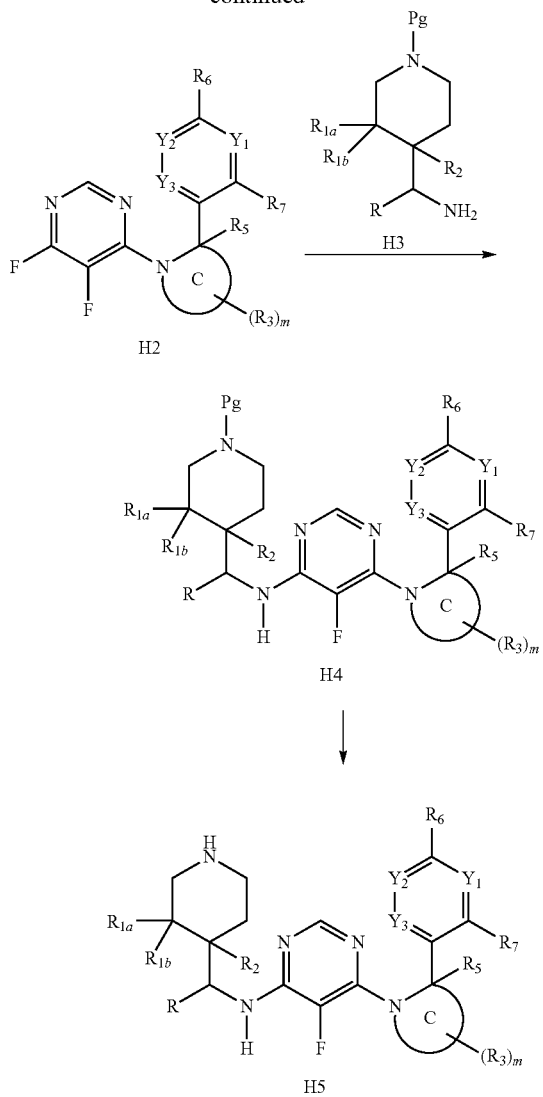

The cyclic amine H1 was reacted with 4,5,6-trifluoropyrimidine (at rt or slightly above, ie 30° C.) together with a suitable base (such as; DIEA, TEA or K₂CO₃). In the cases where H1 was substituted at both the 2- and 6-position the conditions needed to be harsher (ie microwave reactor 100° C. for 10 h). After the reaction was deemed complete, the intermediate H2 was worked up and purified by chromatography (such as Flash CC or prep-HPLC) or used as the crude in the following step. Intermediate H2, a base (such as; DIEA, TEA or Cs₂CO₃) and the primary amine H3 were thereafter dissolved in a solvent (such as DMSO or DMSO-water, water, water-ethanol mixtures, etc) and then the temperature was increased to 70-100° C. on, or until the reaction was considered complete. Work-up and purification then gave intermediate H4, which was subjected to deprotection. The products from the deprotection H5 (either as the free base, TFA salt or the hydrochloride) were then used in the General Methods HA, HB or HC as described below.

H3 amines were commercially available, otherwise the synthesis is described.

Example H5-1

Synthesis of (S)-5-fluoro-N-(piperidin-4-ylmethyl)-6-(3-(5-(trifluoromethyl)pyridin-2-yl)morpholino)pyrimidin-4-amine, H5-1

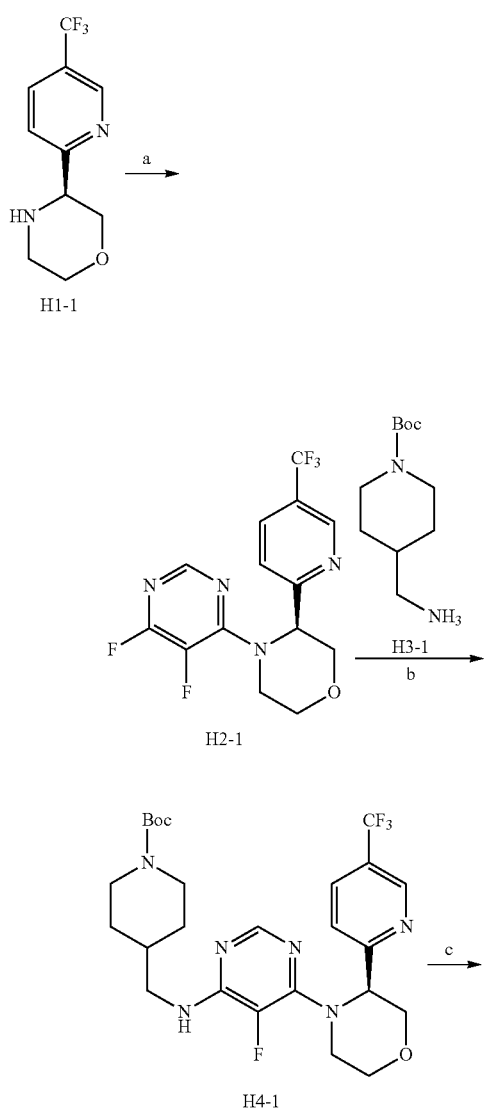

a) DIEA, DMSO b) DIEA, DMSO c) HCl, dioxane (S)-4-(5,6-Difluoropyrimidin-4-yl)-3-(5-(trifluoromethyl)pyridin-2-yl)morpholine, H2-1

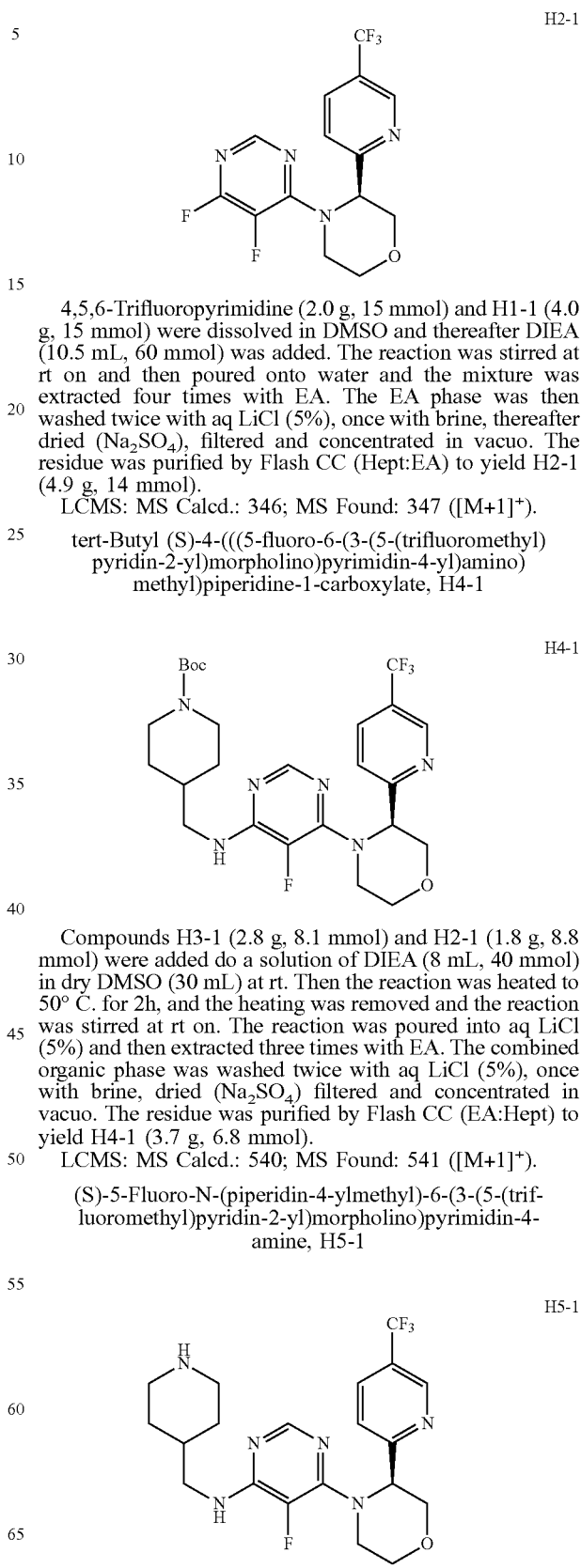

4,5,6-Trifluoropyrimidine (2.0 g, 15 mmol) and H1-1 (4.0 g, 15 mmol) were dissolved in DMSO and thereafter DIEA (10.5 mL, 60 mmol) was added. The reaction was stirred at rt on and then poured onto water and the mixture was extracted four times with EA. The EA phase was then washed twice with aq LiCl (5%), once with brine, thereafter dried ($Na_2SO_4$), filtered and concentrated in vacuo. The residue was purified by Flash CC (Hept:EA) to yield H2-1 (4.9 g, 14 mmol).

LCMS: MS Calcd.: 346; MS Found: 347 ([M+1]$^+$).

tert-Butyl (S)-4-(((5-fluoro-6-(3-(5-(trifluoromethyl)pyridin-2-yl)morpholino)pyrimidin-4-yl)amino)methyl)piperidine-1-carboxylate, H4-1

Compounds H3-1 (2.8 g, 8.1 mmol) and H2-1 (1.8 g, 8.8 mmol) were added do a solution of DIEA (8 mL, 40 mmol) in dry DMSO (30 mL) at rt. Then the reaction was heated to 50° C. for 2h, and the heating was removed and the reaction was stirred at rt on. The reaction was poured into aq LiCl (5%) and then extracted three times with EA. The combined organic phase was washed twice with aq LiCl (5%), once with brine, dried ($Na_2SO_4$) filtered and concentrated in vacuo. The residue was purified by Flash CC (EA:Hept) to yield H4-1 (3.7 g, 6.8 mmol).

LCMS: MS Calcd.: 540; MS Found: 541 ([M+1]$^+$).

(S)-5-Fluoro-N-(piperidin-4-ylmethyl)-6-(3-(5-(trifluoromethyl)pyridin-2-yl)morpholino)pyrimidin-4-amine, H5-1

HCl in dioxane (60 mL, 2M) was added to H4-1 (3.6 g, 6.7 mmol). This caused a sticky mass and aq HCl (15 mL, 2M) was added to dissolve this. The reaction was thereafter stirred at rt for 2 h and concentrated in vacuo. The residue was dissolved in sat NaHCO₃ and EA was added. As no clear phases were distinguishable the mixture was centrifuged for 10 min, thereafter the phases could be separated. The aqueous phase was extracted three times with EA. The combined organic phase was washed with brine, dried (Na₂SO₄) filtered, and concentrated in vacuo yielding crude H5-1 (2.9 g, 6.6 mmol).

LCMS: MS Calcd.: 440; MS Found: 441 ([M+1]⁺).

The intermediate H5 was then transformed into the corresponding acetamide employing one of three different routes;

HA Alkylation of the corresponding alpha-bromo ester together with a suitable base (such as TEA, DIEA or K₂CO₃) followed by hydrolysis to the corresponding acid, and finally EDC-HCl coupling with ammonium chloride and a suitable base.

HB Alkylation of the corresponding alpha-bromo ester together with a suitable base, followed by aminolysis with ammonia.

HC Direct alkylation of 2-bromoacetamide and a suitable base, such TEA, DIEA or K₂CO₃.

General Method HA

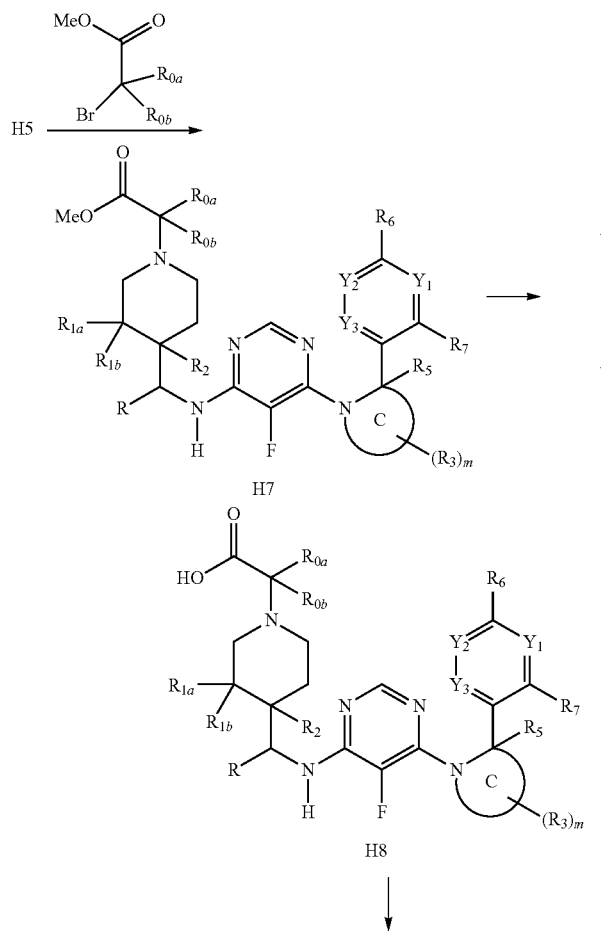

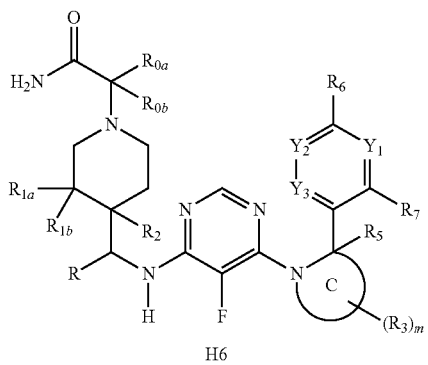

H5 was treated with either; methyl 2-bromoacetate, methyl 2-bromopropanoate or methyl 2-bromo-2-methylpropanoate, and a suitable base, ie TEA, in order to obtain H7. The methyl ester was then hydrolyzed with LiOH in a mixture water/THF/MeOH to obtain the acid (or Li salt thereof) H8. The final product H6 was thereafter obtained in reaction between H8, HOAt, EDC-HCl and NH₄Cl in a suitable solvent.

Example HA

Synthesis of 2-(4-(((5-Fluoro-6-((S)-3-(5-(trifluoromethyl)pyridin-2-yl)morpholino)pyrimidin-4-yl)amino)methyl)piperidin-1-yl)propanamide, H6-1

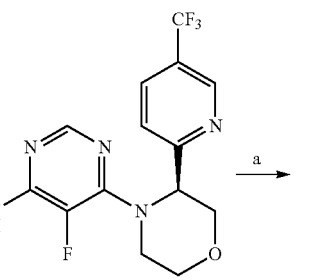

H5-1

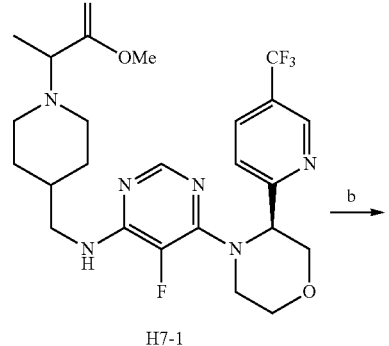

H7-1

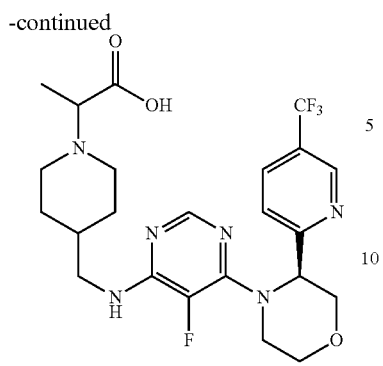

H8-1

↓ c

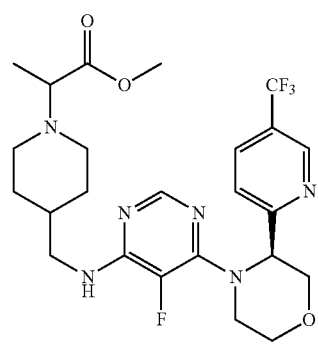

H6-1 a) DIEA, methyl 2-bromopropanoate, DCM. b) LiOH, THF, MeOH. c) DIEA, NH₄Cl, HOAt, EDC•HCl, DMF.

Methyl 2-(4-(((5-fluoro-6-((S)-3-(5-(trifluoromethyl) pyridin-2-yl)morpholino)pyrimidin-4-yl)amino) methyl)piperidin-1-yl)propanoate, H7-1

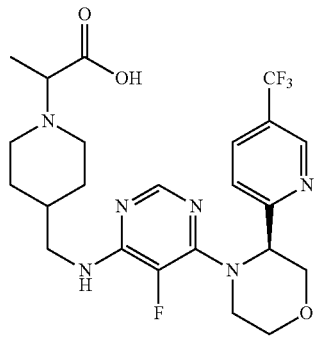

A solution of methyl 2-bromopropanoate (80 uL, 0.72 mmol) in DCM (2 mL) was dropwise added to a stirred solution of DCM (10 mL), DIEA (0.63 mL) and H5-1 (0.26 g, 0.6 mmol) that was cooled on an ice water bath. The ice water bath was removed and the reaction was allowed to stir for 72 h. Then more 2-bromopropanoate (20 uL, 0.18 mmol) was added and the reaction was stirred at 30° C. for 24 h. The reaction was concentrated in vacuo and thereafter sat NaHCO₃ was added and the resulting mixture was extracted three times with EA. The combined organic phase was washed with brine, dried (Na₂SO₄), filtered and concentrated under reduced pressure. The residue was purified by Flash CC (DCM:MeOH) to yield H7-1 (220 mg, 0.42 mmol).

LCMS: MS Calcd.: 526; MS Found: 527 ([M+1]⁺).

2-(4-(((5-Fluoro-6-((S)-3-(5-(trifluoromethyl)pyridin-2-yl)morpholino)pyrimidin-4-yl)amino)methyl) piperidin-1-yl)propanoic acid, H8-1

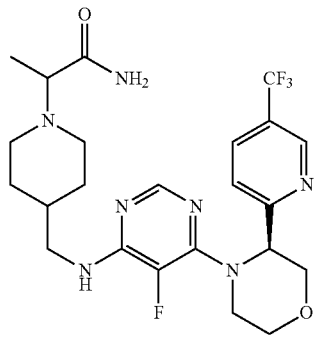

A solution of aq LiOH (0.4 mL, 2M) was added to a solution of H7-1 (220 mg, 0.4 mmol) in THF:MeOH (1:1, 4 mL). The reaction was stirred at rt on. Thereafter concentrated in vacuo to yield the crude title product H8-1 (271 mg) that was used without further purification.

LCMS: MS Calcd.: 512; MS Found: 513 ([M+1]⁺).

2-(4-(((5-Fluoro-6-((S)-3-(5-(trifluoromethyl)pyridin-2-yl)morpholino)pyrimidin-4-yl)amino)methyl) piperidin-1-yl)propanamide, H6-1

H8-1 (271 mg) was added to solution of DMF and DIEA (10 and 0.5 mL respectively). Thereafter the following were added: NH₄Cl (66 mg, 1.23 mmol), HOAt (84 mg, 0.6 mmol), EDC-HCl (117 mg, 0.6 mmol) and the reaction was stirred at rt on. Then more NH₄Cl (66 mg, 1.23 mmol) and EDC-HCl (117 mg, 0.6 mmol) were added and the reaction was again stirred at rt for another 24 h. The reaction was concentrated under vacuum and sat aq NaHCO₃ was added to the residue. The mixture was extracted three times with EA. The combined EA phase was washed twice with aq LiCl (5%), once with brine, dried (Na₂SO₄), filtered concentrated in vacuo to yield the crude product. This was then purified by Flash CC (DCM:MeOH) to yield H6-1 (149 mg, 0.29 mmol).

LCMS: MS Calcd.: 511; MS Found: 512 ([M+1]⁺).

The following compounds were prepared according to the General Method HA:

TABLE HA

| H1 | H3 | H6 |
|---|---|---|
| H1-1 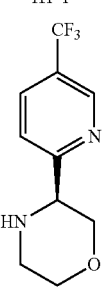 (S)-3-(5-(trifluoromethyl)pyridin-2-yl)morpholine | H3-1 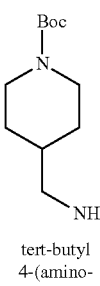 tert-butyl 4-(aminomethyl)piperidine-1-carboxylate | H6-2 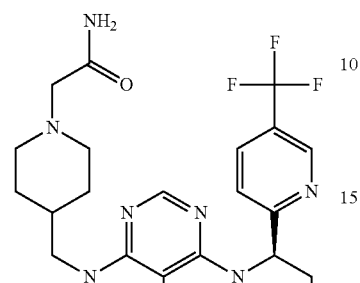 (S)-2-(4-(((5-fluoro-6-(3-(5-(trifluoromethyl)pyridin-2-yl)morpholino)pyrimidin-4-yl)amino)methyl)piperidin-1-yl)acetamide |
| H1-1 | H3-1 | H6-3 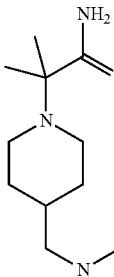 (S)-2-(4-(((5-fluoro-6-(3-(5-(trifluoromethyl)pyridin-2-yl)morpholino)pyrimidin-4-yl)amino)methyl)piperidin-1-yl)-2-methylpropanamide |

General Method HB:

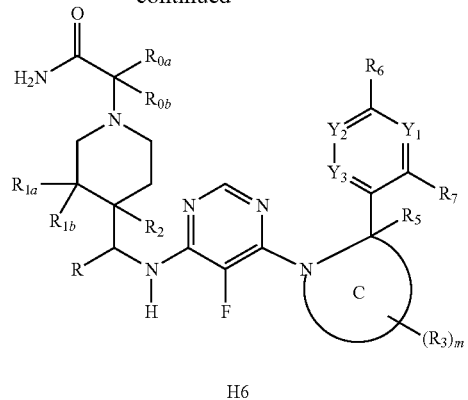

H6

The methyl ester intermediate H7 was subjected to aminolysis in MeOH to obtain H6.

Example HB

Synthesis of (S)-2-(4-fluoro-4-(((5-fluoro-6-(3-(4-(trifluoromethyl)phenyl)morpholino)pyrimidin-4-yl)amino)methyl)piperidin-1-yl)acetamide, H6-4

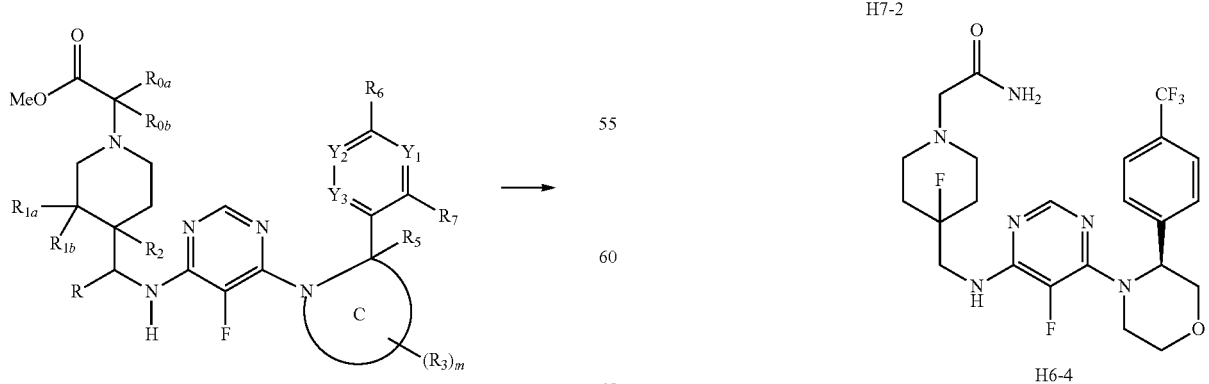

a) DIEA, 2-bromoacetate. b) $NH_3$, MeOH.

79

Methyl (S)-2-(4-fluoro-4-(((5-fluoro-6-(3-(4-(trifluoromethyl)phenyl)morpholino)-pyrimidin-4-yl)amino)methyl)piperidin-1-yl)acetate, H7-2

80

(S)-2-(4-Fluoro-4-(((5-fluoro-6-(3-(4-(trifluoromethyl)phenyl)morpholino)pyrimidin-4-yl)amino)methyl)piperidin-1-yl)acetamide, H6-4

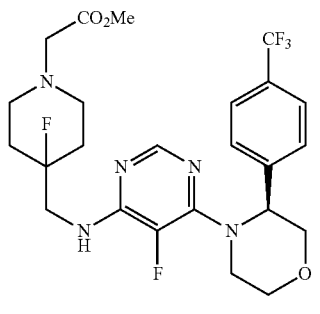

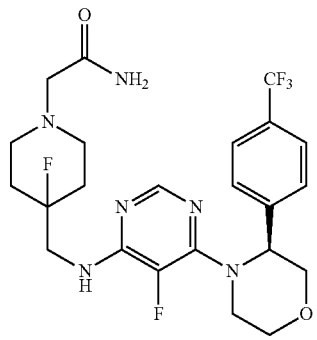

A solution of methyl 2-bomoacetate (67 mg, 0.44 mmol in 1.5 mL DCM) was slowly added to an ice cooled solution of (S)-5-fluoro-N-((4-fluoropiperidin-4-yl)methyl)-6-(3-(4-(trifluoromethyl)phenyl)morpholino)pyrimidin-4-amine H5-2 (167 mg, 0.36 mmol in 7 mL DCM with 380 uL DIEA). The ice bath was removed after the addition, the reaction was allowed to reach rt and was then stirred at rt on. The reaction was concentrated in vacuo, sat aq NaHCO$_3$ was added and the mixture was extracted with three portions of EA. The combined organic phase was washed with brine, dried Na$_2$SO$_4$, filtered and concentrated in vacuo. The residue was purified by Flash CC (DCM:MeOH) to yield H7-2 (180 mg, 0.34 mmol).

LCMS: MS Calcd.: 529; MS Found: 530 ([M+1]$^+$).

H7-2 (180 mg, 0.34 mg) was dissolved in MeOH (3 mL) and cooled on an ice-water bath and then NH$_3$ (g) was bubbled through the solution. The vial was sealed, and the reaction was stirred at rt on. Then the vial was cooled on an ice-bath (−10° C.) and the vial was opened and stirred as it slowly heated to rt. Concentration under reduced pressure gave H6-4 (170 mg, 0.33 mg).

LCMS: MS Calcd.: 514; MS Found: 515 ([M+1]$^+$).

The following compounds were prepared according to the General Method HB:

TABLE HB

| H1 | H3 | H6 |
|---|---|---|
| H1-2 | H3-1 | H6-5 |
| (S)-3-(4-(trifluoromethyl)phenyl)morpholine | | (S)-2-(4-(((5-fluoro-6-(3-(4-(trifluoromethyl)phenyl)morpholino)pyrimidin-4-yl)amino)methyl)piperidin-1-yl)acetamide |

TABLE HB-continued

| H1 | H3 | H6 |
|---|---|---|
| H1-3<br>(S)-3-(4-(trifluoromethoxy)phenyl)morpholine | H3-2<br>tert-butyl 4-(aminomethyl)-4-fluoropiperidine-1-carboxylate | H6-6<br>(S)-2-(4-fluoro-4-(((5-fluoro-6-(3-(4-(trifluoromethoxy)phenyl)morpholino)pyrimidin-4-yl)amino)methyl)piperidin-1-yl)acetamide |
| H1-2 | H3-3<br>rac-tert-butyl (3R,4R)-4-(aminomethyl)-3-hydroxypiperidine-1-carboxylate | H6-7<br>2-((3RS,4RS)-4-(((5-fluoro-6-((S)-3-(4-(trifluoromethyl)phenyl)morpholino)pyrimidin-4-yl)amino)methyl)-3-hydroxypiperidin-1-yl)acetamide |

TABLE HB-continued

| H1 | H3 | H6 |
|---|---|---|
| H1-2 | H3-3 | H6-7-1 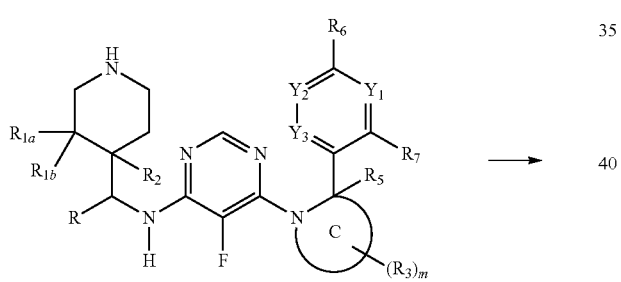 2-((3R*,4R*)-4-(((5-fluoro-6-((S)-3-(4-(trifluoromethyl)phenyl)morpholino)pyrimidin-4-yl)amino)methyl)-3-hydroxypiperidin-1-yl)acetamide 1$^{st}$ eluting isomer |
| H1-2 | H3-3 | H6-7-2 2-((3R*,4R*)-4-(((5-fluoro-6-((S)-3-(4-(trifluoromethyl)phenyl)morpholino)pyrimidin-4-yl)amino)methyl)-3-hydroxypiperidin-1-yl)acetamide 2$^{nd}$ eluting isomer |

General Method HC:

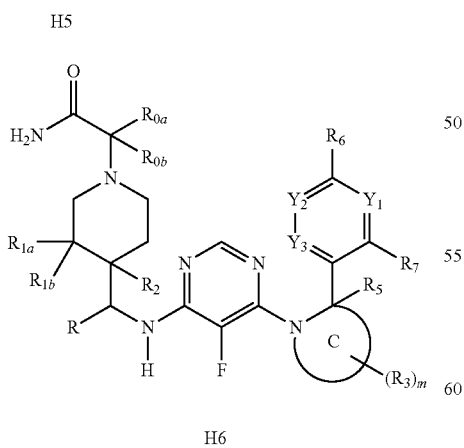

The intermediate H5 was treated with 2-bromoacetamide and a suitable base, such as DIEA, $Na_2CO_3$ or $K_2CO_3$ to give final compounds H6.

Example HC

Synthesis of (S)-2-(4-fluoro-4-(((5-fluoro-6-(3-(5-(trifluoromethyl)pyridin-2-yl)morpholino)pyrimidin-4-yl)amino)methyl)piperidin-1-yl)acetamide, H6-8

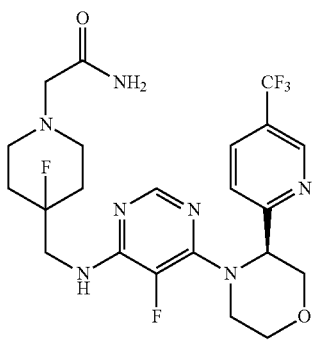

$K_2CO_3$ (65 mg, 0.5 mmol) followed by 2-bromoacetamide (30 mg, 0.22 mmol) were added to a solution of ((S)-4-(5,6-difluoropyrimidin-4-yl)-3-(5-(trifluoromethyl)pyridin-2-yl)morpholine H5-3 (30 mg, 0.07 mmol) in dry THF. The reaction was stirred at rt for 4 h and then at 30° C. on. The reaction was filtered, and the filtrate was concentrated in vacuo. The residue was purified by Prep-HPLC to yield H6-8 (17.4 mg, 0.034 mmol).

The following compounds were prepared according to the General Method HC

TABLE HC

| H1 | H3 | H6 |
|---|---|---|
| H1-2 | H3-4 tert-butyl 4-(aminomethyl)-3,3-difluoro-piperidine-1-carboxylate | H6-9-1 2-((R*)-3,3-difluoro-4-(((5-fluoro-6-((S)-3-(4-(trifluoromethyl)phenyl)morpholino)pyrimidin-4-yl)amino)methyl)piperidin-1-yl)acetamide 1st eluting isomer |
| H1-2 | H3-4 | H6-9-2 2-((R*)-3,3-difluoro-4-(((5-fluoro-6-((S)-3-(4-(trifluoromethyl)phenyl)morpholino)pyrimidin-4-yl)amino)methyl)piperidin-1-yl)acetamide 2nd eluting isomer |
| H1-2 | H3-5 rac-tert-butyl (3R,4R)-4-(aminomethyl)-3-fluoropiperidine-1-carboxylate | H6-10-1 2-((3R*,4R*)-3-fluoro-4-(((5-fluoro-6-((S)-3-(4-(trifluoromethyl)phenyl)morpholino)pyrimidin-4-yl)amino)methyl)piperidin-1-yl)acetamide 1st eluting isomer |

TABLE HC-continued

| H1 | H3 | H6 |
|---|---|---|
| H1-2 | H3-5 | H6-10-2<br>2-((3R*,4R*)-3-fluoro-4-(((5-fluoro-6-((S)-3-(4-(trifluoromethyl)phenyl)morpholino)pyrimidin-4-yl)amino)methyl)piperidin-1-yl)acetamide<br>2<sup>nd</sup> eluting isomer |
| H1-1<br>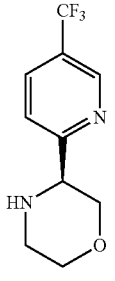<br>(S)-3-(5-(trifluoromethyl)pyridin-2-yl)morpholine | H3-4 | H6-11-1<br>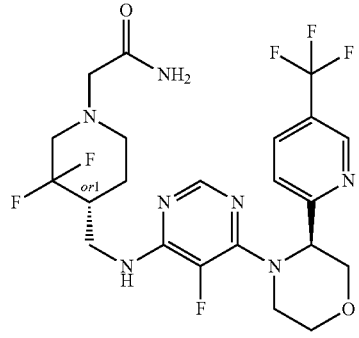<br>2-((R*)-3,3-difluoro-4-(((5-fluoro-6-((S)-3-(5-(trifluoromethyl)pyridin-2-yl)morpholino)pyrimidin-4-yl)amino)methyl)piperidin-1-yl)acetamide<br>1<sup>st</sup> eluting isomer |
| H1-1 | H3-4 | H6-11-2<br>2-((R*)-3,3-difluoro-4-(((5-fluoro-6-((S)-3-(5-(trifluoromethyl)pyridin-2-yl)morpholino)pyrimidin-4-yl)amino)methyl)piperidin-1-yl)acetamide<br>2<sup>nd</sup> eluting isomer |
| H1-1 | H3-6<br>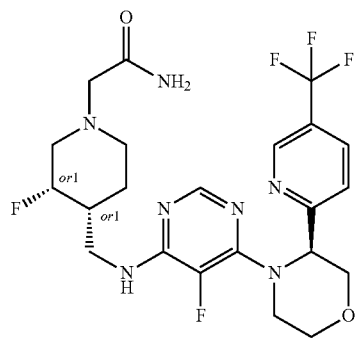<br>rac-2-((3R,4S)-4-(aminomethyl)-3-fluoropiperidin-1-yl)acetamide | H6-12-1<br>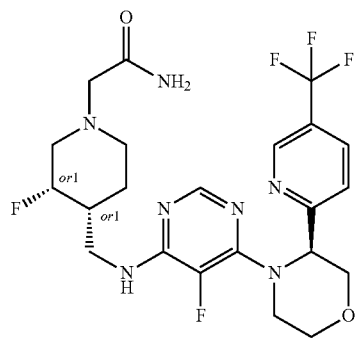<br>2-((3R*,4S*)-3-fluoro-4-(((5-fluoro-6-((S)-3-(5-(trifluoromethyl)pyridin-2-yl)morpholino)pyrimidin-4-yl)amino)methyl)piperidin-1-yl)acetamide<br>1<sup>st</sup> eluting isomer |

TABLE HC-continued

| H1 | H3 | H6 |
|---|---|---|
| H1-1 | H3-6 | H6-12-2<br>2-((3R*,4S*)-3-fluoro-4-(((5-fluoro-6-((S)-3-(5-(trifluoromethyl)pyridin-2-yl)morpholino)pyrimidin-4-yl)amino)methyl)piperidin-1-yl)acetamide<br>2$^{nd}$ eluting isomer |
| H1-1 | H3-5 | H6-13-1<br>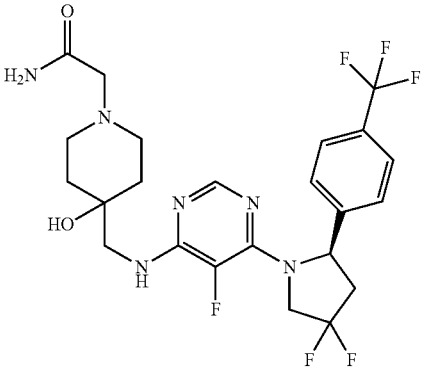<br>2-((3R*,4R*)-3-fluoro-4-(((5-fluoro-6-((S)-3-(5-(trifluoromethyl)pyridin-2-yl)morpholino)pyrimidin-4-yl)amino)methyl)piperidin-1-yl)acetamide<br>1$^{st}$ eluting isomer |
| H1-1 | H3-5 | H6-13-2<br>2-((3R*,4R*)-3-fluoro-4-(((5-fluoro-6-((S)-3-(5-(trifluoromethyl)pyridin-2-yl)morpholino)pyrimidin-4-yl)amino)methyl)piperidin-1-yl)acetamide<br>2$^{nd}$ eluting isomer |
| H1-4<br>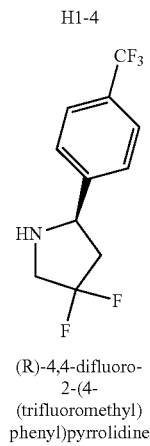<br>(R)-4,4-difluoro-2-(4-(trifluoromethyl)phenyl)pyrrolidine | H3-7 | H6-14<br>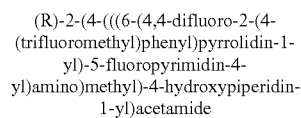<br>(R)-2-(4-(((6-(4,4-difluoro-2-(4-(trifluoromethyl)phenyl)pyrrolidin-1-yl)-5-fluoropyrimidin-4-yl)amino)methyl)-4-hydroxypiperidin-1-yl)acetamide |

TABLE HC-continued

| H1 | H3 | H6 |
|---|---|---|
| H1-4 | H3-4 | H6-15-1 |

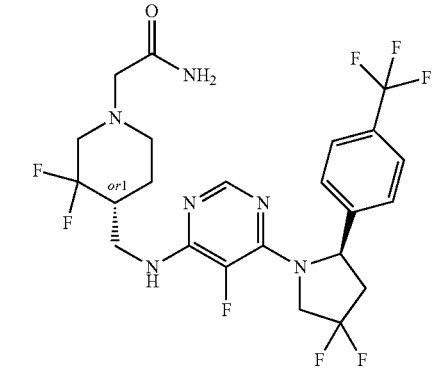

2-((R*)-4-(((6-((R)-4,4-difluoro-2-(4-(trifluoromethyl)phenyl)pyrrolidin-1-yl)-5-fluoropyrimidin-4-yl)amino)methyl)-3,3-difluoropiperidin-1-yl)acetamide
1st eluting isomer

| H1-4 | H3-4 | H6-15-2 |
|---|---|---|

2-((R*)-4-(((6-((R)-4,4-difluoro-2-(4-(trifluoromethyl)phenyl)pyrrolidin-1-yl)-5-fluoropyrimidin-4-yl)amino)methyl)-3,3-difluoropiperidin-1-yl)acetamide
2nd eluting isomer

| H1-4 | H3-5 | H6-16-1 |
|---|---|---|

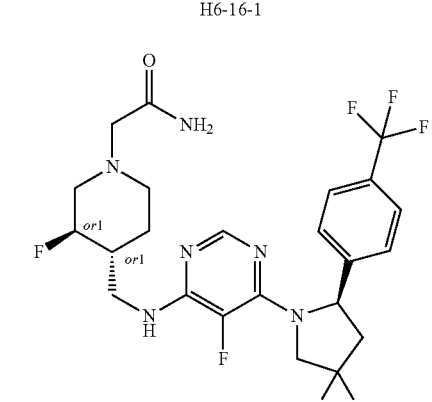

2-((3R*,4R*)-4-(((6-((R)-4,4-difluoro-2-(4-(trifluoromethyl)phenyl)pyrrolidin-1-yl)-5-fluoropyrimidin-4-yl)amino)methyl)-3-fluoropiperidin-1-yl)acetamide
1st eluting isomer

| H1-4 | H3-5 | H6-16-2 |
|---|---|---|

2-((3R*,4R*)-4-(((6-((R)-4,4-difluoro-2-(4-(trifluoromethyl)phenyl)pyrrolidin-1-yl)-5-fluoropyrimidin-4-yl)amino)methyl)-3-fluoropiperidin-1-yl)acetamide
2nd eluting isomer TABLE HC-continued

| H1 | H3 | H6 |
|---|---|---|
| H1-4 | H3-3 | H6-17 |

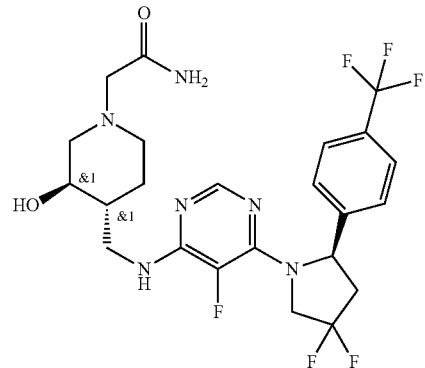

2-((3RS,4RS)-4-((((6-((R)-4,4-difluoro-2-
(4-(trifluoromethyl)phenyl)pyrrolidin-1-
yl)-5-fluoropyrimidin-4-
yl)amino)methyl)-3-hydroxypiperidin-
1-yl)acetamide

| H1 | H3 | H6 |
|---|---|---|
| H1-4 | H3-3 | H6-17-1 |

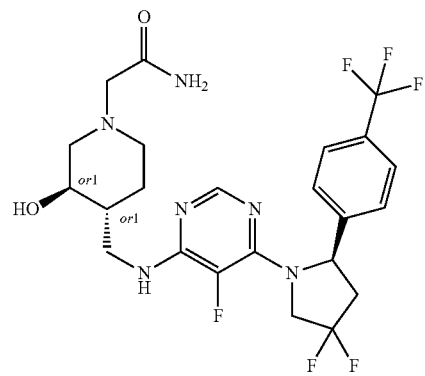

2-((3R*,4R*)-4-((((6-((R)-4,4-difluoro-2-
(4-(trifluoromethyl)phenyl)pyrrolidin-1-
yl)-5-fluoropyrimidin-4-
yl)amino)methyl)-3-hydroxypiperidin-
1-yl)acetamide
1st eluting isomer

| H1 | H3 | H6 |
|---|---|---|
| H1-4 | H3-3 | H6-17-2 |

2-((3R*,4R*)-4-((((6-((R)-4,4-difluoro-2-
(4-(trifluoromethyl)phenyl)pyrrolidin-1-
yl)-5-fluoropyrimidin-4-
yl)amino)methyl)-3-hydroxypiperidin-
1-yl)acetamide
2nd eluting isomer

TABLE HC-continued

| H1 | H3 | H6 |
|---|---|---|
| H1-5 | H3-5 | H6-18-1 |

(R)-2-(4,4-difluoropyrrolidin-2-yl)-5-(trifluoromethyl)pyridine 2-((3R*,4R*)-4-(((6-((R)-4,4-difluoro-2-(5-(trifluoromethyl)pyridin-2-yl)pyrrolidin-1-yl)-5-fluoropyrimidin-4-yl)amino)methyl)-3-fluoropiperidin-1-yl)acetamide
1st eluting isomer

| H1 | H3 | H6 |
|---|---|---|
| H1-5 | H3-5 | H6-18-2 |

2-((3R*,4R*)-4-(((6-((R)-4,4-difluoro-2-(5-(trifluoromethyl)pyridin-2-yl)pyrrolidin-1-yl)-5-fluoropyrimidin-4-yl)amino)methyl)-3-fluoropiperidin-1-yl)acetamide
2nd eluting isomer

| H1 | H3 | H6 |
|---|---|---|
| H1-5 | H3-4 | H6-19-1 |

2-((R*)-4-(((6-((R)-4,4-difluoro-2-(5-(trifluoromethyl)pyridin-2-yl)pyrrolidin-1-yl)-5-fluoropyrimidin-4-yl)amino)methyl)-3,3-difluoropiperidin-1-yl)acetamide
1st eluting isomer

| H1 | H3 | H6 |
|---|---|---|
| H1-5 | H3-4 | H6-19-2 |

2-((R*)-4-(((6-((R)-4,4-difluoro-2-(5-(trifluoromethyl)pyridin-2-yl)pyrrolidin-1-yl)-5-fluoropyrimidin-4-yl)amino)methyl)-3,3-difluoropiperidin-1-yl)acetamide
2nd eluting isomer

TABLE HC-continued

| H1 | H3 | H6 |
|---|---|---|
| H1-5 | H3-3 | H6-20 |

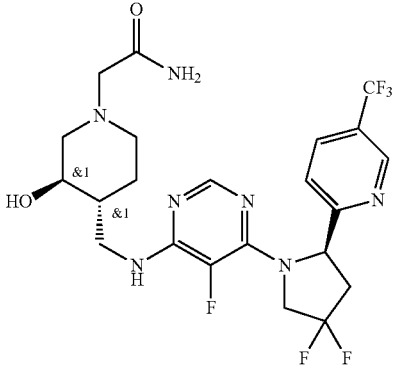

2-((3RS,4RS)-4-(((6-((R)-4,4-difluoro-2-(5-(trifluoromethyl)pyridin-2-yl)pyrrolidin-1-yl)-5-fluoropyrimidin-4-yl)amino)methyl)-3-hydroxypiperidin-1-yl)acetamide

| H1 | H3 | H6 |
|---|---|---|
| H1-6-1 | H3-3 | H6-21-1 |

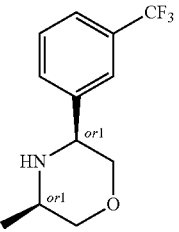 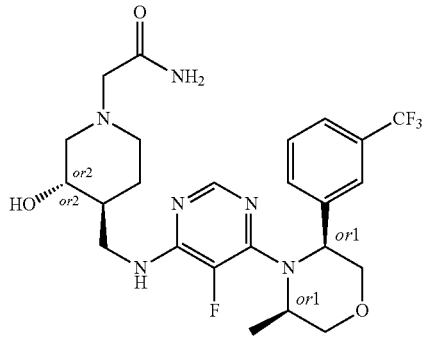

rel-(3R,5S)-3-methyl-5-(3-(trifluoromethyl)phenyl)morpholine
1ˢᵗ eluting isomer rel-2-((3R,4R)-4-(((5-fluoro-6-((3S,5R)-3-methyl-5-(3-(trifluoromethyl)phenyl)morpholino)pyrimidin-4-yl)amino)methyl)-3-hydroxypiperidin-1-yl)acetamide
OR
rel-2-((3R,4R)-4-(((5-fluoro-6-((3R,5S)-3-methyl-5-(3-(trifluoromethyl)phenyl)morpholino)pyrimidin-4-yl)amino)methyl)-3-hydroxypiperidin-1-yl)acetamide
1ˢᵗ eluting isomer

| H1 | H3 | H6 |
|---|---|---|
| H1-6-1 | H3-3 | H6-21-2 | rel-2-((3R,4R)-4-(((5-fluoro-6-((3S,5R)-3-methyl-5-(3-(trifluoromethyl)phenyl)morpholino)pyrimidin-4-yl)amino)methyl)-3-hydroxypiperidin-1-yl)acetamide
OR
rel-2-((3R,4R)-4-(((5-fluoro-6-((3R,4S)-3-methyl-5-(3-(trifluoromethyl)phenyl)morpholino)pyrimidin-4-yl)amino)methyl)-3-hydroxypiperidin-1-yl)acetamide
2ⁿᵈ eluting isomer TABLE HC-continued

| H1 | H3 | H6 |
|---|---|---|
| H1-6-2<br><br>rel-(3R,5S)-3-methyl-5-(3-(trifluoromethyl)phenyl)morpholine<br>2nd eluting isomer | H3-3 | H6-21-3<br>rel-2-((3R,4R)-4-(((5-fluoro-6-((3S,5R)-3-methyl-5-(3-(trifluoromethyl)phenyl)morpholino)pyrimidiin-4-yl)amino)methyl)-3-hydroxypiperidin-1-yl)acetamide<br>OR<br>rel-2-((3R,4R)-4-(((5-fluoro-6-((3R,4S)-3-methyl-5-(3-(trifluoromethyl)phenyl)morpholino)pyrimidin-4-yl)amino)methyl)-3-hydroxypiperidin-1-yl)acetamide<br>1st eluting isomer |
| H1-6-2 | H3-3 | H6-21-4<br>rel-2-((3R,4R)-4-(((5-fluoro-6-((3S,5R)-3-methyl-5-(3-(trifluoromethyl)phenyl)morpholino)pyrimidin-4-yl)amino)methyl)-3-hydroxypiperidin-1-yl)acetamide<br>OR<br>rel-2-((3R,4R)-4-(((5-fluoro-6-((3R,5S)-3-methyl-5-(3-(trifluoromethyl)phenyl)morpholino)pyrimidin-4-yl)amino)methyl)-3-hydroxypiperidin-1-yl)acetamide<br>2nd eluting isomer |
| H1-7-1<br><br>rel-(3R,5S)-3-methyl-5-(4-(trifluoromethyl)phenyl)morpholine<br>1st eluting isomer | H3-3 | H6-22-1<br><br>rel-2-((3R,4R)-4-(((5-fluoro-6-((3S,5R)-3-methyl-5-(4-(trifluoromethyl)phenyl)morpholino)pyrimidin-4-yl)amino)methyl)-3-hydroxypiperidin-1-yl)acetamide<br>OR<br>rel-2-((3R,4R)-4-(((5-fluoro-6-((3R,5S)-3-methyl-5-(4-(trifluoromethyl)phenyl)morpholino)pyrimidin-4-yl)amino)methyl)-3-hydroxypiperidin-1-yl)acetamide<br>1st eluting isomer |

TABLE HC-continued

| H1 | H3 | H6 |
|---|---|---|
| H1-7-1 | H3-3 | H6-22-2<br>rel-2-((3R,4R)-4-(((5-fluoro-6-((3S,5R)-3-methyl-5-(4-(trifluoromethyl)phenyl)morpholino)pyrimidin-4-yl)amino)methyl)-3-hydroxypiperidin-1-yl)acetamide<br>OR<br>rel-2-((3R,4R)-4-(((5-fluoro-6-((3R,4S)-3-methyl-5-(4-(trifluoromethyl)phenyl)morpholino)pyrimidin-4-yl)amino)methyl)-3-hydroxypiperidin-1-yl)acetamide<br>2$^{nd}$ eluting isomer |
| H1-7-2<br>rel-(3R,5S)-3-methyl-5-(4-(trifluoromethyl)phenyl)morpholine<br>2$^{nd}$ eluting isomer | H3-3 | H6-22-3<br>rel-2-((3R,4R)-4-(((5-fluoro-6-((3S,5R)-3-methyl-5-(4-(trifluoromethyl)phenyl)morpholino)pyrimidin-4-yl)amino)methyl)-3-hydroxypiperidin-1-yl)acetamide<br>OR<br>rel-2-((3R,4R)-4-(((5-fluoro-6-((3R,5S)-3-methyl-5-(4-(trifluoromethyl)phenyl)morpholino)pyrimidin-4-yl)amino)methyl)-3-hydroxypiperidin-1-yl)acetamide<br>1$^{st}$ eluting isomer |
| H1-7-2 | H3-3 | H6-22-4<br>rel-2-((3R,4R)-4-(((5-fluoro-6-((3S,5R)-3-methyl-5-(4-(trifluoromethyl)phenyl)morpholino)pyrimidin-4-yl)amino)methyl)-3-hydroxypiperidin-1-yl)acetamide<br>OR<br>rel-2-((3R,4R)-4-(((5-fluoro-6-((3R,4S)-3-methyl-5-(4-(trifluoromethyl)phenyl)morpholino)pyrimidin-4-yl)amino)methyl)-3-hydroxypiperidin-1-yl)acetamide<br>2$^{nd}$ eluting isomer |

General Method I

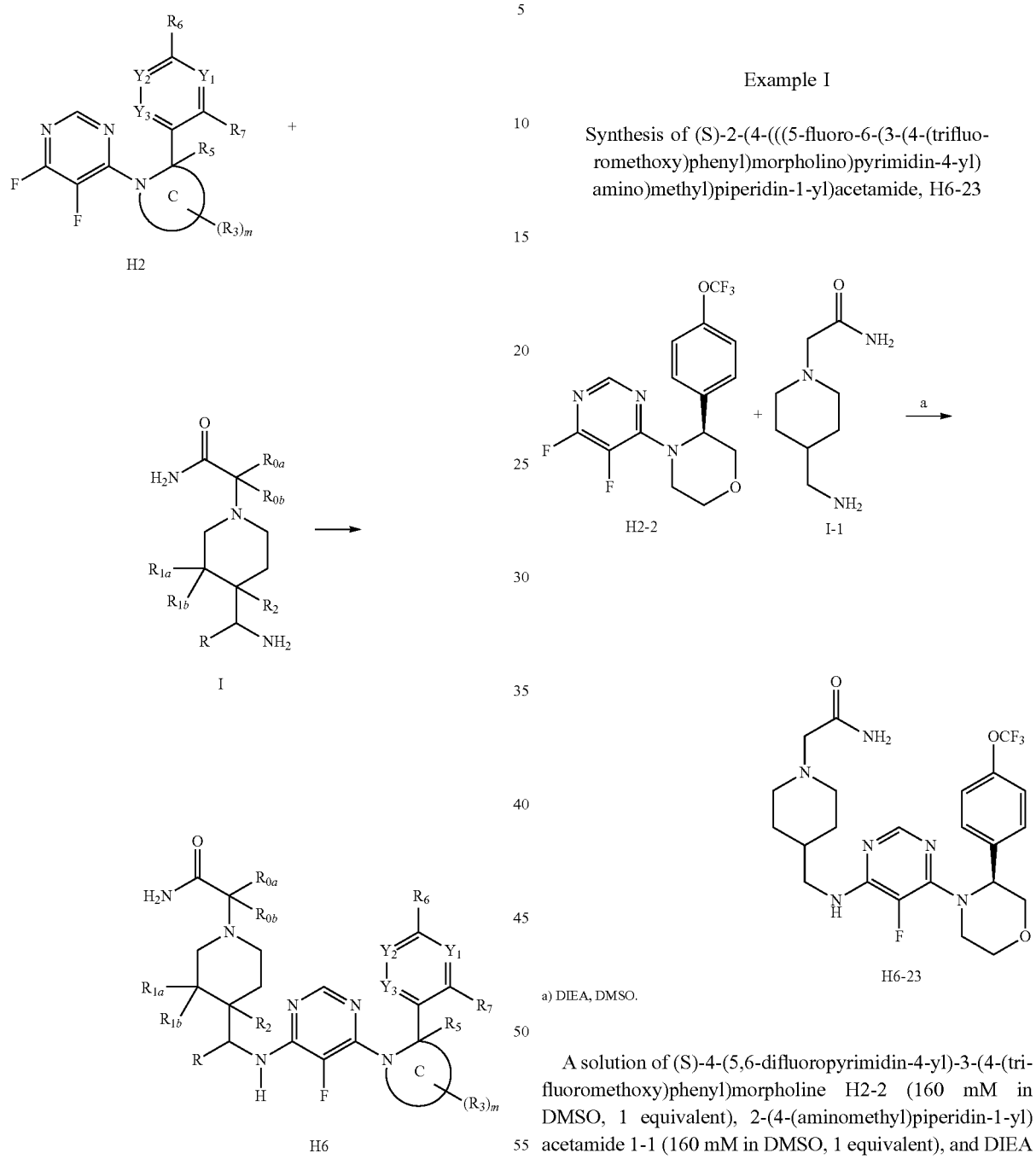

The compounds have also been made by performing the addition of 2-(4-(aminomethyl)piperidin-1-yl)acetamide to the intermediates H2 (synthesized as outlined in General Method H). The NAS reaction was performed using the same conditions (a suitable base, such as DIEA or TEA) in DMSO at 80-100° C.). The reactions mixtures were thereafter concentrated and purified directly using chromatographic methods.

Example I

Synthesis of (S)-2-(4-(((5-fluoro-6-(3-(4-(trifluoromethoxy)phenyl)morpholino)pyrimidin-4-yl)amino)methyl)piperidin-1-yl)acetamide, H6-23 a) DIEA, DMSO.

A solution of (S)-4-(5,6-difluoropyrimidin-4-yl)-3-(4-(trifluoromethoxy)phenyl)morpholine H2-2 (160 mM in DMSO, 1 equivalent), 2-(4-(aminomethyl)piperidin-1-yl)acetamide I-1 (160 mM in DMSO, 1 equivalent), and DIEA (neat, 6 equivalents). The reaction was shaken at 80° C. on and then at 100° C. for 4 h. The reaction was thereafter cooled and concentrated in vacuo. Subsequent analysis and purification of the resulting residue by HPLC gave the pure title compound H6-23 (62%).

LCMS: MS Calcd.: 512; MS Found: 513 ([M+1]$^+$).

The following compounds were made according to General Method I:

TABLE I

| H1 | H6 |
|---|---|
| H1-16<br>4,4-difluoro-2-(4-(trifluoromethyl)phenyl)pyrrolidine | H6-24<br>2-(4-(((6-(4,4-difluoro-2-(4-(trifluoromethyl)phenyl)pyrrolidin-1-yl)-5-fluoropyrimidin-4-yl)amino)methyl)piperidin-1-yl)acetamide |
| H1-8<br>2-(4-(trifluoromethyl)phenyl)pyrrolidine | H6-25<br>2-(4-(((5-fluoro-6-(2-(4-(trifluoromethyl)phenyl)pyrrolidin-1-yl)pyrimidin-4-yl)amino)methyl)piperidin-1-yl)acetamide |
| H1-9<br>(R)-2-(4-(trifluoromethyl)phenyl)pyrrolidine | H6-25-1<br>(R)-2-(4-(((5-fluoro-6-(2-(4-(trifluoromethyl)phenyl)pyrrolidin-1-yl)pyrimidin-4-yl)amino)methyl)piperidin-1-yl)acetamide |

TABLE I-continued

| H1 | H6 |
|---|---|
| H1-10<br>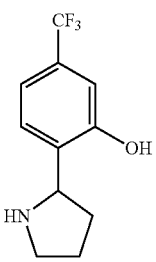<br>2-(pyrrolidin-2-yl)-5-(trifluoromethyl)phenol | H6-26<br>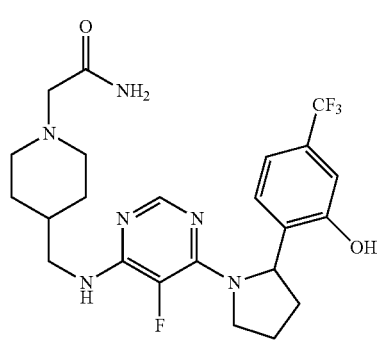<br>2-(4-(((5-fluoro-6-(2-(2-hydroxy-4-(trifluoromethyl)phenyl)pyrrolidin-1-yl)pyrimidin-4-yl)amino)methyl)piperidin-1-yl)acetamide |
| H1-11<br>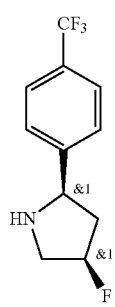<br>rac-(2R,4R)-4-fluoro-2-(4-(trifluoromethyl)phenyl)pyrrolidine | H6-27<br>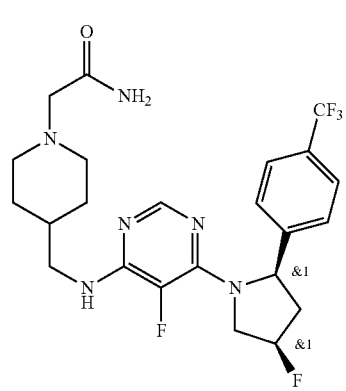<br>rac-2-(4-(((5-fluoro-6-((2R,4R)-4-fluoro-2-(4-(trifluoromethyl)phenyl)pyrrolidin-1-yl)pyrimidin-4-yl)amino)methyl)piperidin-1-yl)acetamide |
| H1-12<br>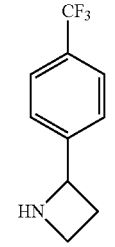<br>2-(4-(trifluoromethyl)phenyl)azetidine | H6-28<br>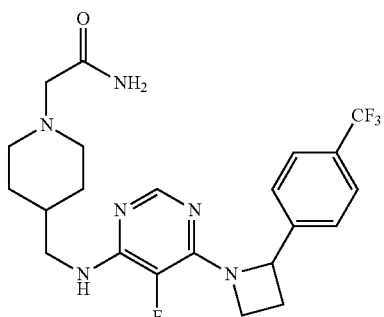<br>2-(4-(((5-fluoro-6-(2-(4-(trifluoromethyl)phenyl)azetidin-1-yl)pyrimidin-4-yl)amino)methyl)piperidin-1-yl)acetamide |

General Method J

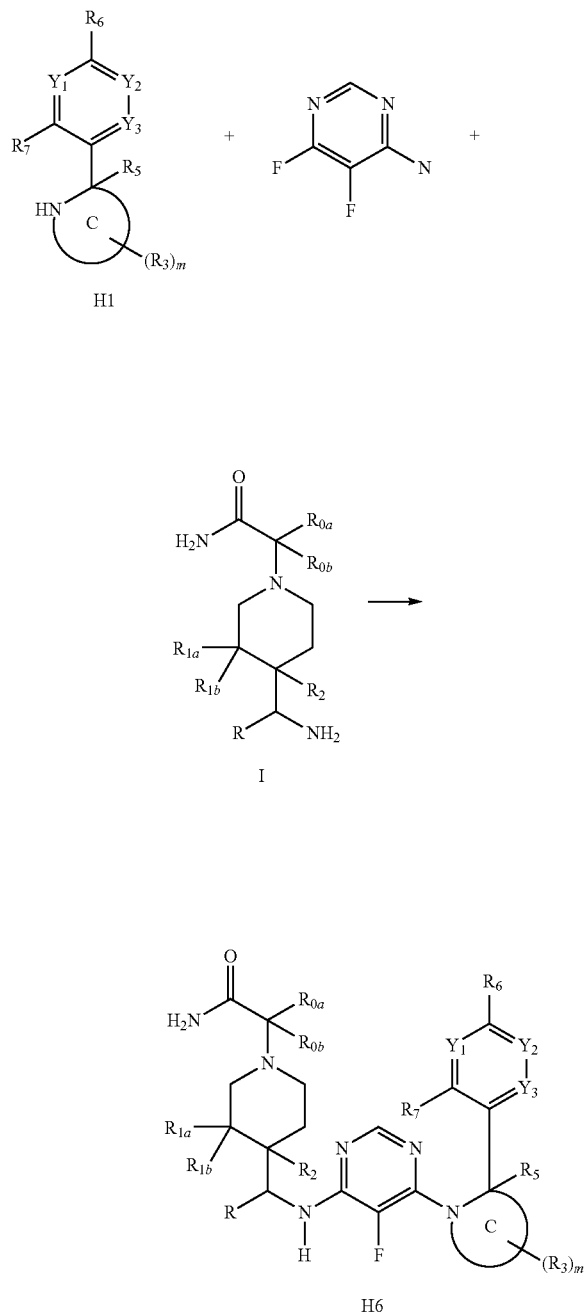

The compounds have also been synthesized using a one-pot, two step synthesis procedure. The secondary amine H1 and trifluoropyrimidine were added to a solution of DIEA in DMSO and stirred at rt for 3 h to produce H2 in situ. Thereafter, I was added together with additional DIEA and the reaction was heated to 80° C. overnight. The reaction mixture was cooled to rt and concentrated. The remaining residue was thereafter purified by Prep HPLC to yield H6.

Example J

Synthesis of rac-2-((3R,4R)-4-(((6-(2-(4-chlorophenyl)pyrrolidin-1-yl)-5-fluoropyrimidin-4-yl)amino)methyl)-3-hydroxypiperidin-1-yl)acetamide, H6-29

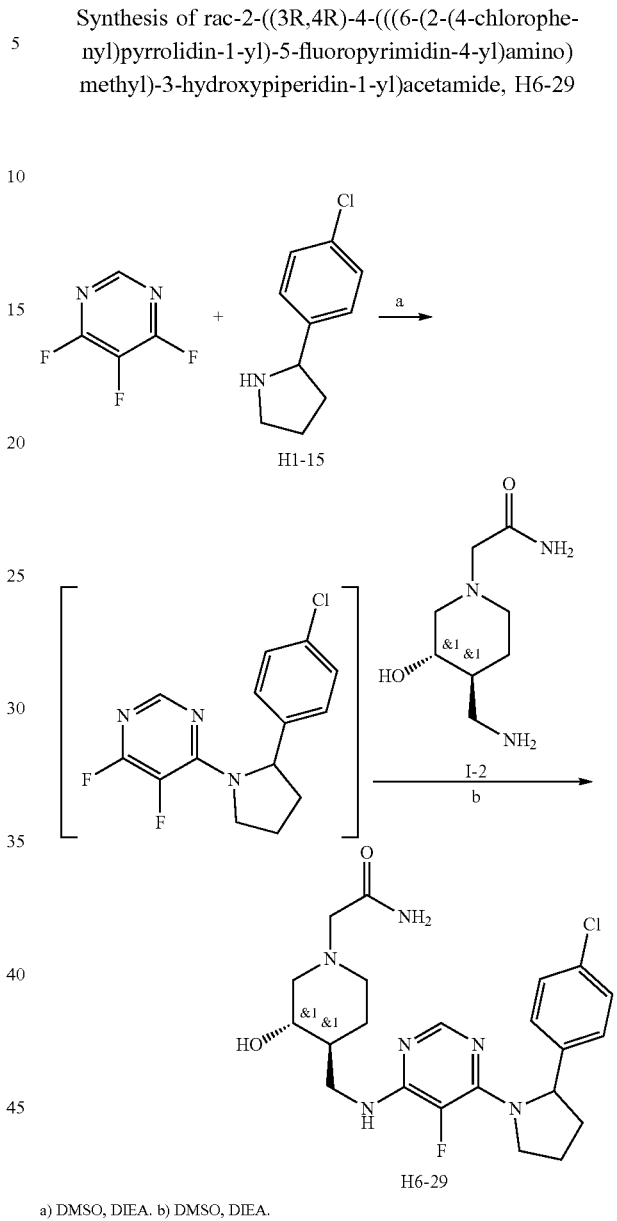

a) DMSO, DIEA. b) DMSO, DIEA.

A solution of 4,5,6-trifluoropyrimidine (160 mM in DMSO, 1 equivalent) and DIEA (neat, 6 equivalents) were added to a solution of 2-(4-chlorophenyl)pyrrolidine, H1-15 (160 mM in DMSO, 1 equivalent). The reaction was shaken at ambient temperature for 3 h. Thereafter, a DMSO solution of rac-2-((3R,4R)-4-(aminomethyl)-3-hydroxypiperidin-1-yl)acetamide hydrochloride 1-2 (160 mM, 1 equivalent) and DIEA (neat, 4 equivalents) were added and the reaction was shaken at 80° C. on. The reaction was then allowed to cool and then concentrated under reduced pressure. Subsequent analysis and purification by HPLC gave H6-29 (48%).

The following compounds were made according to General Method J:

TABLE J

| H1 | H6 |
|---|---|
| H1-13-2 | H6-30 |
| rel-(1R,5S)-1-(6-(trifluoromethyl)pyridin-3-yl)-2-azabicyclo[3.1.0]hexane | 2-((3RS,4RS)-4-(((5-fluoro-6-((1S*,5R*)-1-(6-(trifluoromethyl)pyridin-3-yl)-2-azabicyclo[3.1.0]hexan-2-yl)pyrimidin-4-yl)amino)methyl)-3-hydroxypiperidin-1-yl)acetamide |
| H1-14 | H6-31 |
| 2-(6-(trifluoromethyl)pyridin-3-yl)-3-azabicyclo[3.1.0]hexane | rac-2-((3R,4R)-4-(((5-fluoro-6-(2-(6-(trifluoromethyl)pyridin-3-yl)-3-azabicyclo[3.1.0]hexan-3-yl)pyrimidin-4-yl)amino)methyl)-3-hydroxypiperidin-1-yl)acetamide |
| H1-12 | H6-32 |
|  | rac-2-((3R,4R)-4-(((5-fluoro-6-(2-(4-(trifluoromethyl)phenyl)azetidin-1-yl)pyrimidin-4-yl)amino)methyl)-3-hydroxypiperidin-1-yl)acetamide |

Synthesis of Intermediates

The H1 building blocks were synthesized in accordance with the general methods described in WO2016020295 or as outlined below.

H1 and H3 building blocks were commercially available unless stated below.

Finally, "I" intermediates were synthesized from the corresponding commercial building block as described below.

Synthesis of (R)-2-(4,4-difluoropyrrolidin-2-yl)-5-(trifluoromethyl)pyridine, H1-5

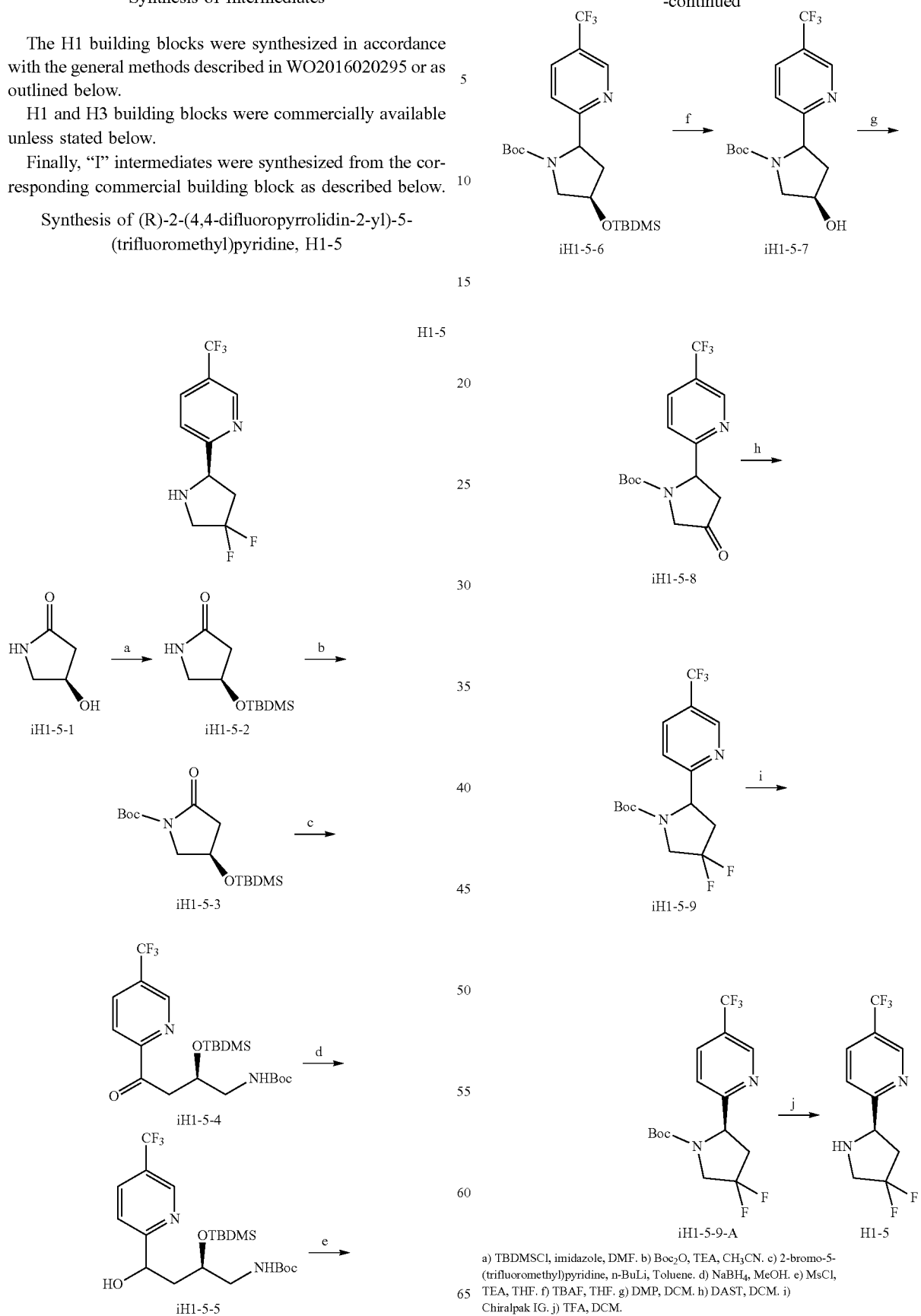

a) TBDMSCl, imidazole, DMF. b) Boc₂O, TEA, CH₃CN. c) 2-bromo-5-(trifluoromethyl)pyridine, n-BuLi, Toluene. d) NaBH₄, MeOH. e) MsCl, TEA, THF. f) TBAF, THF. g) DMP, DCM. h) DAST, DCM. i) Chiralpak IG. j) TFA, DCM.

Synthesis of (R)-4-((tert-butyldimethylsilyl)oxy)pyrrolidin-2-one, iH1-5-2

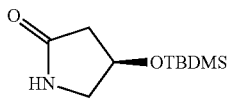

iH1-5-2

Imidazole (9.09 g, 134 mmol) and TBDMSCl were added to a mixture of (R)-4-hydroxypyrrolidin-2-one (9.0 g, 89.1 mmol) in DMF (50 mL) at 0° C. The reaction mixture was then stirred at 25° C. for 3 hours and then water (200 mL) was added, the resulting precipitate was collected by filtration and dried in vacuo to give compound iH1-5-2 (15.5 g, 80.7%) as a white solid.

$^1$H-NMR (300 MHz, DMSO-$d_6$): δ 7.55 (d, J=0.9 Hz, 1H), 4.51-4.48 (m, 1H), 3.50-3.46 (m, 1H), 3.01-2.98 (m, 1H), 2.47-2.42 (m, 1H), 1.95-1.89 (m, 1H), 0.85 (s, 9H), 0.11-0.05 (m, 6H).

Synthesis of (R)-tert-butyl 4-((tert-butyldimethylsilyl)oxy)-2-oxopyrrolidine-1-carboxylate, iH1-5-3

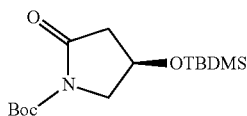

iH1-5-3

TEA (7.49 mL, 53.7 mmol), DMAP (5.47 g, 44.8 mmol) and (Boc)$_2$O (12.5 mL, 53.7 mmol) were sequentially added to a solution of compound iH1-5-2 (9.64 g, 44.8 mmol) in CH$_3$CN (90 mL) 0° C. The reaction mixture was stirred at rt on and then partitioned between EA and water. The separated organic layer was washed with sat NH$_4$Cl and brine, dried (Na$_2$SO$_4$), filtered and concentrated in vacuo. The residue was purified by Flash CC (Hex:EA=3:1) to afford compound iH1-5-3 (13.4 g, 95%) as a pale brown solid.

$^1$H-NMR (300 MHz, DMSO-$d_6$): δ 4.44-4.41 (m, 1H), 3.87-3.82 (m, 1H), 3.49-3.45 (m, 1H), 2.85-2.79 (m, 1H), 2.24-2.16 (m, 1H), 1.44-1.42 (m, 9H), 0.84 (s, 9H), 0.07 (s, 6H).

Synthesis of (R)-tert-butyl (2-((tert-butyldimethylsilyl)oxy)-4-oxo-4-(5-(trifluoromethyl)pyridin-2-yl)butyl)carbamate, iH1-5-4

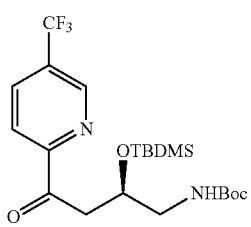

iH1-5-4

Under a N$_2$ atmosphere n-BuLi (25.4 mL, 2.5 M, 63.5 mmol) was added dropwise to a solution of 2-bromo-5-(trifluoromethyl)pyridine (10.7 g, 47.61 mmol) in dry toluene (100 mL) at −70° C. After stirring for 2 hours, iH1-5-3 (10 g, 31.7 mmol), dissolved in dry toluene (30 mL), was added dropwise and the reaction mixture was then stirred for 2h at −70° C. The reaction was warmed to rt and quenched with H$_2$O (300 mL). The mixture was extracted with EA (3×200 mL), washed with brine (3×200 mL), dried (Na$_2$SO$_4$), filtered and concentrated in vacuo to yield crude iH1-5-4 (18 g, crude, >100%).

Synthesis of tert-butyl ((2R)-2-((tert-butyldimethylsilyl)oxy)-4-hydroxy-4-(5-(trifluoromethyl)pyridin-2-yl)butyl)carbamate, iH1-5-5

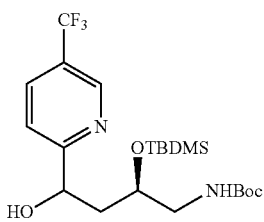

iH1-5-5

Crude iH1-5-4 (18 g, 39.0 mmol) was dissolved in MeOH (100 mL) cooled to 0° C., thereafter NaBH$_4$ (2.4 g, 63.5 mmol) was added. After stirring at rt for 2 h, the mixture was quenched with H$_2$O (200 mL). The mixture was extracted with EA (3×100 mL) and the combined organic phase was washed with brine (200 mL×2), dried (Na$_2$SO$_4$), filtered and concentrated in vacuo. The residue thereof was purified by Flash CC (EA:PE=1:10 to 1:3) to give iH1-5-5 (4.3 g, 23.8%) as a yellow oil.

LCMS: MS Calcd.: 464; MS Found: 465 ([M+1]$^+$).

Synthesis of (4R)-tert-butyl 4-((tert-butyldimethylsilyl)oxy)-2-(5-(trifluoromethyl)pyridin-2-yl)pyrrolidine-1-carboxylate, iH1-5-6

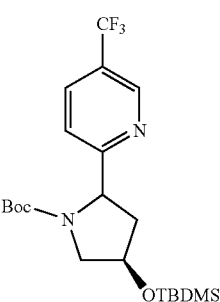

iH1-5-6

Under a N$_2$ atmosphere TEA (4.68 g, 46.3 mmol) and MsCl (2.64 g, 23.2 mmol) were added to a solution of iH1-5-5 (2.15 g, 4.63 mmol) in dry THF (30 mL) at 0° C. The reaction was stirred at 80° C. for 2 days, cooled to rt and quenched with H$_2$O (200 mL). The mixture was extracted with EA (3×100 mL), and the combined organic phase was washed with brine (2×200 mL), dried (Na$_2$SO$_4$), filtered and concentrated in vacuo. The residue thereof was purified by Flash CC (EA:PE=1:10 to 1:3) to give iH1-5-6 (1.05 g, 51%) as a yellow oil.

LCMS: MS Calcd.: 446; MS Found: 447 ([M+1]$^+$).

117

Synthesis of (4R)-tert-butyl 4-hydroxy-2-(5-(trifluoromethyl)pyridin-2-yl)pyrrolidine-1-carboxylate, iH1-5-7

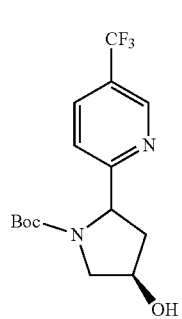

iH1-5-7

TBAF (7.9 g, 25.1 mmol) was added to a solution of compound iH1-5-6 (5.6 g, 12.6 mmol) in dry THF (30 mL). The reaction was stirred at rt for 2 h. Thereafter, the reaction was quenched by the addition of H$_2$O (200 mL) and the mixture was extracted with EA (3×100 mL). The combined organic layer was washed with brine (2×100 mL), dried (Na$_2$SO$_4$), filtered and concentrated in vacuo. The residue thereof was purified by Flash CC (EA:PE=1:3 to 4:5) to give iH1-5-7 (2.73 g, 65.5%) as a yellow solid.

LCMS: MS Calcd.: 332; MS Found: 333 ([M+1]$^+$).

Synthesis of tert-butyl 4-oxo-2-(5-(trifluoromethyl)pyridin-2-yl)pyrrolidine-1-carboxylate, iH1-5-8

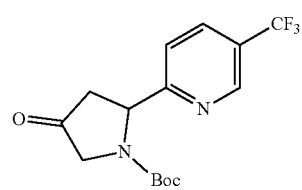

iH1-5-8

DMP (20.8 g, 49.1 mmol) was added to a solution of compound iH1-5-7 (3.26 g, 9.82 mmol) in DCM (40 mL) at 0° C. The reaction was stirred at rt for 12 hours and then H$_2$O (200 mL) was added. The mixture was extracted with EA (3×100 mL). The combined organic phase was washed with aqueous NaHSO$_3$, brine (2×100 mL), dried (Na$_2$SO$_4$) and concentrated in vacuo. The residue was purified by Flash CC (EA:PE=1:10 to 1:3) to give iH1-5-8 (2.1 g, 64.8%) as a yellow oil.

LCMS: MS Calcd.: 330.1; MS Found: 331.3 ([M+1]$^+$).

118

Synthesis of tert-butyl 4,4-difluoro-2-(5-(trifluoromethyl)pyridin-2-yl)pyrrolidine-1-carboxylate, iH1-5-9, and chiral separation into iH1-5-9-1 and iH1-5-9-2

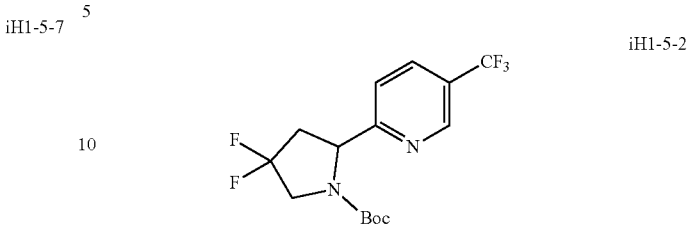

iH1-5-2

Under a N2 atmosphere DAST was added to a solution of iH1-5-8 (2.1 g, 6.36 mmol) in dry DCM (30 mL) −70° C. The reaction was allowed to slowly reach rt and then stirred at rt for 12 h. The mixture was quenched with sat NaHCO$_3$, and the mixture was extracted with EA (3×100 mL). The organic phase was washed with brine (2×100 mL), dried (Na$_2$SO$_4$), filtered and concentrated in vacuo. The residue that was purified by Flash CC (EA:PE=1:10 to 1:3) to give compound iH1-5-9 (1.5 g, 67%) as a yellow oil.

LCMS: MS Calcd.: 352; MS Found: 353 ([M+1]$^+$).

Thereafter iH1-5-9 was separated into the enantiomers using chiral chromatography (Chiralpak IG, Hex:EtOH=90:10) yielding:
iH1-5-9-1, 470 mg (1$^{st}$ eluting isomer)
iH1-5-9-2, 960 mg (2$^{nd}$ eluting isomer)

Synthesis of (R)-2-(4,4-difluoropyrrolidin-2-yl)-5-(trifluoromethyl) trifluoroacetate, H1-5

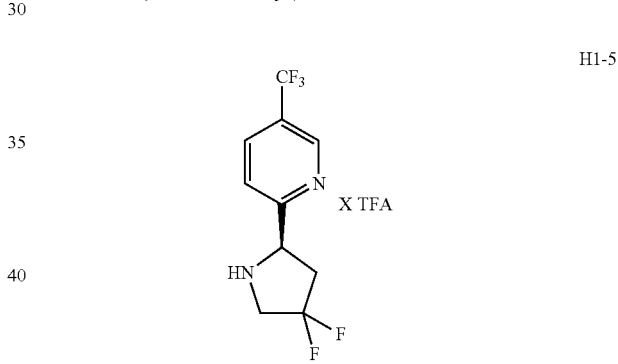

H1-5

TFA (5 mL) was added to a solution of iH1-5-9-1 (470 mg, 1.33 mmol) in DCM (10 mL). After stirring at rt for 2 h, the mixture was concentrated in vacuo to give crude H1-5 (790 mg, >100%).

LCMS: MS Calcd.: 252; MS Found: 253 ([M+1]$^+$).

Synthesis of rac-(3R,5S)-3-methyl-5-(4-(trifluoromethyl)phenyl)morpholine, H1-7

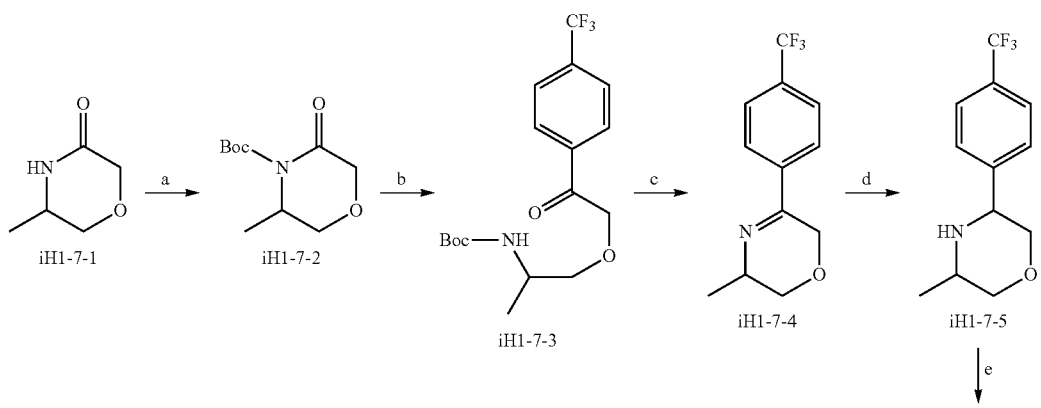

-continued

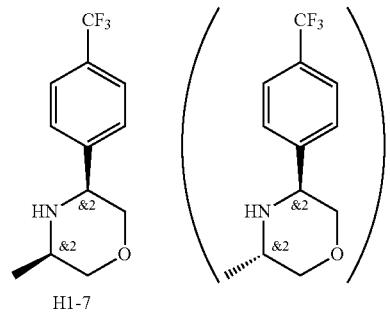

H1-7

Synthesis of tert-butyl 3-methyl-5-oxomorpholine-4-carboxylate, iH1-7-2

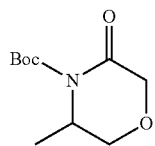

iH1-7-2

Under N₂ atmosphere, a round bottom flask was loaded with 6-methylpiperidin-2-one (10 g, 86.4 mmol), dry THF (50 mL), di-tert-butyl carbonate (26.5 g, 120 mmol), and DMAP (1.1 g, 8.2 mmol) and the contents were stirred on. Imidazole (5.9 g, 86.9 mmol) was added at the mixture was stirred for another 30 min before the addition of EA (60 mL). The mixture was washed with aq HCl (15 mL, 1%), aq at NaHCO₃ (20 mL) and the organic phase was dried (Na₂SO₄), filtered and concentrated in vacuo. The residue was purified by Flash CC (EA:PE=1:10) to give iH1-7-2 (8 g, 37 mmol) as an oil.

Synthesis of tert-butyl (1-(2-oxo-2-(4-(trifluoromethyl)phenyl)ethoxy)propan-2-yl(carbamate, iH1-7-3

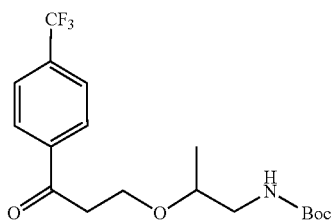

iH1-7-3

Under a N₂ atmosphere n-BuLi (25 mL, 2.5 M) was added to a solution of 1-bromo-4-(trifluoromethyl)benzene (3.5 g, 15.6 mmol) in dry THF (50 mL) at −78° C. After stirring at −60° C. for 30 min iH1-7-2 (4.0 g, 18.7 mmol) was added. The reaction was stirred at −60° C. for 1 h and the quenched with sat NH₄Cl and allowed to reach rt. The mixture was extracted with EA and the combined organic phase was washed with brine and dried (Na₂SO₄), filtered and concentrated in vacuo. The residue was purified by Flash CC (EA:PE=30:70) to yield iH1-7-3 (2.4 g, 6.4 mmol) as an oil.

Synthesis of 3-methyl-5-(4-(trifluoromethyl)phenyl)-3,6-dihydro-2H-1,4-oxazine, iH1-7-4

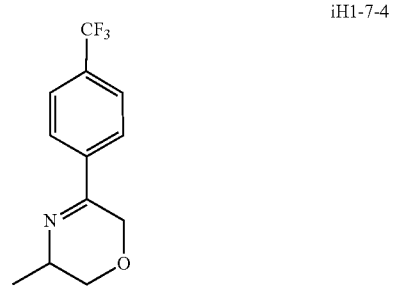 [SMILES: CC1COCC(c2ccc(C(F)(F)F)cc2)=N1]

iH1-7-4 iH1-7-3 (2.4 g, 6.4 mmol) was added to a mixture of TFA/DCM (20 mL/10 mL) and stirred at rt for 2 h. Concentration in vacuo gave crude iH1-7-4 (4 g) as a yellow oil.

Synthesis of 3-methyl-5-(4-(trifluoromethyl)phenyl) morpholine, iH1-7-5, and isolation of rac-(3R,5S)-3-methyl-5-(4-(trifluoromethyl)phenyl)morpholine, H1-7, and separation into H1-7-1 and H1-7-2

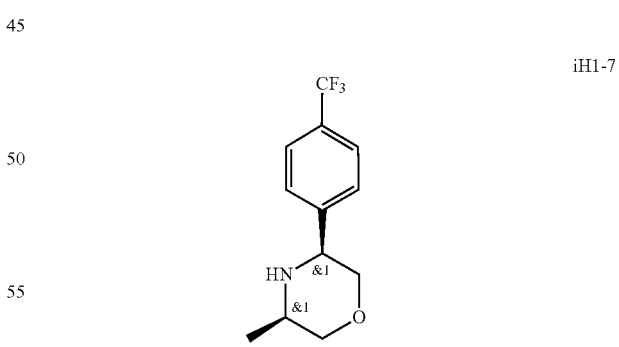

iH1-7

NaBH₄ (0.47 g, 12.4 mmol) was added to a solution of crude iH-7-4 (1 g) in MeOH (20 mL) at 0° C. The reaction was then stirred at rt for 12 h and quenched by the addition of water and the resulting mixture was extracted with EA. The combined organic phase was washed with brine, dried (Na₂SO₄), filtered and concentrated in vacuo. The residue was purified by flash CC (PE:EA=3 to 30% EA) to obtain iH1-7-5 (200 mg, 0.82 mmol) as an oil.

H1-7 was then purified (Chiralcel® OD-H, Hex:IPA=98:2) to yield:

H1-7-1 (80 mg, 1st eluting isomer).

H1-7-2 (80 mg, 2nd eluting isomer).

H1-6-1 and H1-6-2 were synthesized as outlined for H1-7-1 and H1-7-2, but using 1-bromo-3-(trifluoromethyl)benzene instead of 1-bromo-4-(trifluoromethyl)benzene.

Synthesis of 1-(6-(trifluoromethyl)pyridin-3-yl)-2-azabicyclo[3.1.0]hexane, H1-13 and isolation of the stereo isomer H1-13-2

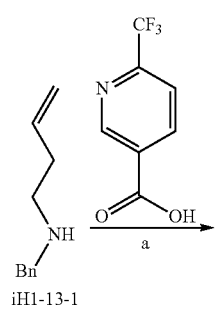
iH1-13-1

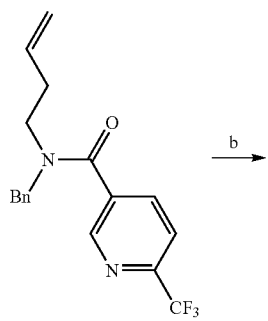
iH1-13-2

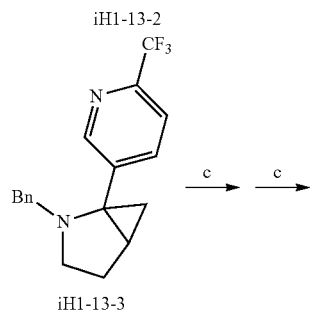
iH1-13-3

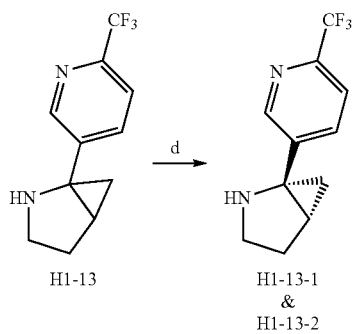
H1-13     H1-13-1 & H1-13-2

Synthesis of N-benzyl-N-(but-3-en-1-yl)-6-(trifluoromethyl)nicotinamide, iH1-13-2

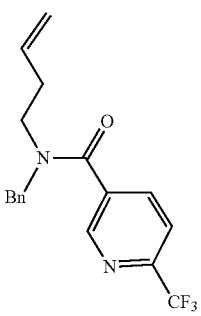
iH1-13-2

Under a N$_2$ atmosphere, TEA followed by HATU, were added to a solution of 1, N-benzylbut-3-en-1-amine (12 g, 75 mmol)), and 2,6-(trifluoromethyl)nicotinic acid (14.3 g, 75 mmol) in dry DMF. The reaction was then stirred on at rt, quenched with H$_2$O and the mixture was then extracted with EA. The combined organic phase was washed with H$_2$O, brine and thereafter concentrated. The resulting residue was purified by Flash CC (EA:PE=1:3) to yield iH1-13-2 (12 g, 36 mmol).

Synthesis of 2-benzyl-1-(6-(trifluoromethyl)pyridin-3-yl)-2-azabicyclo[3.1.0]hexane, iH1-13-3

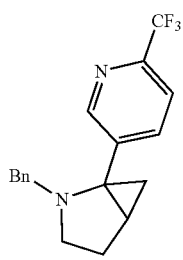
iH1-13-3

Ti(OiPr)$_4$ was added to an ice cooled solution of iH1-13-2 (12 g, 36 mmol) in dry THF. Thereafter, a solution of cyclopentylmagnesium chloride (100 mL, 2M) was slowly added in order to maintain the reaction temperature below 10° C. The reaction was then stirred at rt on and quenched with aq NH$_4$Cl (sat). The mixture was filtered, and the filtrate was extracted with EA. The EA phase was washed with H$_2$O and brine and then concentrated. The residue was purified by Flash CC (EA:PE=1:15) to give iH1-13-3 (3.8 g, 12 mmol).

Synthesis of 1-(6-(trifluoromethyl)pyridin-3-yl)-2-azabicyclo[3.1.0]hexane, H1-13 and isolation of H1-13-2

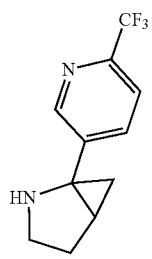

At rt ACE-Cl (1-chloroethyl chloroformate) was added to a solution of iH1-13-3 (3.2 g, 10 mmol) in DCE (50 mL) and the solution was heated to reflux for 19 h. The DCE was then removed and MeOH (50 mL) was added and the reaction was refluxed for 3 h. The reaction was concentrated, and the residue was purified by Prep HPLC. to yield H1-13 (500 mg, 2.2 mmol).

After purification of iH1-13(CHIRALPAK IC, Hex: EtOH=90:10) two stereoisomers were obtained.

H1-13-1 1$^{st}$ eluting peak (100 mg)

H1-13-2 2$^{nd}$ eluting peak (100 mg)

Synthesis of 2-(6-(trifluoromethyl)pyridin-3-yl)-3-azabicyclo[3.1.0]hexane, H1-14

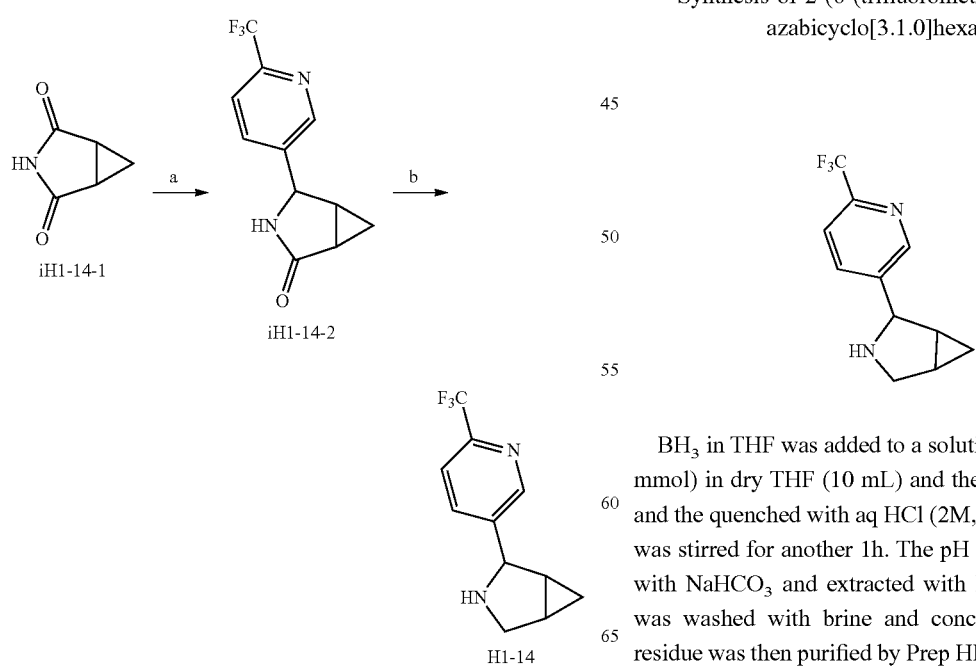

Synthesis of 4-(6-(trifluoromethyl)pyridin-3-yl)-3-azabicyclo[3.1.0]hexan-2-one, iH1-14-2

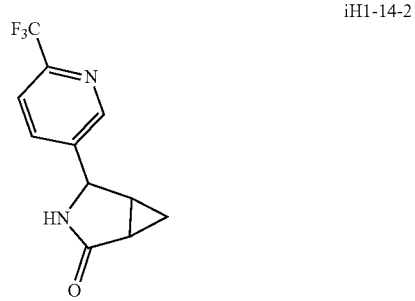 [SMILES: O=C1NC(c2ccc(C(F)(F)F)nc2)C2CC12]

Under an inert atmosphere a solution of iPrMgCl (45 mL, 2M) was added to a 0° C. solution of 5-bromo-2-(trifluoromethyl)pyridine (19 g, 80 mmol) in dry THF (100 mL) and stirred for 4 h. Thereafter the Grignard reagent in solution was cooled to −78° C. and then a solution of 3-azabicyclo[3.1.0]hexane-2,4-dione (4.6 g, 40 mmol) in dry THF was added. The reaction was allowed to reach rt and stirred at ambient temp for 8 h. Thereafter NaBH$_3$CN (2.5 g, 40 mmol) followed by HCl (13 mL, 0.16 mol) were added and the reaction was stirred for another 4h. The resulting mixture was extracted with DCM. The DCM phase was washed with brine, dried (Na$_2$SO$_4$), filtered and concentrated in vacuo. The residue was purified by Flash CC (PE:EA=1:1) to give iH1-14-2 (5 g, 20.6 mmol) as a yellow solid.

Synthesis of 2-(6-(trifluoromethyl)pyridin-3-yl)-3-azabicyclo[3.1.0]hexane, H1-14

BH$_3$ in THF was added to a solution of iH1-14-2 (1 g, 4.1 mmol) in dry THF (10 mL) and the reaction was stirred on and the quenched with aq HCl (2M, 50 mL) and the mixture was stirred for another 1h. The pH was the adjusted to ca 9 with NaHCO$_3$ and extracted with DCM. The DCM phase was washed with brine and concentrated in vacuo. The residue was then purified by Prep HPLC to yield H1-14 (100 mg, 0.43 mmol) as a white solid.

Synthesis of 2-(4-(aminomethyl)piperidin-1-yl)acetamide hydrochloride, 1-1

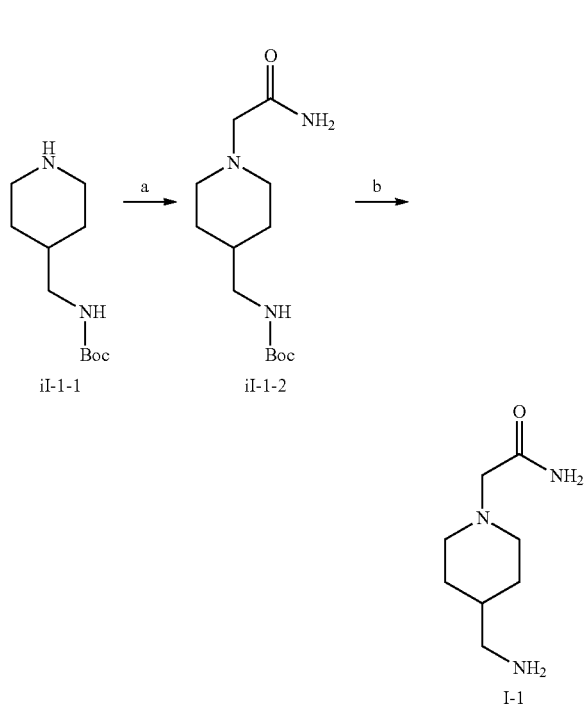

a) DIEA, methyl 2-bromopropanoate, DCM. b) HCl, dioxane.

Synthesis of tert-butyl ((1-(2-amino-2-oxoethyl)piperidin-4-yl)methyl)carbamate, iI-1-2

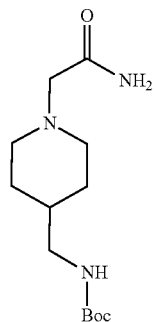

2-Bromoacetamide (724 mg, 5.3 mmol) was added dropwise to an ice-water cooled solution of tert-butyl (piperidin-4-ylmethyl)carbamate iI-1-1 (1.1 g, 5 mmol) in a mixture of DCM (40 mL) and DIEA (5.2 mL). The ice-water bath was removed, and the reaction was allowed to stir at rt for 3h. Thereafter, the reaction was concentrated in vacuo, and the residue was purified by Flash CC (MeOH:DCM). After concentration under reduced pressure the crude was mixed with sat aq NaHCO₃. The mixture was extracted with four times with EA. The combined organic phase was washed once with sat aq NaHCO₃, dried (Na₂SO₄), filtered and concentrated in vacuo to yield iI-1-2 (1.0 g, 3.9 mmol).

LCMS: MS Calcd.: 171; MS Found: 172 ([M+1]$^+$).

$^1$H NMR (300 MHz, Methanol-d₄) δ 3.02-2.87 (m, 6H), 2.13 (td, J=11.5, 2.4 Hz, 2H), 1.75-1.65 (m, 2H), 1.45 (s, 9H), 1.41 (s, 1H), 1.30 (qd, J=12.0, 3.8 Hz, 2H).

2-(4-(Aminomethyl)piperidin-1-yl)acetamide hydrochloride, I-1

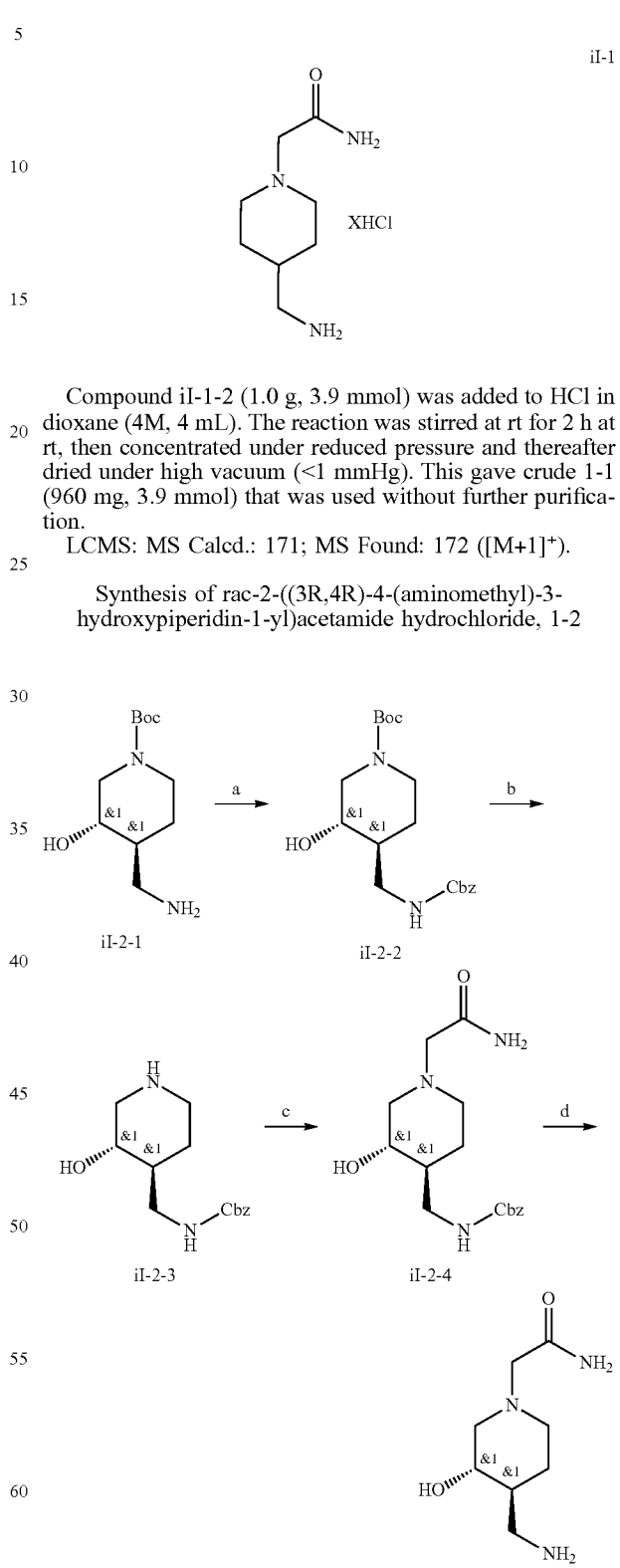

Compound iI-1-2 (1.0 g, 3.9 mmol) was added to HCl in dioxane (4M, 4 mL). The reaction was stirred at rt for 2 h at rt, then concentrated under reduced pressure and thereafter dried under high vacuum (<1 mmHg). This gave crude 1-1 (960 mg, 3.9 mmol) that was used without further purification.

LCMS: MS Calcd.: 171; MS Found: 172 ([M+1]$^+$).

Synthesis of rac-2-((3R,4R)-4-(aminomethyl)-3-hydroxypiperidin-1-yl)acetamide hydrochloride, 1-2 a) CbzCl, NaHCO₃. b) TFA, DCM. c) DMF, 2-bromoacetamide, K₂CO₃. d) Pd/C, H₂, HCl.

Synthesis of rac-tert-Butyl (3R,4R)-4-((((benzyloxy)carbonyl)amino)methyl)-3-hydroxypiperidine-1-carboxylate, iI-2-2

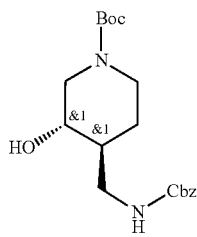

NaHCO$_3$ (3.4 g, 40.5 mmol) and Cbz-Cl (2.7 g, 16.2 mmol) were added to a solution of rac-tert-butyl (3S,4S)-4-(aminomethyl)-3-hydroxypiperidine-1-carboxylate iI-2-1 (4.6 g, 13.5 mmol) in THF/H$_2$O (10 mL/3 mL). The reaction was then stirred at 35° C. for 16 h. H$_2$O (20 mL) was added in and the mixture was extracted with DCM (3×30 mL). The combined organic layers were dried (Na$_2$SO$_4$), filtered and concentrated in vacuo to afford iI-2-2 as a colourless oil (3.8 g, yield 77%), which was used directly in next step without further purification.

LCMS: MS Calcd.: 364; MS Found: 365 ([M+1]$^+$).

rac-Benzyl (((3R,4R)-3-hydroxypiperidin-4-yl)methyl)carbamate, iI-2-3

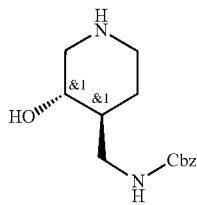

TFA (5 mL) was added to a solution of iI-2-2 (3.8 g, 10.7 mmol) in DCM (10 mL) and the reaction was stirred at rt for 5 h. The mixture was concentrated in vacuo to yield iI-2-3 as a brown oil (3.2 g). which was used directly in next step without further purification.

LCMS: MS Calcd.: 264; MS Found: 265 ([M+1]$^+$).

rac-Benzyl (((3R,4R)-1-(2-amino-2-oxoethyl)-3-hydroxypiperidin-4-yl)methyl)carbamate, iI-2-4

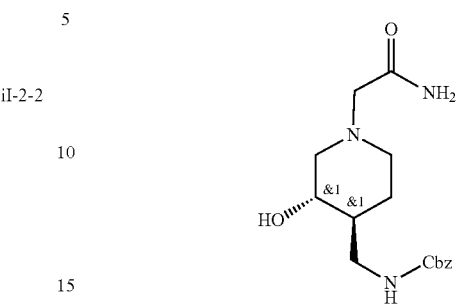

K$_2$CO$_3$ (4.43 g, 32.1 mmol) and 2-bromoacetamide (1.77 g, 12.8 mmol) were added to a solution of crude iI-2-3 (3.21 g, 10.7 mmol) in DMF (10 mL) and the reaction was stirred at 35° C. for 16 h. Then H$_2$O (120 mL) was added and the mixture was extracted with EA (3×30 mL). The combined organic layers were dried (Na$_2$SO$_4$), filtered and concentrated. The residue was purified by HPLC to afford trans iI-2-4 as a white solid (500 mg, 1.6 mmol).

LCMS: MS Calcd.: 321; MS Found: 322 ([M+1]$^+$).

rac-2-((3R,4R)-4-(Aminomethyl)-3-hydroxypiperidin-1-yl)acetamide hydrochloride, 1-2

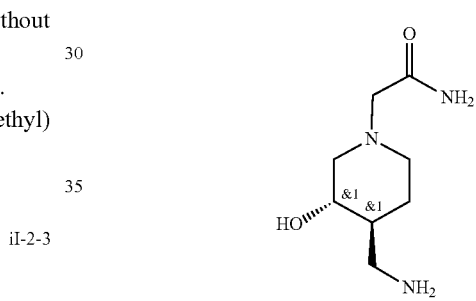

Pd/C (10%, 100 mg) was added to a solution of iI-2-4 (500 g, 1.56 mmol) in MeOH (30 mL) and the reaction was stirred at 35° C. for 3 h under a H$_2$ atmosphere (50 psi). The mixture was filtered and concentrated under reduced pressure to afford crude 1-2 as a white solid (300 mg). Thereafter, the solid was stirred in HCl/1,4-dioxane (4 M) to afford a white solid as the hydrogen chloride salt (54 mg, yield 15%).

$^1$H-NMR (400 MHz, CD3OD): δ 3.85 (s, 2H), 53.70-3.76 (m, 1H), δ 3.38-3.49 (m, 2H), δ 3.08-3.13 (m, 1H), δ 2.96-3.13 (m, 1H), δ 2.86-2.91 (m, 1H), δ 2.77-2.83 (m, 1H), δ 1.95-1.99 (m, 1H), δ 1.81-1.82 (m, 1H), δ 1.51-1.62 (m, 1H).

MS Calcd.: 187; MS Found: 188 ([M+1]$^+$).

Analytical data.

| Ex. No. | Chiral separation | $^1$H-NMR | m/z (M + H)$^+$ |
|---|---|---|---|
| H6-1 | | (300 MHz, DMSO-d$_6$) δ 8.99-8.88 (m, 1H), 8.17 (ddd, J = 8.3, 2.4, 0.8 Hz, 1H), 7.80 (d, J = 1.8 Hz, 1H), 7.57 (d, J = 8.3 Hz, 1H), 7.08 (d, J = 761.0 Hz, 2H), 6.95 (d, J = 3.2 Hz, 1H), 5.47 (s, 1H), 4.55 (d, J = 11.2 Hz, 1H), 4.17-4.04 (m, 1H), 3.99-3.76 (m, 2H), 3.71-3.43 (m, 2H), 3.16 (d, J = 5.2 Hz, 3H), 2.92 (q, J = 6.9 Hz, 1H), 2.71 (t, J = 10.8 Hz, 2H), 2.19-1.90 (m, 2H), 1.71-1.43 (m, 3H), 1.15 (q, J = 11.9, 11.4 Hz, 2H), 1.03 (d, J = 6.9 Hz, 3H). | 512 |

-continued

| Ex. No. | Chiral separation | ¹H-NMR | m/z (M + H)⁺ |
|---|---|---|---|
| H6-2 | | (300 MHz, DMSO-$d_6$) δ 8.95 (s, 1H), 8.22-8.13 (m, 1H), 7.81 (d, J = 1.8 Hz, 1H), 7.58 (d, J = 8.4 Hz, 1H), 7.19-7.00 (m, 3H), 5.48 (s, 1H), 4.55 (d, J = 11.5 Hz, 1H), 4.13 (d, J = 12.8 Hz, 1H), 3.93 (dd, J = 11.7, 3.7 Hz, 1H), 3.88-3.79 (m, 1H), 3.74-3.45 (m, 2H), 3.27-3.11 (m, 2H), 2.85-2.70 (m, 4H), 2.02-1.87 (m, 2H), 1.67-1.45 (m, 3H), 1.31-1.09 (m, 2H). | 498 |
| H6-3 | | (300 MHz, DMSO-$d_6$) δ 8.98-8.92 (m, 1H), 8.18 (ddd, J = 8.3, 2.4, 0.8 Hz, 1H), 7.80 (d, J = 1.9 Hz, 1H), 7.58 (d, J = 8.3 Hz, 1H), 7.14-7.01 (m, 2H), 6.90 (d, J = 3.6 Hz, 1H), 5.47 (s, 1H), 4.55 (d, J = 11.6 Hz, 1H), 4.20-4.04 (m, 1H), 3.93 (dd, J = 11.7, 3.8 Hz, 1H), 3.89-3.79 (m, 1H), 3.70-3.44 (m, 2H), 3.25-3.10 (m, 2H), 2.76-2.65 (m, 2H), 1.98 (t, J = 10.9 Hz, 2H), 1.71-1.58 (m, 2H), 1.58-1.43 (m, 1H), 1.28-1.09 (m, 2H), 1.03 (s, 6H). | 526 |
| H6-4 | | (300 MHz, DMSO-$d_6$) δ 7.86 (d, J = 1.7 Hz, 1H), 7.75-7.67 (m, 2H), 7.59 (d, J = 8.2 Hz, 2H), 7.24-7.12 (m, 2H), 7.08 (s, 1H), 5.45 (s, 1H), 4.30 (dd, J = 12.1, 2.3 Hz, 1H), 4.05-3.79 (m, 3H), 3.74-3.46 (m, 4H), 2.84 (s, 2H), 2.69-2.54 (m, 2H), 2.33-2.18 (m, 2H), 1.88-1.61 (m, 4H). | 515 |
| H6-5 | | (300 MHz, CD$_3$OD) δ 7.83 (d, J = 1.6 Hz, 1H), 7.61 (s, 4H), 5.43 (t, J = 3.4 Hz, 1H), 4.29 (dd, J = 12.1, 2.9 Hz, 1H), 4.00 (dd, J = 12.1, 3.6 Hz, 1H), 3.96-3.85 (m, 2H), 3.84-3.71 (m, 1H), 3.48-3.35 (m, 1H), 3.30-3.26 (m, 2H), 2.97 (s, 2H), 2.94-2.83 (m, 2H), 2.11 (td, J = 11.7, 2.4 Hz, 2H), 1.81-1.68 (m, 2H), 1.68-1.54 (m, 1H), 1.40-1.24 (m, 2H). | 497 |
| H6-6 | | ¹H NMR (300 MHz, DMSO-$d_6$) δ 7.87 (d, J = 1.7 Hz, 1H), 7.54-7.46 (m, 2H), 7.38-7.29 (m, 2H), 7.27-7.00 (m, 3H), 5.41 (s, 1H), 4.28 (dd, J = 12.1, 2.2 Hz, 1H), 4.04-3.79 (m, 3H), 3.72-3.49 (m, 4H), 3.30-3.22 (m, 1H), 2.84 (s, 2H), 2.68-2.56 (m, 2H), 2.31-2.15 (m, 2H), 1.91-1.59 (m, 4H). | 531 |
| H6-7 | | (300 MHz, DMSO-$d_6$) δ 7.85 (d, J = 1.7 Hz, 1H), 7.71 (d, J = 8.3 Hz, 2H), 7.59 (d, J = 8.2 Hz, 2H), 7.22-7.03 (m, 2H), 7.03-6.91 (m, 1H), 5.43 (s, 1H), 4.96 (d, J = 5.2 Hz, 1H), 4.28 (dd, J = 12.1, 2.4 Hz, 1H), 4.03-3.81 (m, 3H), 3.66 (td, J = 11.0, 2.9 Hz, 1H), 3.59-3.46 (m, 1H), 3.26 (s, 1H), 3.17 (d, J = 5.2 Hz, 1H), 2.90-2.77 (m, 3H), 2.74-2.61 (m, 1H), 2.00-1.74 (m, 2H), 1.70-1.55 (m, 1H), 1.48-1.32 (m, 1H), 1.32-1.14 (m, 1H). | 513 |
| H6-7-1 | IG (Hex:EtOH = 70:30) | (400 MHz, DMSO-$d_6$): δ 7.85 (s, 1H), 7.72-7.70 (d, J = 8.4 Hz, 2H), 7.60-7.58 (d, J = 8.0 Hz, 2H), 7.14 (s, 1H), 7.08 (s, 1H), 6.99 (s, 1H), 5.43 (s, 1H), 4.97 (d, J = 5.2Hz, 1H), 4.30-4.27 (d, J = 12 Hz, 1H), 3.97-3.84 (m, 3H), 3.69-3.64 (m, 1H), 3.56-3.51 (m, 1H), 3.36-3.35 (m, 1H), 3.31-3.28 (m, 2H), 2.86-2.81 (m, 3H), 2.70-2.69 (d, J = 10.8 Hz, 1H), 1.92-1.89 (m, 1H), 1.85-1.80 (m, 1H), 1.64-1.61(m, 1H), 1.40-1.39 (m, 1H), 1.27-1.24(m, 1H); | 513 |
| H6-7-2 | IG (Hex:EtOH = 70:30) | (400 MHz, DMSO-$d_6$): δ 7.86 (s, 1H), 7.72-7.70 (d, J = 8.0 Hz, 2H), 7.60-7.58 (d, J = 8.0 Hz, 2H), 7.15 (s, 1H), 7.09 (s, 1H), 6.99 (s, 1H), 5.44 (s, 1H), 4.97 (d, J = 5.2 Hz, 1H), 4.28 (d, J = 11.6 Hz, 1H), 3.98-3.84 (m, 3H), 3.69-3.64 (m, 1H), 3.54-3.50 (m, 1H), 3.35-3.34 (m, 1H), 3.30-3.29 (m, 2H), 2.86-2.70 (m, 3H), 2.70-2.68 (d, J = 10.8 Hz, 1H), 1.95-1.81 (m, 2H), 1.64-1.62 (m, 1H), 1.39 (m, 1H), 1.26-1.23 | 513 |

| Ex. No. | Chiral separation | ¹H-NMR | m/z (M + H)⁺ |
|---|---|---|---|
| H6-08 | | (300 MHz CDCl₃) δ 8.88 (s, 1H), 7.87-7.96 (m, 3H), 7.42-7.45 (m, 1H), 5.57-5.59 (m, 1H), 5.39-5.41 (m, 1H), 5.03-5.07 (m, 1H), 4.78-4.83 (m, 1H), 3.91-4.02 (m, 2H), 3.57-3.79 (m, 4H), 3.43 (s, 2H), 3.04-3.06 (m, 2H), 2.51-2.56 (m, 3H). | 516 |
| H6-09-1 | IC (Hex:EtOH = 60:40) | (400 MHz, CD₃OD): δ7.85 (d, J = 1.6 Hz, 1H), 7.61 (s, 4H), 5.42 (s, 1H), 4.31-4.27 (m, 1H), 4.02-3.98 (m, 1H), 3.92-3.89 (m, 2 H), 3.81-3.75 (m, 2 H), 3.09-3.05 (m, 3 H), 2.91-2.88 (m, 1 H), 2.55-2.48 (m, 1 H), 2.33-2.15 (m, 2H), 1.86-1.83 (m, 1 H), 1.66-1.59 (m, 1 H) | 533 |
| H6-09-2 | IC (Hex:EtOH = 60:40) | (400 MHz, CD₃OD): δ7.85 (d, J = 1.6 Hz, 1 H), 7.61 (s, 4 H), 5.42 (s, 1 H), 4.31-4.27 (m, 1 H), 4.02-3.98 (m, 1 H), 3.92-3.89 (m, 2 H), 3.81-3.75 (m, 2 H), 3.09-3.05 (m, 3 H), 2.91-2.88 (m, 1 H), 2.55-2.48 (m, 1 H), 2.33-2.15 (m, 2 H), 1.86-1.83 (m, 1 H), 1.66-1.59 (m, 1 H) | 533 |
| H6-10-1 | ID (Hex:EtOH = 70:30) | (400 MHz, DMSO-d₆): δ 7.86 (s, 1H), 7.71 (d, J = 8.4 Hz, 2H), 7.60-7.58 (d, J = 8.0 Hz, 2H), 7.18 (s, 1H), 7.09 (s, 2H), 5.44 (s, 1H), 4.30-4.29 (m, 1H), 4.26 (d, J = 1.6 Hz, 1H), 3.97-3.84 (m, 3H), 3.69-3.62 (m, 2H), 3.29-3.26 (m, 2H), 3.07-3.04 (m, 1H), 2.88 (s, 2H), 2.69-2.65 (m, 1H), 2.13-2.11 (m, 1H), 2.01 (s, 1H), 1.75-1.75 (m, 2H), 1.29-1.24 (m, 1H) | 515 |
| H6-10-2 | ID (Hex:EtOH = 70:30) | (400 MHz, DMSO-d₆): δ 7.86 (s, 1H), 7.72-7.70 (d, J = 8.4 Hz, 2H), 7.60-7.58 (d, J = 8.4 Hz, 2H), 7.17 (s, 1H), 7.10 (s, 2H), 5.43 (s, 1H), 4.50-4.36 (m, 1H), 4.38-4.26 (m, 1H), 3.98-3.84 (m, 3H), 3.69-3.63 (m, 2H), 3.30-3.25 (m, 2H), 3.07-3.04 (m, 1H), 2.90 (s, 2H), 2.69-2.67 (m, 1H), 2.12-2.04 (m, 1H), 2.01-1.98 (m, 1H), 1.75-1.70 (m, 2H), 1.28-1.26 (m, 1H) | 515 |
| H6-11-1 | IG (Hex:EtOH = 40:60) | (300 MHz, CD₃OD): δ 8.87 (s, 1H), 8.05-8.08 (m, 1H), 7.84 (s, 1H), 7.58 (d, J = 4.0 Hz, 1H), 5.50-5.51 (m, 1H), 4.63-4.68 (m, 1H), 4.14-4.16 (m, 1H), 4.09-4.11 (m, 1H), 3.88-3.93 (m, 1H), 3.73-3.82 (m, 2H), 3.56-3.65 (m, 1H), 3.43-3.52 (m, 1H), 3.03-3.13 (m, 3H), 2.88-2.95 (m, 1H), 2.44-2.58 (m, 1H), 2.16-2.36 (m, 2H), 1.82-1.90 (m, 1H), 1.58-1.68 (m, 1H). | 534 |
| H6-11-2 | IG (Hex:EtOH = 40:60) | (300 MHz, CD₃OD) δ 8.86 (s, 1H), 8.06-8.08 (m, 1H), 7.84 (s, 1H), 7.57 (d, J = 4.0 Hz, 1H), 5.50-5.51 (m, 1H), 4.64-4.68 (m, 1H), 4.14-4.16 (m, 1H), 4.09-4.11 (m, 1H), 3.88-3.93 (m, 1H), 3.73-3.82 (m, 2H), 3.56-3.65 (m, 1H), 3.43-3.52 (m, 1H), 3.03-3.13 (m, 3H), 2.88-2.95 (m, 1H), 2.44-2.58 (m, 1H), 2.16-2.36 (m, 2H), 1.82-1.90 (m, 1H), 1.59-1.68 (m, 1H). | 534 |
| H6-12-1 | IG (Hex:EtOH:DEA = 40:60:0.3) | (DMSO-d₆, 400 MHz): δ 8.96 (s, 1H), 8.19-8.17 (d, J = 8.0 Hz, 1H), 7.84 (s, 1H), 7.60-7.58 (d, J = 8.4 Hz, 1H), 7.16 (s, 2H), 7.03 (s, 1H), 5.49 (s, 1H), 4.78-4.65 (d, J = 48.4 Hz, 1H), 4.58-4.55 (d, J = 11.6 Hz, 1H), 4.15-4.12 (d, J = 12.8 Hz, 1H), 3.94-3.92 (m, 1H), 3.86-3.83 (d, J = 10.4 Hz, 1H), 3.67-3.61 (m, 1H), 3.56-3.51 (m, 1H), 3.41-3.40 (m, 1H), 3.30-3.24 (m, 1H), 3.07-3.02 (m, 1H), 2.88-2.81 (m, 3H), 2.34-2.11 (m, 2H), 1.88-1.79 (m, 1H), 1.55-1.50 (m, 2H) | 516 |

| Ex. No. | Chiral separation | ¹H-NMR | m/z (M + H)⁺ |
|---|---|---|---|
| H6-12-2 | IG (Hex:EtOH:DEA = 40:60:0.3) | (DMSO-d₆, 400 MHz): δ 8.954(s, 1H), 8.170-8.196(m, 1H), 7.829-7.833(d, J = 1.6, 1H), 7.576-7.597(d, J = 8.4, 1H), 7.152(s, 2H), 7.020(s, 1H), 5.482(s, 1H), 4.652-4.773(d, J = 48.4, 1H), 4.540-4.569(d, J = 11.6, 1H), 4.118-4.149(d, J = 12.4, 1H), 3.911-3.950 (m, 1H), 3.823-3.851(d, J = 11.2, 1H), 3.601-3.662(m, 1H), 3.523-3.584(m, 1H), 3.487-3.495(m, 1H), 3.355-3.373(m, 1H), 3.245-3.293(m, 1H), 3.015-3.075(m, 1H), 2.808-2.872(m, 3H), 2.104-2.333(m, 2H), 1.742-1.775(m, 1H), 1.491-1.542(m, 2H) | 516 |
| H6-13-1 | IG (Hex:EtOH:DEA = 40:60:0.3) | (DMSO-d₆, 400 MHz): δ 8.95 (s, 1H), 8.20-8.18 (m, 1H), 7.82 (s, 1H), 7.60-7.58 (d, J = 8.0 Hz, 1H), 7.19-7.08 (m, 3H), 5.49 (s, 1H), 4.57-4.54 (d, J = 12.0 Hz, 1H), 4.50-4.37 (d, 1H), 4.15-4.12 (d, J = 12.8 Hz, 1H), 3.95-3.91 (m, 1H), 3.85-3.82 (d, J = 10.8 Hz, 1H), 3.66-3.61 (m, 2H), 3.55-3.50 (m, 1H), 3.29-3.24 (m, 1H), 3.06 (s, 1H), 2.90 (s, 2H), 2.69-2.67 (m, 1H), 2.13-2.09 (m, 1H), 2.04-1.99 (m, 1H), 1.78-1.74 (m, 2H), 1.29-1.23 (m, 1H) | 516 |
| H6-13-2 | IG (Hex:EtOH:DEA = 40:60:0.3) | (DMSO-d₆, 400 MHz): δ 8.95 (s, 1H), 8.19-8.18 (d, J = 7.2 Hz, 1H), 7.82 (s, 1H), 7.60-7.58 (d, J = 8.4 Hz, 1H), 7.19-7.08 (m, 3H), 5.48 (s, 1H), 4.57-4.54 (d, J = 11.2 Hz, 1H), 4.52-4.47 (m, 1H), 4.16-4.12 (d, J = 13.2 Hz, 1H), 3.95-3.92 (m, 1H), 3.85-3.83 (d, J = 10.8 Hz, 1H), 3.67-3.61 (m, 2H), 3.55-3.49 (m, 1H), 3.28-3.21 (m, 1H), 3.06 (s, 1H), 2.90 (s, 2H), 2.69-2.67 (d, J = 9.2, 1H), 2.12-2.11 (m, 1H), 2.03-1.98 (m, 1H), 1.77-1.71 (m, 2H), 1.31-1.24 (m, 1H) | 516 |
| H6-14 | ID (CO₂:iPrOH:DEA = (99:1:0.2% to 40:60:0.2%) | (400 MHz, DMSO-d₆) δ 1.41 (d, J = 13.2 Hz, 2H), 1.47-1.62 (m, 2H), 2.27-2.44 (m, 2H), 2.83 (bs, 2H), 2.97-3.21 (m, 3H), 4.26 (dq, J = 55.1, 12.7, 11.9 Hz, 4H), 4.54 (s, 2H), 5.63 (dd, J = 8.6, 4.2 Hz, 1H), 6.64-6.73 (m, 1H), 7.11 (d, J = 27.3 Hz, 2H), 7.50 (d, J = 8.2 Hz, 2H), 7.68 (d, J = 8.2 Hz, 2H), 7.77 (d, J = 1.7 Hz, 1H). | 533 |
| H6-15-1 | IF (Hex:EtOH = 60:40) | (400 MHz, CDCl₃): δ 7.88 (s, 1H), 7.57 (d, J = 8.4 Hz, 2H), 7.34 (d, J = 8.0 Hz, 2H), 6.95 (br s, 1H), 5.61-5.53 (m, 2H), 4.89 (br s, 1H), 4.31-4.15 (m, 2H), 3.76-3.57 (m, 2H), 3.13-3.01 (m, 3H), 2.95-2.86 (m, 2H), 2.48-2.29 (m, 3H), 2.13-2.02 (m, 1H), 1.84-1.81 (m, 1H), 1.63-1.57 (m, 1H). | 553 |
| H6-15-2 | IF (Hex:EtOH = 60:40) | (400 MHz, CDCl₃): δ 7.88 (s, 1H), 7.57 (d, J = 8.4 Hz, 2H), 7.34 (d, J = 8.4 Hz, 2H), 6.95 (br s, 1H), 5.61-5.58 (m, 1H), 5.50 (br s, 1H), 4.90 (br s, 1H), 4.31-4.16 (m, 2H), 3.76-3.64 (m, 2H), 3.14-3.01 (m, 3H), 2.93-2.88 (m, 2H), 2.48-2.29 (m, 3H), 2.13-2.02 (m, 1H), 1.85-1.81 (m, 1H), 1.66-1.58 (m, 1H). | 553 |
| H6-16-1 | IC (CO₂:MeOH:DEA = 70:30:0.3) | (400 MHz, DMSO-d₆): δ 7.78 (d, J = 2.0 Hz, 1H), 7.67 (d, J = 8.4 Hz, 2H), 7.49 (d, J = 8.4 Hz, 2H), 7.16 (s, 1H), 7.08-7.02 (m, 2H), 5.64-5.61 (m, 1H), 4.47-4.17 (m, 3H), 3.56-3.16 (m, 1H), 3.30-3.25 (m, 1H), 3.06-3.03 (m, 2H), 2.88 (s, 2H), 2.67-2.65 (m, 1H), 2.40-2.33 (m, 1H), 2.12-2.08 (m, 1H), 2.02-1.96 (m, 1H), 1.74-1.67 (m, 2H), 1.30-1.22 (m, 1H) | 535 |
| H6-16-2 | IC (CO₂:MeOH:DEA = 70:30:0.3) | (400 MHz, DMSO-d₆): δ 7.78 (d, J = 2.0 Hz, 1H), 7.67 (d, J = 8.4 Hz, 2H), 7.49 (d, J = 8.4 Hz, 2H), 7.16 (s, 1H), 7.08-7.04 (m, 2H), 5.64-5.61(m, 1H), 4.35-4.17 (m, 3H), 3.67-3.63 (m, 1H), 3.22-3.18 (m, 1H), 3.05-3.04 (m, 2H), 2.88 (s, 2H), 2.68-2.64 (m, 1H), 2.41-2.34 (m, 1H), 2.13-2.08 (m, 1H), 2.01-1.96 (m, 1H), 1.72-1.68 (m, 2H), 1.28-1.24 (m, 1H) | 535 |

-continued

| Ex. No. | Chiral separation | ¹H-NMR | m/z (M + H)⁺ |
|---|---|---|---|
| H6-17 | | (400 MHz, CDCl3) δ 1.40 (m, 1H), 1.50 (m, 1H), 1.56-1.64 (m, 1H), 2.10 (td, J = 10.4, 3.4 Hz, 1H), 2.17 (td, J = 11.4, 2.5 Hz, 1H), 2.40 (dtt, J = 18.2, 9.0, 4.2 Hz, 1H), 2.77-2.97 (m, 2H), 3.00 (d, J = 1.2 Hz, 3H), 3.09 (dddd, J = 17.2, 12.9, 6.5, 3.6 Hz, 1H), 3.27 (m, 1H), 4.00-4.12 (m, 1H), 4.15-4.35 (m, 2H), 4.98 (brd, J = 7.3 Hz, 1H), 5.36-5.40 (m, 2H), 5.60 (q, J = 8.5 Hz, 1H), 6.88 (s, 1H), 7.35 (d, J = 7.0 Hz, 2H), 7.58 (d, J = 8.2 Hz, 2H), 7.85 (dd, J = 7.8, 1.5 Hz, 1H). | 533 |
| H6-17-1 | ID (CO₂:iPrOH:DEA = 99:1:0.2% to 55:45:0.2%) | (400 MHz, CDCl₃) δ 1.40 (m, 1H), 1.54 (dd, J = 12.1, 4.0 Hz, 1H), 1.57-1.65 (m, 1H), 2.10 (t, J = 10.3 Hz, 1H), 2.18 (td, J = 11.4, 2.8 Hz, 1H), 2.38 (m, 1H), 2.77-3.06 (m, 6H), 3.11 (ddd, J = 14.6, 5.6, 2.8 Hz, 1H), 3.29 (td, J = 9.9, 4.4 Hz, 1H), 4.07 (ddd, J = 14.6, 7.7, 3.2 Hz, 1H), 4.13-4.39 (m, 2H), 5.01 (m, 1H), 5.62 (dd, J = 8.5, 5.8 Hz, 1H), 5.67 (brs, 1H), 6.90 (s, 1H), 7.35 (d, J = 8.2 Hz, 2H), 7.58 (d, J = 8.2 Hz, 2H), 7.84 (d, J = 1.5 Hz, 1H). | 533 |
| H6-17-2 | ID (CO₂:iPrOH:DEA = 99:1:0.2% to 55:45:0.2%) | (400 MHz, CDCl₃) δ 1.40 (m, 1H), 1.49 (tt, J = 12.2, 6.1 Hz, 1H), 1.60 (m, 1H), 2.10 (t, J = 10.4 Hz, 1H), 2.18 (td, J = 11.3, 2.7 Hz, 1H), 2.40 (qd, J = 13.3, 5.4 Hz, 1H), 2.78-3.12 (m, 7H), 3.27 (td, J = 9.9, 4.4 Hz, 1H), 4.08 (ddd, J = 14.6, 7.7, 3.1 Hz, 1H), 4.14-4.38 (m, 2H), 5.00 (brs, 1H), 5.60 (m, 1H), 5.72 (brs, 1H), 6.89 (s, 1H), 7.35 (d, J = 8.2 Hz, 2H), 7.58 (d, J = 8.1 Hz, 2H), 7.86 (d, J = 1.5 Hz, 1H). | 533 |
| H6-18-1 | IG (Hex:EtOH = 60:40) | (400 MHz, DMSO-d₆): δ 8.93 (s, 1H), 8.16 (d, J = 2.0 Hz, 1H), 7.97 (s, 1H), 7.80 (s, 1H), 7.70 (s, 1H), 7.56-7.54 (d, J = 8.0 Hz, 1H), 7.25 (s, 1H), 5.66-5.64 (m, 1H), 4.83-4.71 (m, 2H), 4.33-4.26 (m, 2H), 3.92 (s, 2H), 3.61 (s, 2H), 3.46 (s, 2H), 3.08 (s, 2H), 2.59-2.55 (m, 1H), 2.08-1.96 (m, 2H), 1.57-1.53 (m, 1H); | 536 |
| H6-18-2 | IG (Hex:EtOH = 60:40) | (400 MHz, DMSO-d₆): δ8.93 (s, 1H), 8.17 (d, J = 8.4 Hz, 1H), 7.94 (s, 1H), 7.80 (s, 1H), 7.69 (s, 1H), 7.55 (d, J = 8.4 Hz, 1H), 7.24 (s, 1H), 5.66-5.63 (m, 1H), 4.77-4.70 (m, 1H), 4.30-4.27 (m, 2H), 3.89 (s, 3H), 3.36-3.25 (m, 3H), 3.13-3.11 (m, 2H), 2.88(s, 1H), 2.54-2.53 (m, 1H), 2.05-1.99 (m, 2H), 1.24-1.22 (m, 1H); | 536 |
| H6-19-1 | IC (Hex:EtOH:DEA = 40:60:0.3) | (400 MHz, CDCl₃): δ8.82 (s, 1H), 7.85 (d, J = 8.4 Hz, 2H), 7.36 (d, J = 8.4 Hz, 1H), 6.95 (br s, 1H), 5.67 (q, J = 4.4 Hz, 1H), 5.54 (br s, 1H), 4.94 (br s, 1H), 4.33-4.19 (m, 2H), 3.72-3.65 (m, 2H), 3.14-3.01 (m, 3H), 2.94-2.87 (m, 2H), 2.68-2.64 (m, 1H), 2.49-2.30 (m, 2H), 2.14-2.04 (m, 1H), 1.86-1.82 (m, 1H), 1.61-1.57 (m, 1H). | 554 |
| H6-19-2 | IC (Hex:EtOH:DEA = 40:60:0.3) | (400 MHz, CDCl₃): δ 8.82 (s, 1H), 7.85 (d, J = 8.8 Hz, 2H), 7.36 (d, J = 8.4 Hz, 1H), 6.95 (br s, 1H), 5.69-5.65 (m, 1H), 5.51 (br s, 1H), 4.92 (br s, 1H), 4.33-4.19 (m, 2H), 3.76-3.59 (m, 2H), 3.14-3.02 (m, 3H), 2.94-2.87 (m, 2H), 2.68-2.64 (m, 1H), 2.48-2.30 (m, 2H), 2.21-2.01 (m, 1H), 1.85-1.82 (m, 1H), 1.64-1.57 (m, 1H). | 554 |
| H6-20 | | (400 MHz, CDCl₃) δ 1.41 (m, 1H), 1.50 (m, 1H), 1.61 (m, 1H), 2.04-2.24 (m, 2H), 2.66 (qd, J = 13.1, 4.8 Hz, 1H), 2.78-2.96 (m, 2H), 2.99 (d, J = 1.9 Hz, 3H), 3.11 (dddd, J = 14.5, 8.7, 5.5, 2.9 Hz, 1H), 3.29 (brd, J = 9.7 Hz, 1H), 4.06 (m, 1H), 4.15-4.39 (m, 2H), 5.11 (m, 1H), 5.35 (m, 1H), 5.67 (td, J = 8.9, 4.8 Hz, 1H), 5.76 (m, 1H), 6.89 (d, J = 3.9 Hz, 1H), 7.37 (d, J = 8.2 Hz, 1H), 7.72-7.96 (m, 2H), 8.70-8.94 (m, 1H). | 534 |

-continued

| Ex. No. | Chiral separation | ¹H-NMR | m/z (M + H)⁺ |
|---|---|---|---|
| H6-21-1 | 1) OJ-H (Hex:IPA = 98:2) 2) IG (Hex:EtOH:DEA = 80:20:0.3) | ND | 527 |
| H6-21-2 | 1) OJ-H (Hex:IPA = 98:2) 2) IG (Hex:EtOH:DEA = 80:20:0.3) | ND | 527 |
| H6-21-3 | 1) OJ-H (Hex:IPA = 98:2) 2) IG (Hex:EtOH:DEA = 80:20:0.3) | (400 MHz, CD₃OD) δ 7.97 (s, 1H), 7.69 (s, 1H), 7.60 (d, J = 8.0 Hz, 1H), 7.48 (d, J = 8.0 Hz, 1H), 7.39-7.43 (t, J = 8.0, 1H), 4.91-4.94 (m, 1H), 3.86-3.95 (m, 3H), 3.56-3.62 (m, 2H), 3.49-3.51 (m, 2H), 3.38-4.45 (m, 1H), 2.94-2.97 (m, 3H), 2.79 (d, J = 16, 1H), 1.96-2.09 (m, 2H), 1.64-1.68 (m, 1H), 1.47-1.28 (m, 3H), 0.91 (d, J = 8.0 Hz, 3H) | 527 |
| H6-21-4 | 1) OJ-H (Hex:IPA = 98:2) 2) IG (Hex:EtOH:DEA = 80:20:0.3) | (400 MHz, CD₃OD) δ 7.96 (s, 1H), 7.70 (s, 1H), 7.48 (d, J = 8 Hz, 1H), 7.39-7.43 (t, J = 8 Hz, 1H), 4.91-4.95 (m, 1H), 3.85-3.96 (m, 3H), 3.56-3.60 (m, 2H), 3.50-3.52 (m, 2H), 3.36-3.42 (m, 1H), 2.94-3.02 (m, 3H), 2.77 (d, J = 12 Hz, 1H), 1.96-2.10 (m, 2H), 1.62-1.66 (m, 1H), 1.27-1.47 (m, 2H), 0.91 (d, J = 8 Hz, 3H) | 527 |
| H6-22-1 | 1) OD-H (Hex:IPA = 98:2) 2) IC (Hex:EtOH = 60:40) | (400 MHz, CDCl₃) δ 8.02 (d, J = 0.8 Hz, 1H), 7.56 (d, J = 8.0 Hz, 2H), 7.50 (d, J = 8.0 Hz, 2H), 6.91 (s, 1H), 5.55-5.56 (m, 1H), 5.48-5.50 (m, 1H), 5.37-5.38 (m, 1H), 5.15-5.20 (m, 1H), 4.33-4.38 (dd, J = 12.0, 4.0 Hz, 1H), 4.08-4.15 (m, 1H), 3.97-4.01 (m, 1H), 3.84-3.93 (m, 2H), 3.69-3.73 (dd, J = 11.2, 4.0 Hz, 1H), 3.33-3.35 (m, 1H), 3.11-3.17 (m, 1H), 3.03-3.07 (m, 3H), 2.85-2.89 (m, 1H), 2.11-2.24 (m, 2H), 1.62-1.67 (m, 1H), 1.52-1.56 (m, 1H), 1.43-1.48 (m, 1H), 1.00 (d, J = 6.8 Hz, 2H) | 527 |
| H6-22-2 | 1) OD-H (Hex:IPA = 98:2) 2) IC (Hex:EtOH = 60:40)) | (400 MHz, CDCl₃) δ 8.02 (d, J = 1.2 Hz, 1H), 7.59 (d, J = 8.4 Hz, 2H), 7.54 (d, J = 8.4 Hz, 2H), 6.89 (s, 1H), 5.48-5.52 (m, 2H), 5.29-5.30 (m, 1H), 5.15-5.20 (m, 1H), 4.34-4.39 (dd, J = 12.0, 4.0 Hz, 1H), 4.03-4.09 (m, 2H), 3.84-3.94 (m, 2H), 3.69-3.74 (dd, J = 11.2, 3.6 Hz, 1H), 3.26-3.36 (m, 1H), 3.13-3.23 (m, 1H), 3.03-3.07 (m, 3H), 2.85-2.89 (m, 1H), 2.10-2.22 (m, 2H), 1.62-1.65 (m, 1H), 1.49-1.54 (m, 1H), 1.43-1.47 (m, 1H), 1.00 (d, J = 6.8 Hz, 2H) | 527 |
| H6-22-3 | 1) OD-H (Hex:IPA = 98:2) 2) IC (Hex:EtOH = 60:40) | ND | 527 |
| H6-22-4 | 1) OD-H (Hex:IPA = 98:2) 2) IC (Hex:EtOH = 60:40) | ND | 527 |
| H6-23 | | ND | 512 |
| H6-24 | | ND | 516 |
| H6-25 | | ND | 480 |
| H6-25-1 | | ND | 480 |
| H6-26 | | ND | 496 |

| Ex. No. | Chiral separation | ¹H-NMR | m/z (M + H)⁺ |
|---|---|---|---|
| H6-27 | | ND | 498 |
| H6-28 | | ND | 466 |
| H6-29 | | ND | 462 |
| H6-30 | | ND | 509 |
| H6-31 | | ND | 509 |
| H6-32 | | ND | 482 |

Biological Evaluation

The activity of the compounds was evaluated using a RORγ Reporter assay (also referred to as Gal4 assay). The Gal4 and the Th17 assays (another suitable assay) are both cell-based assays monitoring functional activity of the compound assayed.

Compounds disclosed herein have also been evaluated in a mouse in vivo pharmacodynamic model (anti-CD3-induced plasma IL-17A).

In addition, the compounds disclosed herein may be evaluated in various mouse disease models, e.g. Experimental Autoimmune Encephalomyelitis (EAE) model (an animal model for multiple sclerosis), and Collagen-induced Arthritis (CIA) model (an animal model for rheumatoid arthritis).

Th17 Assay (Another Suitable Assay)

Human peripheral blood mononuclear cells (PBMCs) were isolated from buffy coats of healthy human volunteers using the Ficoll paque PLUS kit (GE Healthcare, cat no 17-1440-02), as instructed by the manufacturer. Naïve CD4+ T cells were isolated with Naive CD4+ T cell kit, human (Milteny Biotec, cat no 130-094-131). The following modifications were made to the manufacturer's protocol: 1) Incubation with Biotin-Antibody Cocktail and Anti-Biotin MicroBeads was prolonged to 30 minutes, and 2) Cells were washed with 40 mL of Miltenyi buffer. Differentiation of Th17 cells in anti-CD3 (BD Pharmingen, 5 µg/ml) coated 96-well plates (400,000 cells/well, 160 µl RPMI1640+10% Fetal Bovine Serum) containing 5 µg/ml anti-CD28 (BD Pharmingen), 10 ng/ml IL-2 (R&D Systems), 2.5 ng/ml TGFβ-1 (R&D Systems), 20 ng/ml IL-1β (R&D Systems), 20 ng/ml IL-6 (R&D Systems), 30 ng/ml IL-23 (R&D Systems), 2.5 µg/ml anti-IL-4 (R&D Systems) and 1 µg/ml anti-IFNγ (R&D Systems) and with test compound during the entire differentiation (or vehicle, 0.1% DMSO for control). Test compounds were tested in triplicates, diluted 1000-fold in medium (final DMSO concentration is 0.1%). Incubated for seven days at 37° C., 5% $CO_2$, 95% humidity, and 2-fluoro-4'-[[4-(4-pyridinylmethyl)-1-piperazinyl]methyl]-α,α-bis(trifluoromethyl)-[1,1'-biphenyl]-4-methanol (SR2211 Calbiochem, Cat. No. 557353) was used as positive control. As negative control, cells were differentiated into Th0 using 5 µg/ml anti-CD28 (BD Pharmingen), 10 ng/ml IL-2 (R&D Systems), 2 µg/ml anti-IL4 (R&D Systems) and 2 µg/ml anti-IFNγ (R&D Systems) are negative control. IL-17 levels in supernatants were measured with ELISA (R&D Systems). Representative results of the Th17 assay are shown in the table 2.

TABLE 2

| Example | IC50 (nM) |
|---|---|
| H6-5 | 161 nM |
| H6-11-2 | 82 nM |
| H6-13-2 | 93 nM |

RORγ Reporter Assay (Gal4)

The HEK293 cell line is co-transfected transiently with two plasmids, one with the RORγ ligand-binding domain fused to galactose-responsive transcription factor (Gal4), and the other with the luciferase reporter gene and Gal binding sites (UAS). This construction allows to determine the RORγ activity in a cellular system through the measurement of luminescence.

A suspension of RORγ reporter cells was dispensed into plates and cultured 2 h at 37° C. and 5% CO2. Media formulation consisted in DMEM/F-12 medium (Gibco) supplemented with 10% heat inactivated FBS (Sigma-Aldrich), non-essential aminoacids (Sigma-Aldrich), 2 mM Glutamax (Gibco) and 100 U/mF penicillin (Sigma-Aldrich). Dose-response curves with compounds were prepared in 100% DMSO and further diluted 100-fold in culture medium. Compound solutions were added to the plate containing cells (final DMSO concentration of 0.1%) and incubated for 24 h at 37° C. and 5% CO2. Luciferase detection reagent was added to each well, and relative light units (RFUs) were quantified from each assay well using a plate reading luminometer.

Values of average RFU±S.D. were computed for all treatment sets, followed by the calculations of percent-reduction of RORγ activity in response to respective test compound. The following formula was used: activity=100*[1–[x test compound/average vehicle]where the theoretical minimum reduction (0% reduction). For all experiments, the activity values were plotted versus compound concentrations in one single plot and adjusted to a four-parameter logistic curve to obtain the absolute IC50 value along with the 95% confidence interval. These calculations were performed in excel-fit software using X-204 model curve.

The results of RORγ Reporter (Gal4) Assay are shown in the Table 3 below.

TABLE 3

| RORγ Reporter Assay (Gal4) | |
|---|---|
| Patent Example | $IC_{50}$ (nM) |
| H6-1 | 910 |
| H6-2 | 330 |
| H6-3 | 280 |
| H6-4 | 56 |

TABLE 3-continued

RORγ Reporter Assay (Gal4)

| Patent Example | IC$_{50}$ (nM) |
|---|---|
| H6-5 | 70 |
| H6-6 | 51 |
| H6-7-1 | 20 |
| H6-7-2 | 35 |
| H6-8 | 160 |
| H6-9-1 | 100 |
| H6-9-2 | 18 |
| H6-10-1 | 39 |
| H6-10-2 | 13 |
| H6-11-1 | 360 |
| H6-11-2 | 66 |
| H6-12-1 | 550 |
| H6-12-2 | 910 |
| H6-13-1 | 160 |
| H6-13-2 | 54 |
| H6-14 | 230 |
| H6-15-1 | 9 |
| H6-15-2 | 25 |
| H6-16-1 | 14 |
| H6-16-2 | 10 |
| H6-17 | 10 |
| H6-17-1 | 26 |
| H6-17-2 | 31 |
| H6-18-1 | 140 |
| H6-18-2 | 60 |
| H6-19-2 | 46 |
| H6-20 | 488 |
| H6-21-3 | 86 |
| H6-21-4 | 120 |
| H6-22-1 | 44 |
| H6-22-2 | 60 |
| H6-23 | 190 |
| H6-24 | 140 |
| H6-25 | 88 |
| H6-25-1 | 66 |
| H6-26 | 440 |
| H6-27 | 210 |
| H6-28 | 300 |

As can be seen from the Table 3 above, the fluoropyrimidine derivatives of the present disclosure were found to show beneficial activity across the RORγ Reporter (Gal4) Assay.

According to an embodiment, compounds having IC$_{50}$<1000 nM values in the RORγ Reporter Assay (Gal4) are disclosed herein.

According to another preferred embodiment compounds having IC$_{50}$<500 nM values in the RORγ Reporter Assay (Gal4) are disclosed herein.

According to another more preferred embodiment compounds having IC$_{50}$<100 nM values in the RORγ Reporter Assay (Gal4) are disclosed herein.

Collagen-Induced Arthritis (CIA) Study

Collagen-induced arthritis is an animal model of rheumatoid arthritis used to evaluate the efficacy of test compounds. CIA was induced at Washington Biotechnology Inc. (Baltimore) in male DBA/1J mice (Jackson Laboratories) by subcutaneous injection at the base of the tail with 50 µl of a bovine collagen/complete Freund's adjuvant emulsion. After 21 days, the mice were further boosted by a further subcutaneous injection of 50 µl of a collagen/incomplete Freund's adjuvant emulsion. For treatment, compound or vehicle (2% DMSO, 10% HP—β-CD in MilliQ water) was given orally twice daily at various doses selected from 3, 10, 30 mg/kg, beginning at the day of CIA induction (Prophylactic setting), or after disease initiation (at day 27, therapeutic setting). Treatment lasted until day 41, and the animals were scored three times weekly. Each paw was scored and the sum of all four scores was recorded as the Arthritic Index (AI). The maximum possible AI was 16. 0=no visible effects of arthritis; 1=edema and/or erythema of one digit; 2=edema and/or erythema of 2 joints; 3=edema and/or erythema of more than 2 joints; 4=severe arthritis of the entire paw and digits including limb deformation and ankylosis of the joint. The Arthritis Index for each treatment can be expressed as the mean score for each treatment group+/−S.E.M. Compounds H6-13-2, and H6-11-2 were tested in the model. At 10 mpk po bid, H6-13-2 Arthritis Index (AI) decreased with 83% of the effect of the mouse aIL-17A antibody. Also, for H6-11-2 dosed 10 mpk po bid, the AI decreased with 61% of the effect of the mouse aIL-17A antibody.

In Vivo IL-17A Induction in Anti-CD3 Model in Mice

Male C57BL/6JRj mice (7 week old) were purchased from Janvier Labs and housed at the animal facilities of Almirall throughout the study. Animals were allowed to condition for 5 days in their new environment at 22° C.±2° C., 55%±10% relative humidity and 12 h:12 h light:dark cycles. Animals were housed in polycarbonate cages, with free access to water and non-purified stock diet (2014 Teklad Global 14% Protein Rodent Maintenance Diet, Envigo) during the full course of the studies. Care of animals was undertaken in compliance with the European Committee Directive 2010/63/EU, and the Catalan and Spanish law. All procedures were performed according to the ARRIVE guidelines (Animal Research: Reporting of In Vivo Experiments) and with approval from the Animal Experimentation Ethical Committee of Almirall (Barcelona, Spain).

Mice were injected intraperitoneally with 7.5 µg of anti-CD3e (Clone 145-201 from Pharmingen BD) at 0 h (day 0) and 48 h (day 3) time-points. The non-induced-group were injected with PBS instead of anti-CD3e. At study completion (4 h after anti-CD3e injection), animals were anaesthetized with isofluorane (Baxter) and 0.5-1 mL blood samples were drawn by intracardiac puncture in heparinized tubes. Plasma samples were stored at −80° C. for subsequent analysis.

Test compounds were freshly suspended in sterile 0.5% methylcellulose 0.1% tween-80 solution (10 mL/kg body weight). Compounds administered by oral gavage according to the selected dosing and body weight; control animals received an equivalent volume of vehicle. Treatments were given twice daily from day 0 to day 3, last administration was done 1 h before anti-CD3e injection.

Plasma levels of IL-17A were measured by ELISA (R&D Systems) according to the manufacturer's instruction. Results were calculated as the percentage of reduction of plasma IL-17A versus the difference between non-induced and anti-CD3e induced groups through the formula: inhibition=100*[1−[(x−mean non-induced)/(mean control vehicle−mean non-induced)]]. The IL-17A inhibition for each treatment can be expressed as the mean for each treatment group±S.E.M. Statistical analysis of data were conducted with one-way ANOVA followed by Dunnett's multiple comparisons test when appropriate. Differences were considered significant when p<0.05.

Results:

| Compound | Inhibition of IL-17A (%) at 3 mg/kg |
|---|---|
| H6-17-1 | 67% |

In summary, compounds disclosed herein have been found to at least modulate the activity of RORγ. Compounds disclosed herein are active, e.g. having a Gal4<1000 nM, such as <500 nM and such as <100 nM. Additionally, in a property comparison study they have shown an improved lipophilicity manifested by a decrease in Log P and/or Log D compared to previously described high potent compounds, see e.g. Tables 4 a-c. In these tables, all numbers (except Gal4 activity) are calculated; methods are indicated in column titles.

TABLE 4a

| Examples | RORγ Gal4 assay | Number of compounds | ALogP Canvas[1] | LipE Canvas[1] |
|---|---|---|---|---|
| Compounds disclosed herein | $IC_{50}$ < 100 nM | 24 | 3.09 | 4.39 |
| Compounds disclosed in WO2016020295 | $IC_{50}$ < 100 nM[1] | 18[2] | 4.62 | 2.94 |

TABLE 4b

| Examples | RORγ Gal4 assay | Number of compounds | ALogP Canvas[1] | LipE Canvas[1] |
|---|---|---|---|---|
| Compounds disclosed herein | $IC_{50}$ < 500 nM | 39 | 3.03 | 4.14 |
| Compounds disclosed in WO2016020295 | $IC_{50}$ < 500 nM[1] | 21[3] | 4.81 | 2.67 |

TABLE 4c

| Examples | RORγ Gal4 assay (based on % inhibition at 0.1 and/or 1 uM) | Number of compounds | ALogP Canvas[1] |
|---|---|---|---|
| Compounds disclosed in WO2016020295 | $IC_{50}$ < 100 nM | 113[4] | 4.58 |
| Compounds disclosed in WO2016020295 | $IC_{50}$ < 500 nM[1] | 125[5] | 4.67 |

The RORγ Gal4 data used to generate the comparisons in Tables 4 a and b are based on generated Gal4 data for the listed compounds (data not available in WO2016020295). LipE has not been reported in Table 4c as Gal4 data existed as % inhibition only, except for the compounds used in Tables 4a and b. In connection with the above Tables 4 a-c, Tables 5 and 6 show a comparison between compounds of the present disclosure and known compounds of structural similarity, and considered relevant.

TABLE 5

ALogP numbers are calculated by Canvas.

| Structure | | | | |
|---|---|---|---|---|
| Ex. No | H6-9-2 | H6-7-1 | Example 204[1] | Example 206[1] |
| Gal4 assay | $IC_{50}$ nM (Table 3 herein) | $IC_{50}$ nM (Table 3 herein) | $IC_{50}$ < 500 nM Compound from[1] | $IC_{50}$ < 1000 nM Compound from[1] |
| ALogP Canvas | 3.20 | 2.10 | 4.14 | 4.51 |

[1]WO2016020295

TABLE 6

ALogP numbers are calculated by Canvas.

| Structure | | | | |
|---|---|---|---|---|
| Ex. No | H6-6 | H6-23 | Example 230[1] | Example 245[1] |
| Gal4 assay | $IC_{50}$ nM (Table 3 herein) | $IC_{50}$ nM (Table 3 herein) | $IC_{50}$ < 100 nM Compound from[1] | $IC_{50}$ < 500 nM Compound from[1] |
| ALogP Canvas | 3.92 | 4.24 | 5.32 | 5.69 |

[1]WO2016020295

The A Log P and LipE are calculated using Canvas, a part of the Schrödinger software suite, Release 2019-1.

As mentioned, the compounds disclosed herein may thus be improved modulators of RORγ, e.g. having an attractive interaction (e.g. high binding ability) to the hydrophobic binding sites of the ligand binding domain (LBD) of the RORγ receptor and improved physical chemical properties as discussed above.

Additionally it has been found that compounds disclosed herein have in vivo usefulness, and could consequently be useful in treating inflammatory, metabolic and autoimmune diseases or symptoms thereof.

The invention claimed is:

1. A compound according to Formula (I)

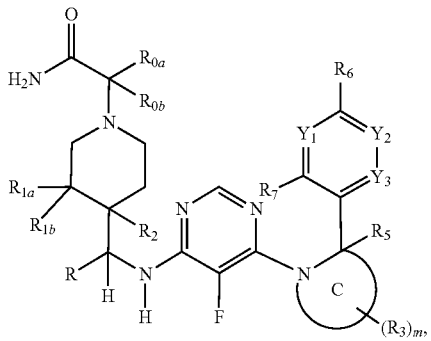

(I)

a stereoisomer thereof, or a pharmaceutically acceptable salt of the compound or stereoisomer, wherein:

$Y_1$, $Y_2$ and $Y_3$ are independently —N— or —$CR_8$—;

m is independently selected from 0, 1, and 2;

R is selected from the group consisting of hydrogen, $C_{1-6}$ alkyl and $C_{1-4}$ hydroxyalkyl;

$R_{0a}$ and $R_{0b}$ independently are selected from the group consisting of hydrogen, $C_{1-4}$ alkyl, $C_{1-4}$ hydroxyalkyl, and $C_{1-4}$ haloalkyl;

$R_{1a}$ and $R_{1b}$ are independently selected from the group consisting of hydrogen, hydroxyl, halogen, amino, $C_{1-4}$ alkyl, $C_{1-4}$ hydroxyalkyl, and $C_{1-4}$ haloalkyl;

$R_2$ is selected from the group consisting of hydrogen, hydroxyl, amino, cyano, halogen, $C_{1-4}$ alkyl, $C_{1-4}$ haloalkyl, $C_{1-4}$ hydroxyalkyl, —C(=O)$NH_2$, —C(=O)OH, —C(=O)O—$C_{1-4}$ alkyl, and substituted or unsubstituted heteroaryl;

Ring C is a 3 to 10 membered heteroalicyclyl ring system containing 0, 1, or 2 heteroatoms independently selected from N, O and S in addition to the one N atom shown in the C ring in the compound of Formula I;

Each $R_3$ is independently selected from the group consisting of hydrogen, halogen, hydroxyl, $C_{1-4}$ alkyl, $C_{1-4}$ haloalkyl, $C_{1-4}$ hydroxyalkyl; and $C_{1-4}$ hydroxyhaloalkyl;

$R_5$ is absent, hydrogen or $C_{1-4}$ alkyl;

$R_6$ is selected from the group consisting of hydrogen, —CN, halogen, $C_{1-4}$ alkyl, $C_{1-4}$ haloalkyl, $C_{1-4}$ hydroxyalkyl, $C_{1-4}$ hydroxyhaloalkyl, $C_{1-4}$ alkoxy, $C_{1-4}$ haloalkoxy, and substituted or unsubstituted heteroaryl;

$R_7$ is selected from the group consisting of hydrogen, hydroxyl, —CN, halogen, $C_{1-4}$ alkyl, $C_{1-4}$ haloalkyl, $C_{1-4}$ hydroxyalkyl, $C_{1-4}$ alkoxy, and $C_{1-4}$ haloalkoxy;

each $R_8$ is independently selected from the group consisting of hydrogen, hydroxyl, —CN, halogen, $C_{1-4}$ alkyl, $C_{1-4}$ haloalkyl, $C_{1-4}$ hydroxyalkyl, $C_{1-4}$ alkoxy, and $C_{1-4}$ haloalkoxy; and whenever $R_7$ is hydrogen and each $R_8$ present is hydrogen, then $R_6$ is selected from the group consisting of —CN, halogen, $C_{1-4}$ alkyl, $C_{1-4}$ haloalkyl, $C_{1-4}$ hydroxyalkyl, $C_{1-4}$ hydroxyhaloalkyl, $C_{1-4}$ alkoxy, $C_{1-4}$ haloalkoxy, and substituted or unsubstituted heteroaryl, and wherein when substituted, a heteroaryl is substituted with 1 to 3 groups independently selected from the group consisting of $C_{1-4}$ alkyl, $C_{1-4}$ hydroxyalkyl, $C_{2-4}$ alkenyl, $C_{2-4}$ alkynyl, hydroxy, $C_{1-4}$ alkoxy, cyano, halogen, $C_{1-4}$ haloalkyl, $C_{1-4}$ haloalkoxy and $C_{1-6}$ hydroxyhaloalkyl.

2. The compound, stereoisomer, or salt of claim 1, wherein R is hydrogen.

3. The compound, stereoisomer, or salt of claim 1, wherein $R_{0a}$ is selected from the group consisting of hydrogen, methyl, —$CH_2OH$, —$CH_2CH_2OH$, —$CH_2F$, and —$CHF_2$; and $R_{0b}$ is selected from the group consisting of hydrogen, $C_{1-4}$ alkyl, $C_{1-4}$ hydroxyalkyl, and $C_{1-4}$ haloalkyl.

4. The compound, stereoisomer, or salt of claim 1, wherein at least one of $R_{1a}$, $R_{1b}$ and $R_2$ is not hydrogen.

5. The compound, stereoisomer, or salt of claim 1, wherein Ria is selected from the group consisting of hydroxyl, fluoro and —$CF_3$, and $R_{1b}$ is selected from the group consisting of hydrogen, fluoro, and methyl.

6. The compound, stereoisomer, or salt of claim 1, wherein Rib is hydrogen.

7. The compound, stereoisomer, or salt of claim 1, wherein $R_2$ is selected from the group consisting of hydrogen, halogen, hydroxyl, cyano, methyl, ethyl, —$CH_2OH$, —$CH_2CH_2OH$ and —C(=O)O—$C_{1-2}$ alkyl.

8. The compound, stereoisomer, or salt of claim 1, wherein ring C is a 4 membered heteroalicyclyl, 5-membered heteroalicyclyl, or 6-membered heteroalicyclyl.

9. The compound, stereoisomer, or salt of claim 1, wherein m is 0.

10. The compound, stereoisomer, or salt of claim 1, wherein each $R_3$ is independently halogen or methyl, and m is 1 or 2.

11. The compound, stereoisomer, or salt of claim 1, wherein $R_5$ is hydrogen.

12. The compound, stereoisomer, or salt of claim 1, wherein $R_6$ is selected from the group consisting of hydrogen, halogen, $C_{1-4}$ haloalkyl, $C_{1-4}$ haloalkoxy, $C_{1-4}$ hydroxyalkyl, $C_{1-4}$ hydroxyhaloalkyl, and substituted or unsubstituted 5 membered heteroaryl.

13. The compound, stereoisomer, or salt of claim 1, wherein $R_7$ is selected from the group consisting of hydrogen, halogen, hydroxyl, cyano, —$CF_3$, —$OCHF_2$, —$CHF_2$ and —$OCF_3$.

14. The compound, stereoisomer, or salt of claim 1, wherein $Y_1$, $Y_2$ and $Y_3$ independently are each —CH—; or $Y_1$ is —N— and $Y_2$ and $Y_3$ independently are each —CH—; or $Y_2$ is —N— and $Y_1$ and $Y_3$ independently are each —CH—; or $Y_3$ is —N— and $Y_1$ and $Y_2$ independently are each —CH—; or $Y_3$ is —CH— and $Y_1$ and $Y_2$ are each —N—.

15. The compound, stereoisomer, or salt of claim 1, wherein
  $Y_1$ is —CH—, $Y_2$ and $Y_3$ are independently each —$CR_8$—, and each $R_8$ independently is selected from the group consisting of hydrogen, methyl, fluoro, hydroxyl and —$CF_3$.

16. The compound, stereoisomer, or salt according to claim 15, wherein each $R_8$ is hydrogen.

17. The compound, stereoisomer, or salt of claim 1, wherein $R_6$ is hydrogen, at least one of $Y_2$ or $Y_3$ is —$CR_8$—, and $R_8$ is selected from the group consisting of —CN, hydroxyl, halogen, $C_{1-4}$ alkyl, $C_{1-4}$ haloalkyl, $C_{1-4}$ hydroxyalkyl, $C_{1-4}$ alkoxy, and $C_{1-4}$ haloalkoxy.

18. The compound, stereoisomer, or salt according to claim 1, wherein:
  R is hydrogen;
  $R_{0a}$ and $R_{0b}$ independently are hydrogen or methyl;
  $R_{1a}$ is selected from the group consisting of hydrogen, fluoro and hydroxyl;
  $R_{1b}$ is hydrogen or fluoro;
  $R_2$ is selected from the group consisting of hydrogen, fluoro and hydroxyl;
  ring C is selected from the group consisting of azetidinyl, pyrrolidinyl, morpholinyl, 2-azabicyclo[3.1.0]hexanyl and 3-azabicyclo[3.1.0]hexanyl;
  m is selected from the group consisting of 0, 1 and 2;
  $R_3$ is selected from the group consisting of hydrogen, fluoro and methyl;
  $R_5$ is absent or hydrogen;
  $R_6$ is selected from the group consisting of hydrogen, —$CF_3$, —$OCF_3$ and —Cl;
  $R_7$ is hydrogen or fluoro;
  $Y_1$, $Y_2$ and $Y_3$ are each —CH—; or
  $Y_1$ is —CH—, $Y_2$ is —CH— and $Y_3$ is —C(OH)—; or
  $Y_1$ is —CH—, $Y_2$ is —CH— and $Y_3$ is —N—; or
  $Y_1$ is —CH—, $Y_2$ is —C(CF_3)— and $Y_3$ is —CH—; or
  $Y_1$ is —CH—, $Y_2$ is —N— and $Y_3$ is —CH—.

19. The compound, stereoisomer, or salt according to claim 1, selected from the group consisting of:
  2-(4-(((5-fluoro-6-(3-(5-trifluoromethyl)pyridin-2-yl)morpholino)pyrimidin-4-yl)amino)methyl)piperidin-1-yl)propanamide,
  2-(4-(((5-fluoro-6-(3-(5-(trifluoromethyl)pyridin-2-yl)morpholino)pyrimidin-4-yl)amino)methyl)piperidin-1-yl)acetamide,
  2-(4-(((5-fluoro-6-(3-(5-(trifluoromethyl)pyridin-2-yl)morpholino)pyrimidin-4-yl)amino)methyl)piperidin-1-yl)-2-methylpropanamide,
  2-(4-fluoro-4-(((5-fluoro-6-(3-(4-(trifluoromethyl)phenyl)morpholino)pyrimidin-4-yl)amino)methyl)piperidin-1-yl)acetamide,
  2-(4-(((5-fluoro-6-(3-(4-(trifluoromethyl)phenyl)morpholino)pyrimidin-4-yl)amino)methyl)piperidin-1-yl)acetamide,
  2-(4-fluoro-4-(((5-fluoro-6-(3-(4-(trifluoromethoxy)phenyl)morpholino)pyrimidin-4-yl)amino)methyl)piperidin-1-yl)acetamide,
  2-(4-(((5-fluoro-6-(3-(4-(trifluoromethyl)phenyl)morpholino)pyrimidin-4-yl)amino)methyl)-3-hydroxypiperidin-1-yl)acetamide,
  2-(4-fluoro-4-(((5-fluoro-6-(3-(5-(trifluoromethyl)pyridin-2-yl)morpholino)pyrimidin-4-yl)amino)methyl)piperidin-1-yl)acetamide,
  2-(3,3-difluoro-4-(((5-fluoro-6-(3-(4-(trifluoromethyl)phenyl)morpholino)pyrimidin-4-yl)amino)methyl)piperidin-1-yl)acetamide,
  2-(3-fluoro-4-(((5-fluoro-6-(3-(4-(trifluoromethyl)phenyl)morpholino)pyrimidin-4-yl)amino)methyl)piperidin-1-yl)acetamide,
  2-(3,3-difluoro-4-(((5-fluoro-6-(3-(5-(trifluoromethyl)pyridin-2-yl)morpholino)pyrimidin-4-yl)amino)methyl)piperidin-1-yl)acetamide,
  2-(3-fluoro-4-(((5-fluoro-6-(3-(5-(trifluoromethyl)pyridin-2-yl)morpholino)pyrimidin-4-yl)amino)methyl)piperidin-1-yl)acetamide,
  2-(4-(((6-(4,4-difluoro-2-(4-(trifluoromethyl)phenyl)pyrrolidin-1-yl)-5-fluoropyrimidin-4-yl)amino)methyl)-4-hydroxypiperidin-1-yl)acetamide,
  2-(4-(((6-(4,4-difluoro-2-(4-(trifluoromethyl)phenyl)pyrrolidin-1-yl)-5-fluoropyrimidin-4-yl)amino)methyl)-3,3-difluoropiperidin-1-yl)acetamide,
  2-(4-(((6-(4,4-difluoro-2-(4-(trifluoromethyl)phenyl)pyrrolidin-1-yl)-5-fluoropyrimidin-4-yl)amino)methyl)-3-fluoropiperidin-1-yl)acetamide,
  2-(4-(((6-(4,4-difluoro-2-(4-(trifluoromethyl)phenyl)pyrrolidin-1-yl)-5-fluoropyrimidin-4-yl)amino)methyl)-3-hydroxypiperidin-1-yl)acetamide,
  2-(4-(((6-(4,4-difluoro-2-(5-(trifluoromethyl)pyridin-2-yl)pyrrolidin-1-yl)-5-fluoropyrimidin-4-yl)amino)methyl)-3-fluoropiperidin-1-yl)acetamide,
  2-(4-(((6-(4,4-difluoro-2-(5-(trifluoromethyl)pyridin-2-yl)pyrrolidin-1-yl)-5-fluoropyrimidin-4-yl)amino)methyl)-3,3-difluoropiperidin-1-yl)acetamide,
  2-(4-(((6-(4,4-difluoro-2-(5-(trifluoromethyl)pyridin-2-yl)pyrrolidin-1-yl)-5-fluoropyrimidin-4-yl)amino)methyl)-3-hydroxypiperidin-1-yl)acetamide,
  2-(4-(((5-fluoro-6-(3-methyl-5-(3-(trifluoromethyl)phenyl)morpholino)pyrimidin-4-yl)amino)methyl)-3-hydroxypiperidin-1-yl)acetamide,
  2-(4-(((5-fluoro-6-(3-methyl-5-(4-(trifluoromethyl)phenyl)morpholino)pyrimidin-4-yl)amino)methyl)-3-hydroxypiperidin-1-yl)acetamide,
  2-(4-(((5-fluoro-6-(3-(4-(trifluoromethoxy)phenyl)morpholino)pyrimidin-4-yl)amino)methyl)piperidin-1-yl)acetamide,
  2-(4-(((6-(4,4-difluoro-2-(4-(trifluoromethyl)phenyl)pyrrolidin-1-yl)-5-fluoropyrimidin-4-yl)amino)methyl)piperidin-1-yl)acetamide,
  2-(4-(((5-fluoro-6-(2-(4-(trifluoromethyl)phenyl)pyrrolidin-1-yl)pyrimidin-4-yl)amino)methyl)piperidin-1-yl)acetamide,
  2-(4-(((5-fluoro-6-(2-(2-hydroxy-4-(trifluoromethyl)phenyl)pyrrolidin-1-yl)pyrimidin-4-yl)amino)methyl)piperidin-1-yl)acetamide,
  2-(4-(((5-fluoro-6-(4-fluoro-2-(4-(trifluoromethyl)phenyl)pyrrolidin-1-yl)pyrimidin-4-yl)amino)methyl)piperidin-1-yl)acetamide,
  2-(4-(((5-fluoro-6-(2-(4-(trifluoromethyl)phenyl)azetidin-1-yl)pyrimidin-4-yl)amino)methyl)piperidin-1-yl)acetamide,
  2-(4-(((6-(2-(4-chlorophenyl)pyrrolidin-1-yl)-5-fluoropyrimidin-4-yl)amino)methyl)-3-hydroxypiperidin-1-yl)acetamide,
  2-(4-(((5-fluoro-6-(1-(6-(trifluoromethyl)pyridin-3-yl)-2-azabicyclo[3.1.0]hexan-2-yl)pyrimidin-4-yl)amino)methyl)-3-hydroxypiperidin-1-yl)acetamide,
  2-(4-(((5-fluoro-6-(2-(6-(trifluoromethyl)pyridin-3-yl)-3-azabicyclo[3.1.0]hexan-3-yl)pyrimidin-4-yl)amino)methyl)-3-hydroxypiperidin-1-yl)acetamide,
  2-(4-(((5-fluoro-6-(2-(4-(trifluoromethyl)phenyl)azetidin-1-yl)pyrimidin-4-yl)amino)methyl)-3-hydroxypiperidin-1-yl)acetamide, 2-(4-(((5-fluoro-6-(3-(2-fluoro-4-(trifluoromethyl)phenyl)morpholino)pyrimidin-4-yl)amino)methyl)-3-hydroxypiperidin-1-yl)acetamide, 2-(4-(((5-fluoro-6-(2-(2-fluoro-4-(trifluoromethyl)phenyl)pyrrolidin-1-yl)pyrimidin-4-yl)amino)methyl)-3-hydroxypiperidin-1-yl)acetamide, 2-(3-fluoro-4-(((5-fluoro-6-(2-(2-fluoro-4-(trifluoromethyl)phenyl)pyrrolidin-1-yl)pyrimidin-4-yl)amino)methyl)piperidin-1-yl)acetamide, 2-(3-fluoro-4-(((5-fluoro-6-(3-(2-fluoro-4-(trifluoromethyl)phenyl)morpholino)pyrimidin-4-yl)amino)methyl)piperidin-1-yl)acetamide, 2-(4-(((6-(4,4-difluoro-2-(2-fluoro-4-(trifluoromethyl)phenyl)pyrrolidin-1-yl)-5-fluoropyrimidin-4-yl)amino)methyl)-3-hydroxypiperidin-1-yl)acetamide, 2-(4-(((6-(4,4-difluoro-2-(2-fluoro-4-(trifluoromethyl)phenyl)pyrrolidin-1-yl)-5-fluoropyrimidin-4-yl)amino)methyl)-3-fluoropiperidin-1-yl)acetamide, 2-(3,3-difluoro-4-(((5-fluoro-6-(3-(2-fluoro-4-(trifluoromethyl)phenyl)morpholino)pyrimidin-4-yl)amino)methyl)piperidin-1-yl)acetamide, 2-(3,3-difluoro-4-(((5-fluoro-6-(2-(2-fluoro-4-(trifluoromethyl)phenyl)pyrrolidin-1-yl)pyrimidin-4-yl)amino)methyl)piperidin-1-yl)acetamide, and 2-(4-(((6-(4,4-difluoro-2-(2-fluoro-4-(trifluoromethyl)phenyl)pyrrolidin-1-yl)-5-fluoropyrimidin-4-yl)amino)methyl)-3,3-difluoropiperidin-1-yl)acetamide.

20. The compound, stereoisomer, or salt of claim 1, having a structure of

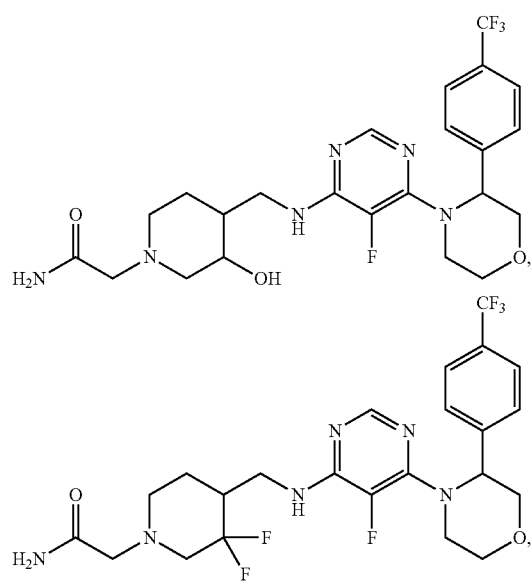

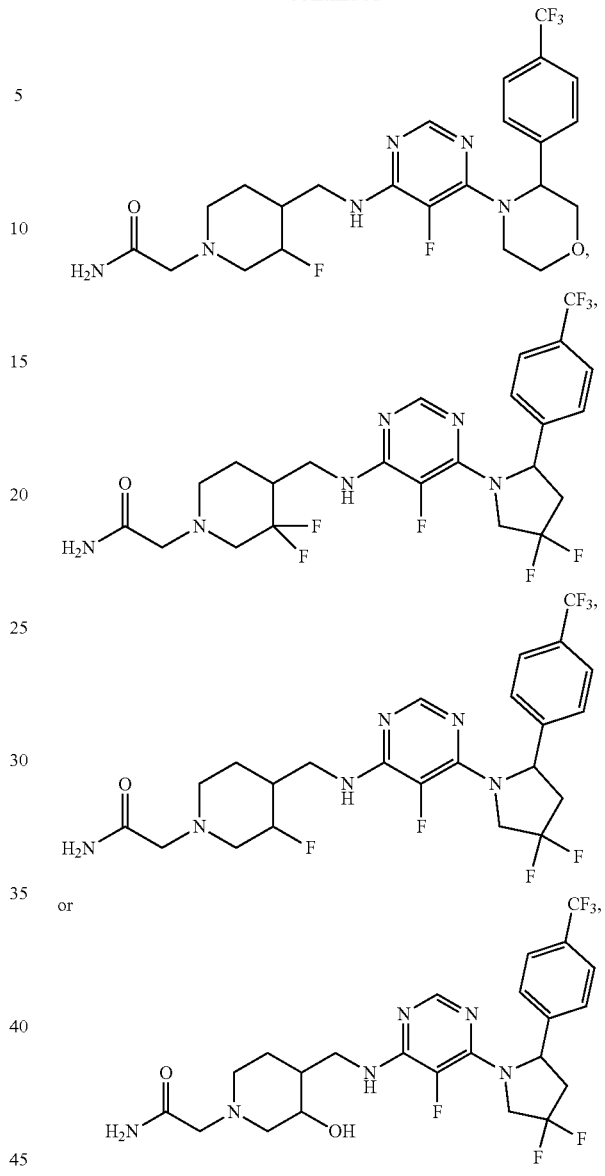

21. A method of treating rheumatoid arthritis in a subject suffering therefore, the method comprising: administering to the subject a therapeutically effective amount of the compound, stereoisomer, or salt of claim 1.

* * * * *

UNITED STATES PATENT AND TRADEMARK OFFICE
CERTIFICATE OF CORRECTION

PATENT NO. : 11,447,479 B2
APPLICATION NO. : 17/126170
DATED : September 20, 2022
INVENTOR(S) : Sanne Schrøder Glad et al.

It is certified that error appears in the above-identified patent and that said Letters Patent is hereby corrected as shown below:

On the Title Page

Above item (74), under "Primary Examiner", Line 1, "Aykakh" should be -- Aulakh --

In the Claims

At Column 145, Line 41, "$C_{1-4}$hydroxyalkyl," should be -- $C_{1-4}$ hydroxyalkyl, --

At Column 146, Line 28, "Ria" should be -- $R_{1a}$ --

At Column 146, Line 29, "-$CF_3$," should be -- -$CF_3$; --

At Column 146, Line 32, "Rib" should be -- $R_{1b}$ --

At Column 147, Line 41, "6-(3-(5-trifluoromethyl)pyridin-2-yl)" should be -- 6-(3-(5-(trifluoromethyl)pyridin-2-yl) --

Signed and Sealed this
Third Day of October, 2023

Katherine Kelly Vidal
*Director of the United States Patent and Trademark Office*